US006348467B1

(12) United States Patent
Corey

(10) Patent No.: US 6,348,467 B1
(45) Date of Patent: Feb. 19, 2002

(54) SYNTHETIC ANALOGS OF ECTEINASCIDIN-743

(75) Inventor: Elias J. Corey, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/510,315

(22) Filed: Feb. 22, 2000

Related U.S. Application Data

(63) Continuation of application No. 09/165,892, filed on Sep. 30, 1998, now Pat. No. 6,124,292.

(51) Int. Cl.[7] .......................... A01N 43/58; C07F 5/02; C07D 241/36

(52) U.S. Cl. ....................... 514/250; 544/229; 544/342; 544/338

(58) Field of Search .......................... 514/250; 544/338, 544/229, 342

(56) References Cited

U.S. PATENT DOCUMENTS

| | | | | |
|---|---|---|---|---|
| 5,089,273 A | 2/1992 | Rinehart et al. | ............ | 424/520 |
| 5,256,663 A | 10/1993 | Rinehart et al. | ............ | 514/250 |
| 5,478,932 A | 12/1995 | Rinehart et al. | ............ | 540/466 |
| 5,654,426 A | 8/1997 | Rinehart et al. | ............ | 540/466 |
| 5,721,362 A | 2/1998 | Corey et al. | ................ | 540/466 |

FOREIGN PATENT DOCUMENTS

JP 63002991 * 1/1988

OTHER PUBLICATIONS

Kobo–Akiyoshi et al. "Studies on the total syn . . . Saframycin B"; Meiji Coll. Pharm. 28th, 465–72, Jan. 1986.*

Corey et al., "Enantioselective Total Synthesis of Ecteinascidin 743", *J. Am. Chem. Soc.,* vol. 118, No. 38, pp. 9201–9203, Sep. 25, 1996.

Sakai et al., Ecteinascidins: Putative Biosynthetic Precursors and Absolute Steriochemistry, *J. Am. Chem. Soc.,* 1996, vol. 118, pp. 9017–9023.

T. Fukuyama et al., "Total Synthesis of Saframycin B", *J. Am. Chem. Soc.* 1990, vol. 112, pp. 3712–3715.

T. Fukuyama et al., "Stereocontrolled Total Synthesis of Saframycin B", *J. Am. Chem. Soc.* 1982, vol. 104, pp. 4957–4958.

J. W. Lown et al., "Molecular Mechanisms of Binding and Single–Strand Scission of Deoxyribonucleic Acid by the Antitumor Antibiotics Saframycins A and C", *Biochemistry,* vol. 21, No. 3, pp. 419–428 (1982).

Rinehart et al., "Bioactive Compounds from Aquatic and Terrestrial Sources", *Journal of Natural Products,* vol. 53, No. 4, pp. 771–792 (1990).

Rinehart et al., "Biologically Active Natural Products", *Pure & App. Chem.,* vol., 62, No. 7, pp. 1277–1280 (1990).

Rinehart et al., "Ecteinascidins 729, 743, 745, 759A, 759Bm and 770: Potent Antitumor Agents from the Caribbean Tunicate *Ecteinascidia turbinata*", *J. Org. Chem.* 1990, 55 pp. 4512–4515.

Amy Wright et al., "Antitumor Tetrahydroisoquinoline Alkaloids from the Colonial Ascidian *Ecteinasccidia turbinata*", *J. Org. Chem.* 1990, 55, pp. 4508–4512.

R. Sakai et al., "Additional and Antitumor Ecteinascidins from a Caribbean Tunicate: Crystal Structures and Activities in vivo", *Proc. Natl. Acad. Sci. USA,* vol. 89, pp. 11456–11460.

"Chemical Prospectors Scour The Seas for Promising Drugs", *Science,* 1994, vol. 266, pp. 1324–1325.

K. Koenig, "Asymmetric Synthesis", vol. 5, 1985, Academic Press, Inc., Orlando, FL., pp. 73–101.

(List continued on next page.)

*Primary Examiner*—Richard L. Raymond
*Assistant Examiner*—Sudhaker B. Patel
(74) *Attorney, Agent, or Firm*—Ernest V. Linek; Banner & Witcoff, Ltd.

(57) ABSTRACT

The present invention is directed to the synthesis and characterization of compounds having the formula:

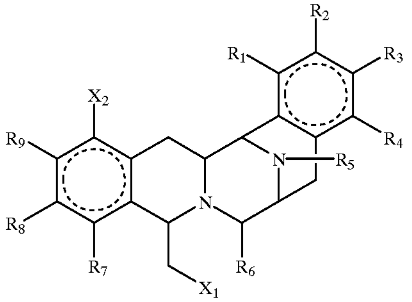

wherein $R_1$, $R_2$, $R_3$, $R_4$, $R_5$, $R_6$, $R_7$, $R_8$ and $R_9$ are each independently selected from the group consisting of H, OH, OR', SH, SR', SOR', $SO_2R'$, $NO_2$, $NH_2$, NHR', $N(R')_2$, NHC(O)R', CN, halogen, =O, C(=O)H, C(=O)R', $CO_2H$, $CO_2R'$, $C_1$–$C_{12}$ alkyl, $C_2$–$C_{12}$ alkenyl, $C_2$–$C_{12}$ alkynyl, substituted or unsubstituted aryl, substituted or unsubstituted aralkyl, and substituted or unsubstituted heteroaromatic;

wherein each of the R' groups is independently selected from the group consisting of H, OH, $NH_2$, $NO_2$, SH, CN, halogen, =O, C(=O)H, C(=O)$CH_3$, $CO_2H$, $CO_2CH_3$, $C_1$–$C_{12}$ alkyl, $C_2$–$C_{12}$ alkenyl, $C_2$–$C_{12}$ alkynyl, aryl, aralkyl, and heteroaromatic;

wherein each dotted circle represents one, two or three optional double bonds;

wherein $R_7$ and $R_8$ may be joined into a carbocyclic or heterocyclic ring system; and wherein $X_1$ and $X_2$ are each independently defined as above for $R_1$–$R_8$, and each further includes specific preferred groups as defined herein.

46 Claims, No Drawings

OTHER PUBLICATIONS

T. Fukuyama et al., "Stereocontrolled Total Synthesis of Saframycin B", *J. Am. Chem. Soc.* 1982, vol. 104, pp. 4957–4958.

T. Fukuyama et al., "Total Synthesis of Saframycin B", *J. Am. Chem. Soc.* 1990, vol. 112, pp. 3713–3715.

N. Saito et al., "Synthesis of Saframycins. 3. Preparation of a Key Tricyclic Lactam Intermediate to Saframycin A", *J. Org. Chem.,* vol. 54, No. 22, (1989) pp. 5392–5395.

W. Clark Still et al., "Rapid Chromatographic Technique for Preparative Separations with Moderate Resolution", *J. Org. Chem.,* vol. 43, No. 14, (1978), pp. 2923–2925.

W. Kofron et al., "A Convenient Method for Estimation of Alkyllithium Concentrations", *J. Org. Chem.,* vol. 41. No. 10, (1976), pp. 1879–1880.

Y. Guan et al., "Molecular and Crystal Structures of Ecteinascidins: Potent Antitumor Compounds from the Caribbean Tunicate *Ecteinascidia turbinata," Journal of Biomolecular Structure & Dynamics,* vol. 10, pp. 7930817 (1993).

J. W. Lown et al., "Molecular Mechanisms of Binding and Single–Strand Scission of Deoxyribonucleic Acid by the Antitumor Antibiotics Saframycins A and C", *Biochemistry,* vol. 21, No. 3, pp. 419–428 (1982).

M. Zmijewski et al., "The In Vitro Interaction of Naphthyridinomycin with Deoxyribonucleic Acids", *Chem.–Biol. Interactions,* vol. 52, pp. 361–375 (1985).

Y. Ito, "High Speed Countercurrent Chromatography", *CRC Critical Reviews in–Analytical Chemistry,* vol. 17, Issue 1, pp. 65–143.

M. Nakagawa et al., "Total Synthesis of (–)–Eudistomin L and (–)–Debromoeudistomin L", *J. Am. Chem. Soc.,* 1989, vol. 111, pp. 2722–2724.

R. Sakai et al., "Ecteinascidins: Putative Biosynthetic Precursors and Absolute Stereochemistry", *J. Am. Chem. Soc.* 1996, vol. 118, pp. 9017–9023.

Y. Pommier et al., "DNA Sequence—and Structure–Selective Alkylation of Guanine N2 in the DNA Minor Groove by Ecteinascidin 743, a Potent Antitumor Compound from the Caribbean Tunicate *Ecteinascidia turbinata,*" *Biochemistry* 1996, vol. 35, pp. 13303–13309.

L. Campayo et al., "Diazapolycyclic Compounds: XXV. Improved Synthesis of 6–Substituted 2,3–Dihydrobenzo [g]phthalazine–1,4–dione Derivatives", *Synthesis Communications,* 1985, pp. 197–200.

Weidner–Wells et al., "Photochemical Approach to the Synthesis of the Pyrrolo[1,4] benzodiazepine Antibiotics", *J. Org. Chem.* 1989, vol. 54, pp. 5746–5758.

Plakidin et al., "Reactive of Naphthalic Anhydride and Its Substituted Derivatives with Acid Amides", *J. Org. Chem.* USSR 1982, vol. 18, pp. 1754–1755.

E.V. Ganin et al., "Reaction of Aromatic Di–and Tetracarboxylic Anhydrides with Amides", *J. Org. Chem. USSR* 1987, vol. 23, pp. 981–983.

M. Alexiou et al., "Nucleophilic Displacement of the Nitro Group In 2–and 4–Nitronaphthalic–1, 8–Anhydrides and Their Derivatives", *Tetrahedron Letters,* vol. 22, No. 24, pp. 2303–2306 (1981).

E. J. Corey et al., "Total Synthesis of a Potent Thromboxane $A_2$ Antagonist", *Tetrahedron Letters,* vol. 31, No. 27, pp. 3833–3836 (1990).

M. Newman et al., "A Convenient Synthesis of 1,2–Naphthalic Anhydride", *J. Org. Chem.,* vol. 41, No. 24, pp. 3925 (1976).

E.J. Corey, et al. "Enantioselective Total Synthesis of Ecteinascidin", *J. Am. Chem. Soc.* 1996, vol. 118, pp. 9202–9203.

E.H.R. Barton, et al., "Synthesis and Properties of a Series of Sterically Hindered Guanidine Bases", *J. Chem. Soc.* 1982, pp. 2085–2090.

Y. Guan, et al. "Molecular and Crystal Structures of Ecteinascidins: Potent Antitumor Compounds from the Caribbean Tunicate *Ecteinascidia turbinata*", *J. Biomolecular Structure & Dynamics,* 1993, vol. 10, No. 5, pp. 793–818.

* cited by examiner

SYNTHETIC ANALOGS OF ECTEINASCIDIN-743

CROSS-REFERENCE TO RELATED APPLICATION

This application is a continuation of application U.S. Ser. No. 09/165,892, filed Sep. 30, 1998, now U.S. Pat. No. 6,124,292, the disclosure of which is hereby incorporated herein by reference.

STATEMENT OF GOVERNMENT SUPPORT

This invention was supported in part by funding from the National Institutes of Health under Grant No. R01 GM 34167 and the National Science Foundation under Grant Nos. CHE 9300276 and CHE 9811917. Accordingly, the government of the United States may have certain rights in this invention.

BACKGROUND OF THE INVENTION

The ecteinascidins (herein abbreviated Et or Et's) are exceedingly potent antitumor agents isolated from the marine tunicate *Ecteinascidia turbinata*. Several ecteinascidins have been reported previously in the patent and scientific literature. See, for example:

U.S. Pat. No. 5,721,362, which describes a synthetic process for the formation of ecteinascidin compounds and related structures, such as the saframycins. In one particularly preferred embodiment, the patent provides a synthetic route for the formation of ecteinascidin 743, an exceedingly potent marine-derived antitumor agent, now in clinical trials. The process of this patent is enantio- and stereocontrolled, convergent and short. Also disclosed are novel process intermediates, useful not only in the total synthesis of ecteinascidin 743, but also other known ecteinascidin compounds, including derivatives and analogs thereof.

U.S. Pat. No. 5,256,663, which describes pharmaceutical compositions comprising matter extracted from the tropical marine invertebrate, *Ecteinascidia turbinata,* and designated therein as ecteinascidins, and the use of such compositions as antibacterial, anti-viral, and/or antitumor agents in mammals.

U.S. Pat. No. 5,089,273, which describes novel compositions of matter extracted from the tropical marine invertebrate, *Ecteinascidia turbinata,* and designated therein as ecteinascidins 729, 743, 745, 759A, 759B and 770. These compounds are useful as antibacterial and/or antitumor agents in mammals.

U.S. Pat. No. 5,478,932, which describes ecteinascidins isolated from the Caribbean tunicate *Ecteinascidia turbinata,* which provide in vivo protection against P388 lymphoma, B16 melanoma, M5076 ovarian sarcoma, Lewis lung carcinoma, and the LX-1 human lung and MX-1 human mammary carcinoma zenografts.

U.S. Pat. No. 5,654,426, which describes several ecteinascidins isolated from the Caribbean tunicate *Ecteinascidia turbinata,* which provide in vivo protection against P388 lymphoma, B16 melanoma, M5076 ovarian sarcoma, Lewis lung carcinoma, and the LX-1 human lung and MX-1 human mammary carcinoma zenografts.

See also: Corey, E. J., *J. Am. Chem. Soc.,* 1996, 118 pp. 9202–9203; Rinehart, et al., *Journal of National Products,* 1990, "Bioactive Compounds from Aquatic and Terrestrial Sources", vol. 53, pp. 771–792; Rinehart et al., *Pure and Appl. Chem.,* 1990, "Biologically active natural products", vol. 62, pp. 1277–1280; Rinehart, et al., *J. Org. Chem.,*

1990, "Ecteinascidins 729, 743, 745, 759A, 759B, and 770: Potent Antitumor Agents from the Caribbean Tunicate *Ecteinascidia turbinata*", vol. 55, pp. 4512–4515; Wright et al., *J. Org. Chem.,* 1990, "Antitumor Tetrahydroisoquinoline Alkaloids from the Colonial Ascidian *Ecteinascidia turbinata*", *vol.* 55, pp. 4508–4512; Sakai et al., *Proc. Natl. Acad. Sci. USA* 1992, "Additional antitumor ecteinascidins from a Caribbean tunicate: Crystal structures and activities in vivo", vol. 89, 11456–11460; *Science* 1994, "Chemical Prospectors Scour the Seas for Promising Drugs", vol. 266, pp. 1324; Koenig, K. E., "Asymmetric Synthesis," ed. Morrison, Academic Press, Inc., Orlando, Fla., vol. 5, 1985, p. 71; Barton, et al., *J. Chem Soc. Perkin Trans.,* 1, 1982, "Synthesis and Properties of a Series of Sterically Hindered Guandidine Bases", pp. 2085; Fukuyama et al., *J. Am Chem Soc.,* 1982, "Stereocontrolled Total Synthesis of (+)-Saframycin B", vol. 104, pp. 4957; Fukuyama et al., *J. Am Chem Soc.,* 1990, "Total Synthesis of (+)-Saframycin A", vol. 112, p. 3712; Saito, et al., *J. Org. Chem.,* 1989, "Synthesis of Saframycins. Preparation of a Key Tricyclic Lactam Intermediate to Saframycin A", vol. 54, 5391; Still, et al., *J. Org. Chem.,* 1978, "Rapid Chromatographic Technique for Preparative Separations with Moderate Resolution", vol. 43, p. 2923; Kofron, W. G.; Baclawski, L. M., *J. Org. Chem.,* 1976, vol. 41, 1879; Guan et al., *J. Biomolec. Struc. & Dynam.*, vol. 10 pp. 793–817 (1993); Shamma et al., "Carbon-13 NMR Shift Assignments of Amines and Alkaloids," p. 206 (1979); Lown et al., *Biochemistry,* 21, 419–428 (1982); Zmijewski et al., *Chem. Biol. Interactions,* 52, 361–375 (1985); Ito, *CRC Crit. Rev. Anal. Chem.,* 17, 65–143 (1986); Rinehart et al., "Topics in Pharmaceutical Sciences 1989" pp. 613–626, D. D. Breimer, D. J. A. Cromwelin, K. K. Midha, Eds., Amsterdam Medical Press B.V., Noordwijk, The Netherlands (1989); Rinehart et al., "Biological Mass Spectrometry," 233–258 eds. Burlingame et al., Elsevier Amsterdam (1990); Guan et al., *Jour. Biomolec. Struc & Dynam.,* vol. 10 pp. 793–817 (1993); Nakagawa et al., *J. Amer. Chem. Soc.,* 111: 2721–2722 (1989); Lichter et al., "Food and Drugs from the Sea Proceedings" (1972), Marine Technology Society, Washington, D.C. 1973, 117–127; Sakai et al., *J. Amer. Chem. Soc.,* 1996, 118, 9017; Garcia—Rocha et al., *Brit. J. Cancer,* 1996, 73: 875–883; and Pommier et al., *Biochemistry,* 1996, 35: 13303–13309.

The disclosures of the above-referenced patents and publications are hereby incorporated herein by reference.

Et 743 (NSC 648766) is currently undergoing evaluation by the National Cancer Institute on the basis of exceedingly potent activity in vivo against a variety of tumors.

Et 743

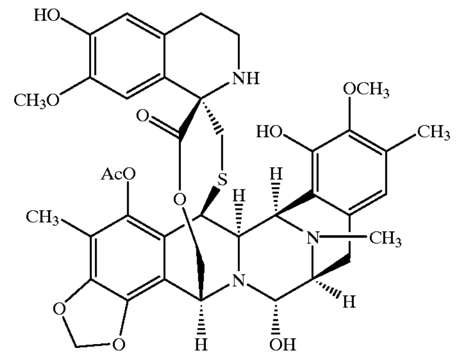

In 1996, the total synthesis of Et-743 was reported. See E. J. Corey et al., *J. Amer. Chem. Soc.,* 118, 9292–9203 (1996);

see also, U.S. Pat. No. 5,721,362. Disclosed in the '362 patent is the intermediate 11, with the following structure:

Compound 11

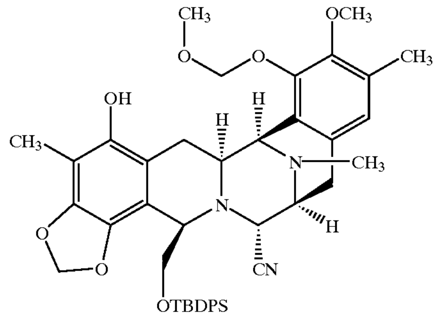

This intermediate compound, re-designated herein as Compound 1, has served as the starting material for a series of new synthetic ecteinascidin-like compounds.

SUMMARY OF THE INVENTION

The present invention is directed to compounds having the following formula:

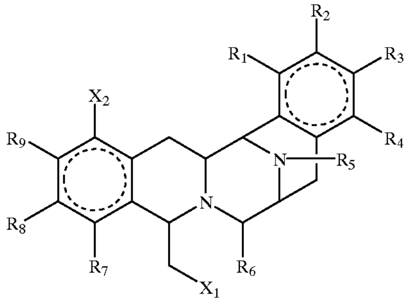

wherein the substituent groups defined by $R_1$, $R_2$, $R_3$, $R_4$, $R_5$, $R_6$, $R_7$, $R_8$ and $R_9$ are each independently selected from the group consisting of H, OH, OR', SH, SR', SOR', $SO_2R'$, $NO_2$, $NH_2$, NHR', $N(R')_2$, NHC(O)R', CN, halogen, =O, C(=O)H, C(=O)R', $CO_2H$, $CO_2R'$, $C_1$–$C_{12}$ alkyl, $C_2$–$C_{12}$ alkenyl, $C_2$–$C_{12}$ alkynyl, substituted or unsubstituted aryl, substituted or unsubstituted aralkyl, and substituted or unsubstituted heteroaromatic;

wherein each of the R' groups is independently selected from the group consisting of H, OH, $NO_2$, $NH_2$, SH, CN, halogen, =O, C(=O)H, C(=O)$CH_3$, $CO_2H$, $CO_2CH_3$, $C_1$–$C_{12}$ alkyl, $C_2$–$C_{12}$ alkenyl, $C_2$–$C_{12}$ alkynyl, aryl, aralkyl, and heteroaromatic;

wherein each dotted circle represents one, two or three optional double bonds;

wherein $R_7$ and $R_8$ may be joined into a carbocyclic or heterocyclic ring system;

and wherein $X_1$ and $X_2$ are each independently defined as above for $R_1$–$R_8$ and further include the definitions of $X_1$ and $X_2$ as provided below for the preferred embodiments.

Preferred compounds of the present invention have the following formula:

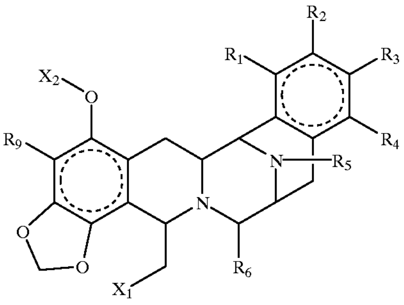

wherein the substituent groups defined by $R_1$, $R_2$, $R_3$, $R_4$, $R_5$, $R_6$, and $R_9$ are each independently selected from the group consisting of H, OH, OR', SH, SR', SOR', $SO_2R'$, $NO_2$, $NH_2$, NHR', $N(R')_2$, NHC(O)R', CN, halogen, =O, $C_1$–$C_6$ alkyl, substituted or unsubstituted aryl, substituted or unsubstituted aralkyl, and substituted or unsubstituted heteroaromatic;

wherein each of the R' groups is independently selected from the group consisting of H, OH, $NO_2$, $NH_2$, SH, CN, halogen, =O, C(=O)H, C(=O)$CH_3$, $CO_2H$, $CO_2CH_3$, $C_1$–$C_6$ alkyl, phenyl, benzyl, and heteroaromatic;

wherein each dotted circle represents one, two or three optional double bonds;

and wherein $X_1$ and $X_2$ are each independently defined as above for $R_1$–$R_8$, and further include the definitions of $X_1$ and $X_2$ as provided below for the preferred embodiments.

Suitable halogen substituents in the compounds of the present invention include F, Cl, Br and I.

Alkyl groups preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more preferably 1, 2, 3 or 4 carbon atoms. The terms alkenyl and alkynyl as used herein refer to both cyclic and noncyclic groups, although straight or branched noncyclic groups are generally more preferred.

Preferred alkoxy groups in the compounds of the present invention include groups having one or more oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Preferred alkylthio groups in the compounds of the present invention have one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred.

Preferred alkylsulfinyl groups in the compounds of the present invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred.

Preferred alkylsulfonyl groups in the compounds of the present invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred.

Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties.

Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolindinyl groups.

Suitable carbocyclic aryl groups in the compounds of the present invention include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including substituted phenyl, such as 2-substituted phenyl, 3-substituted phenyl, 2,3-substituted phenyl, 2,5-substituted phenyl, 2,3,5-substituted and 2,4,5-substituted phenyl, including where one or more of the phenyl substituents is an electron-withdrawing group such as halogen, cyano, nitro, alkanoyl, sulfinyl, sulfonyl and the like; naphthyl including 1-naphthyl and 2-naphthyl; biphenyl; phenanthryl; and anthracyl.

References herein to substituted R' groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a $C_1$–$_6$ alkanoyl group such as acyl and the like; carboxamido; allyl groups including those groups having 1 to about 12 carbon atoms or from 1 to about 6 carbon atoms and more preferably 1–3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl (e.g., R being a substituted or unsubstituted biphenyl moiety); and aralkyl such as benzyl.

The compounds of the present invention can be prepared synthetically from the intermediate compound 11 described in the '362 patent. Numerous active antitumor compounds have been prepared from this compound and it is believed that many more compounds may be formed in accordance with the teachings of the present disclosure.

One especially preferred embodiment of the present invention is the novel ecteinascidin-like compounds that have been prepared from Compound 1:

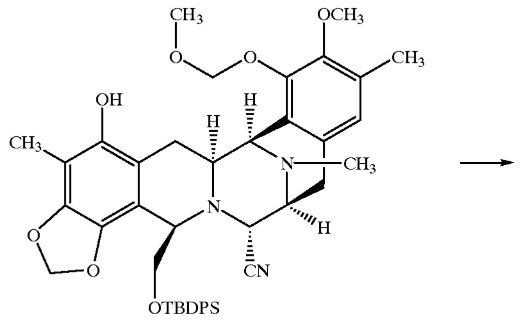

Compound 1

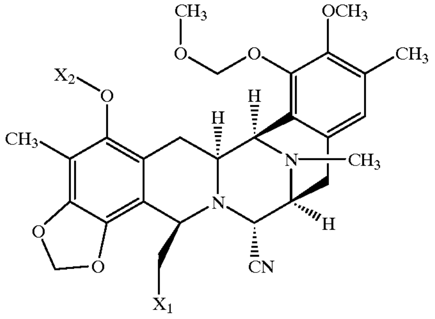

New Compounds wherein $X_1$ and $X_2$ are each independently selected from the group consisting of:

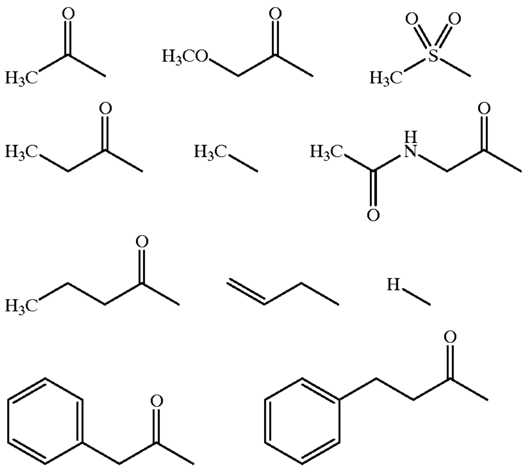

-continued

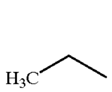 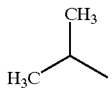 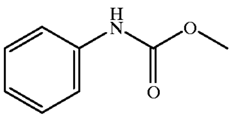

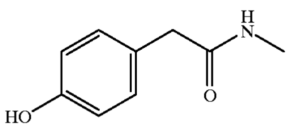 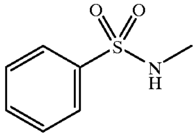

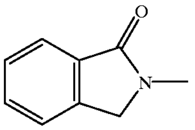 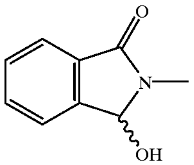

or the formula:

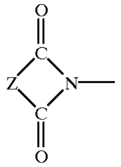

wherein Z is selected from the group consisting of:

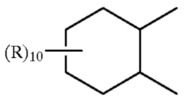 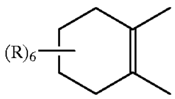 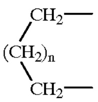

where n=1, 2, 3, . . . 20

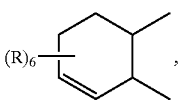, 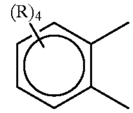

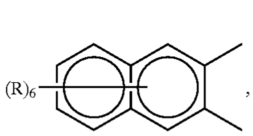, 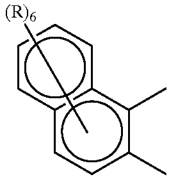

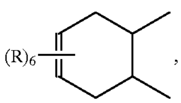, 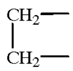 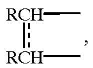,

-continued

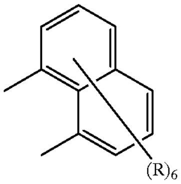 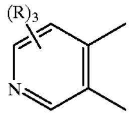 and

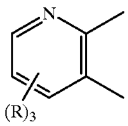

wherein each R group, which may be the same or be different, is selected from the group consisting of H, OH, SH, $NH_2$, $NO_2$, CN, $NH(C{=}O)CH_3$, $O(C{=}O)CH_3$, halogen, $C_1$–$C_6$-alkyl, $C_1$–$C_6$-alkoxy, $C_1$–$C_6$-acyl, aryl or alkylaryl.

Another especially preferred embodiment of the present invention is pharmaceutical compositions useful as antitumor agents, comprising an effective antitumor amount of one or more of the compounds of the present invention and a pharmaceutically acceptable diluent, carrier or excipient.

Yet another especially preferred embodiment of the present invention is the synthetic intermediates of the compounds of the present invention as described in detail below.

Finally, the present invention includes the synthetic processes described herein.

DETAILED DESCRIPTION OF THE PREFERRED EMBODIMENTS

The currently most preferred compound of the present invention is the compound of formula 7:

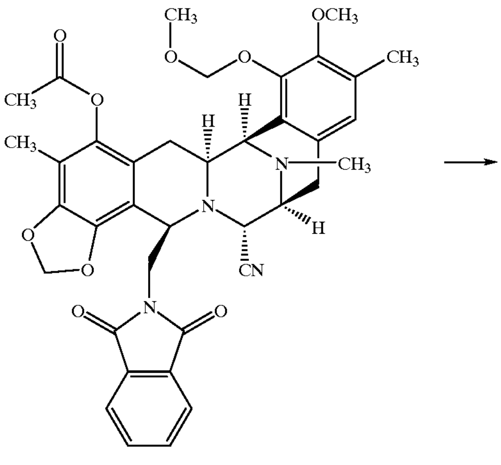

6

-continued
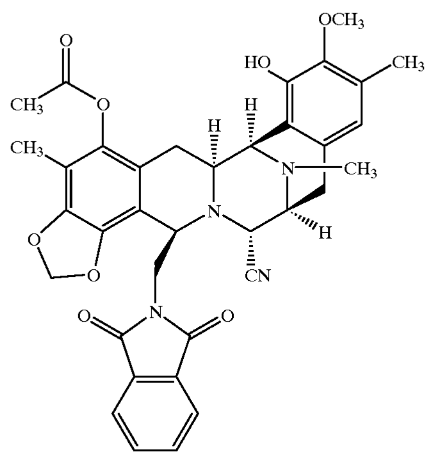
7 (94%)
The preferred method of producing the compound of formula 7 is set forth below in Scheme I:
Scheme I
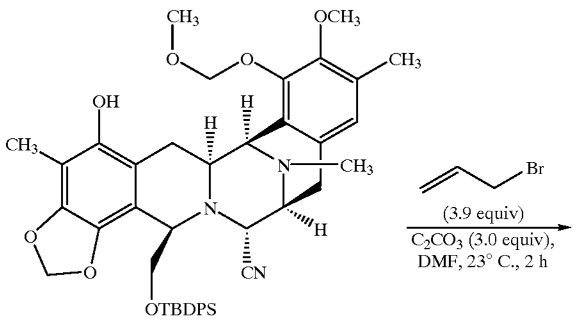
1
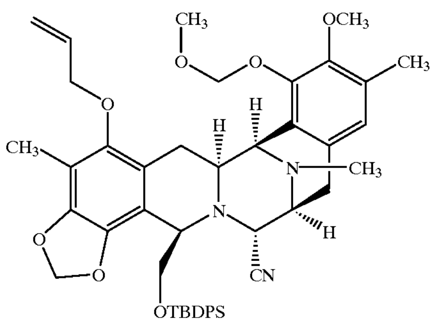
2 (93%)
-continued
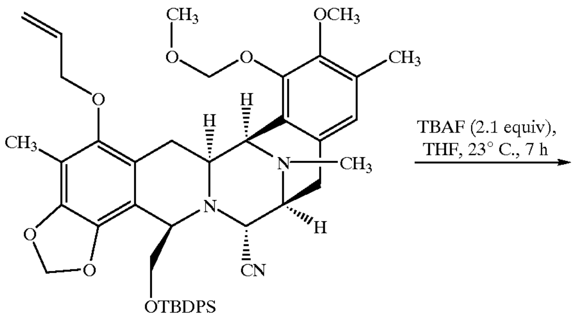
2
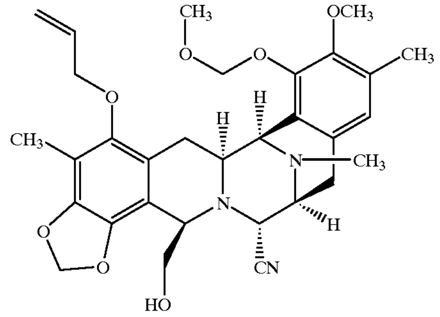
3 (99%)
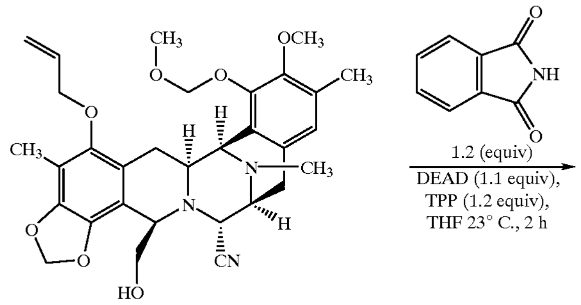
3
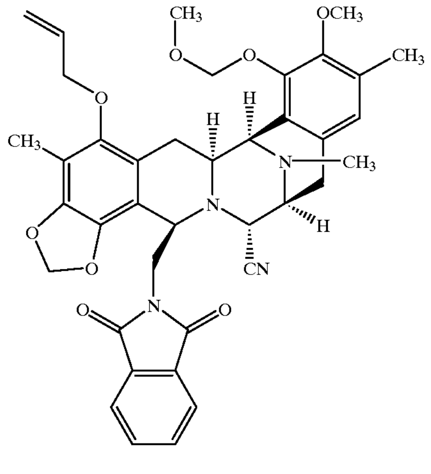
4 (91%)

-continued
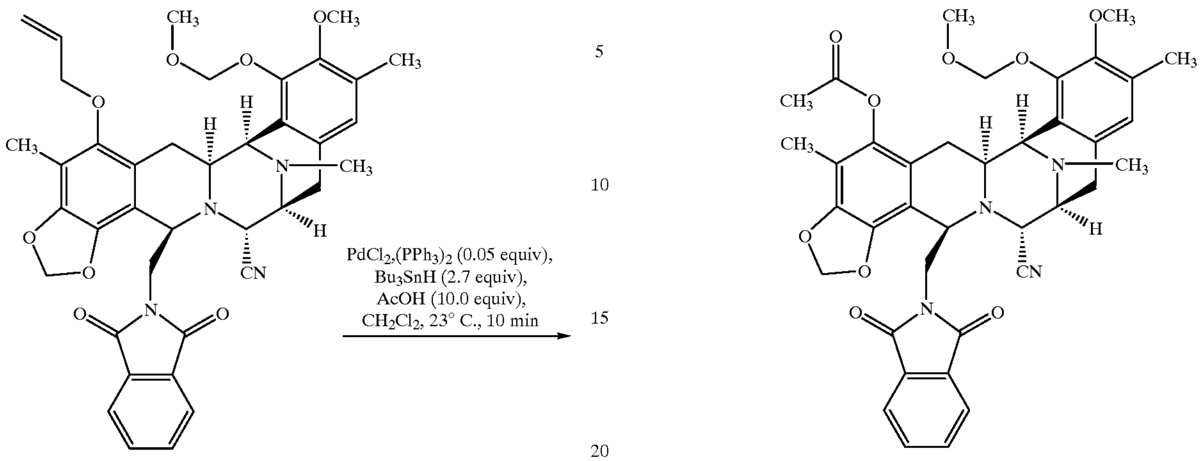
4
6 (94%)
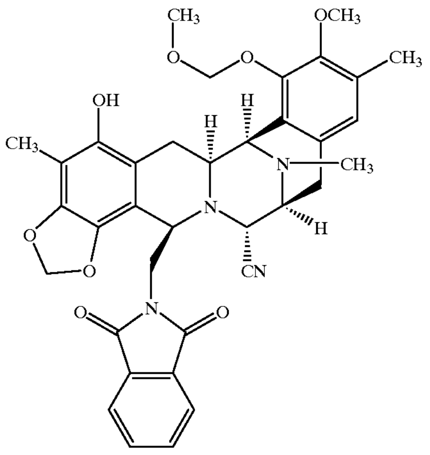
5 (97%)
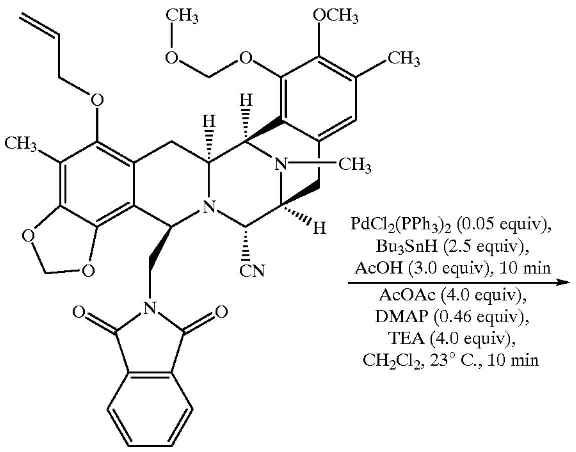
4
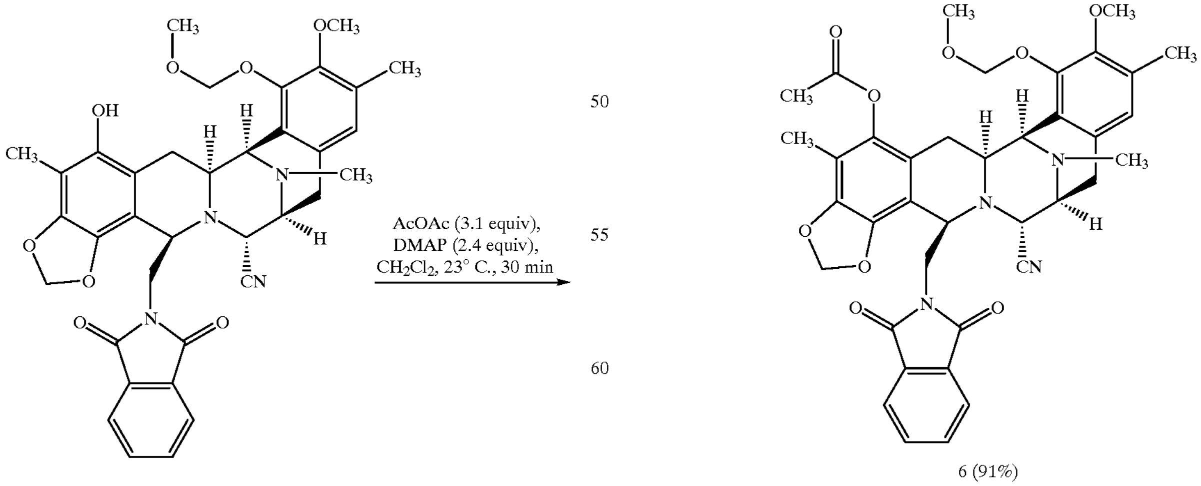
5
6 (91%)

-continued

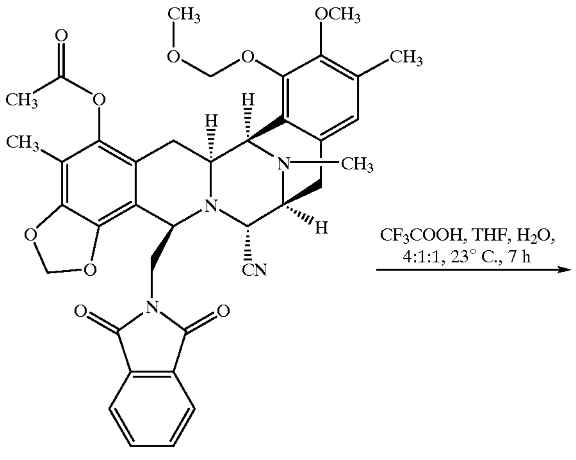

6

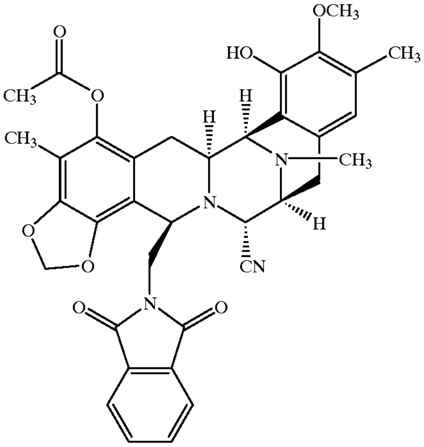

7 (94%)

As illustrated in Scheme I, the first step for producing the preferred compound 7 of the present invention is the high yield conversion (93%) of the phenol compound 1 to the allyl ether compound 2. The second step is the high yield (99%) removal of the TBDPS protecting group to form the free alcohol compound 3. The third step in this process is the high yield (91%) coupling of phthalimide to the free alcohol compound 3 to yield the phthalimide derivative, compound 4. The phthalimide compound 4 is then converted in high yield (97%) to the phenol compound 5. Phenol compound 5 is converted in high yield (94%) to the methoxymethyl ether compound 6. Alternatively, the phthalimide compound 4 can be treated with several reagents to produce in high yield (91%) the methoxymethyl ether compound 6. The methoxymethyl ether compound 6 is finally reacted with trifluoroacetic acid to provide the desired compound 7, in high yield (94%). The overall yield of this process is about 72%.

The Scheme I method can be modified for the preparation of a preferred group of compounds. This modification is shown below in Scheme II:

Scheme II

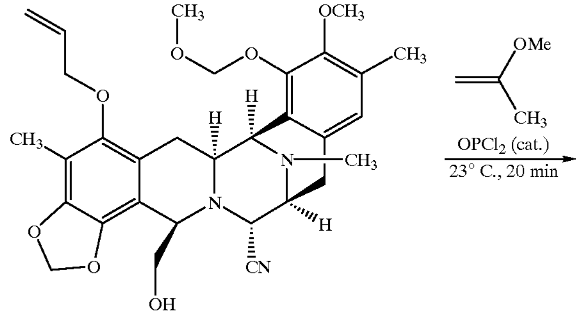

3

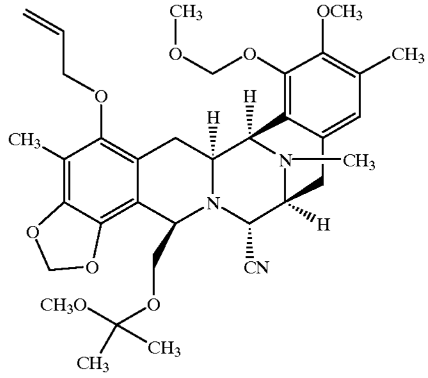

8 (99%)

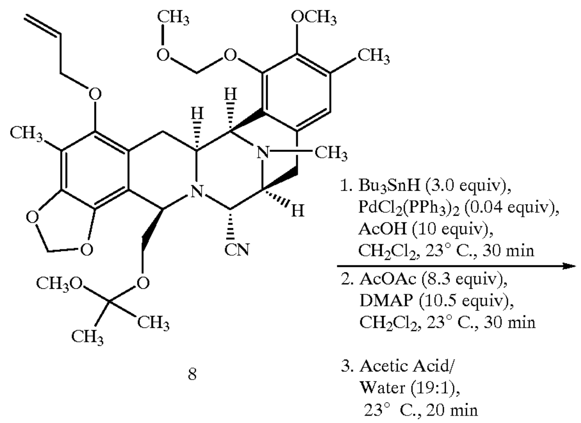

8

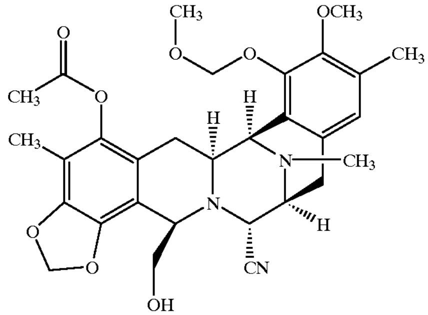

9 (89% yield over 3 steps)

-continued

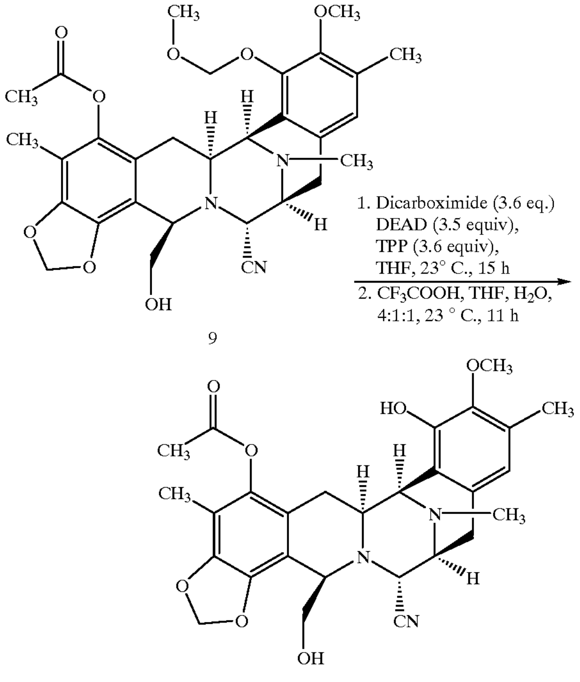

9

10–19

In Scheme II, the free alcohol compound 3 is protected by reaction with 2-methoxypropene to yield the allyl ether compound 8 in high yield (99%). Compound 8 is then converted into the intermediate alcohol 9 in three steps with an overall yield of 89%. Compound 9 can be reacted with a wide variety of phthalimides, dicarboximides, or equivalents thereof (e.g., amides, including aromatic amides, ureas, urethanes, sulfonamides, alkoxy compounds, urethanes, and the like) to form compounds of the formula:

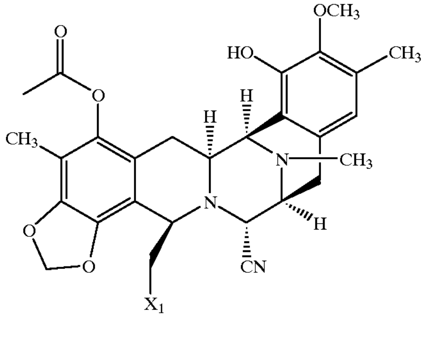

wherein $X_1$ is the radical provided by the phthalimide, dicarboximide or equivalent compound. Especially preferred compounds prepared by the Scheme II process include the compounds wherein $X_1$ has the formula:

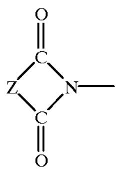

and wherein Z is selected from the group consisting of:

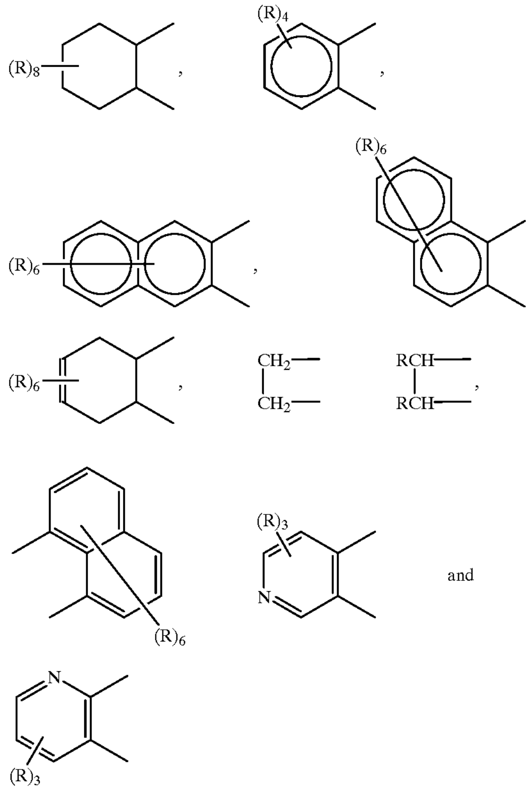

, , , , and wherein each R group, which may be the same or be different, is selected from the group consisting of hydrogen, amino, halogen, nitro, $C_1$–$C_6$-alkyl, $C_1$–$C_6$-alkoxy, $C_1$–$C_6$-acyl, aryl, especially phenyl or alkylaryl, especially benzyl.

In yet another preferred modification, the phenol compound 5 may be transformed into a number of derivatives, as shown in Scheme III:

Scheme III

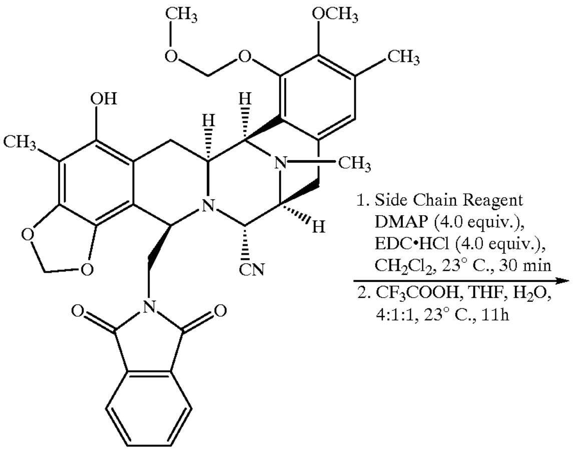

5

-continued

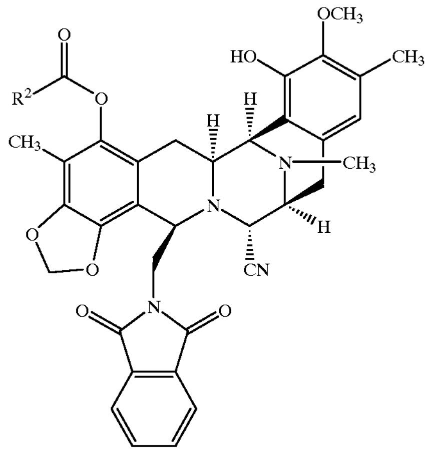

35-39

As shown in Scheme III, the phenol compound (5) is reacted with various side-chain modifying carboxylic acids to afford the corresponding phenolic esters. Scheme III can be used to produce numerous compounds having the formula:

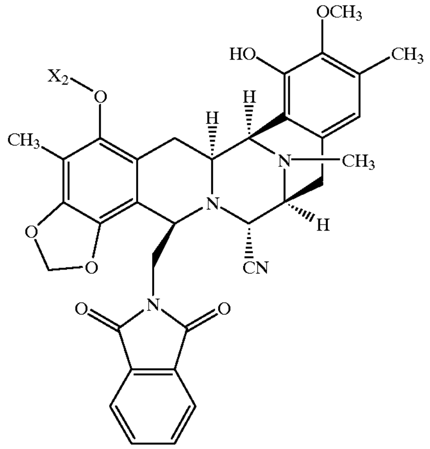

wherein $X_2$ is the radical provided by the carboxylic acid. Especially preferred $X_2$ groups are selected from the group consisting of:

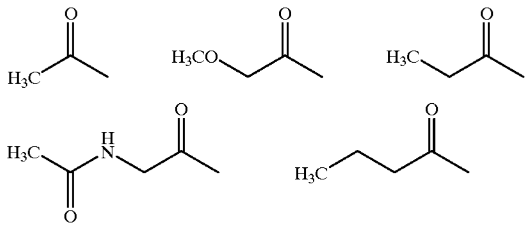

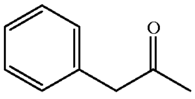

and

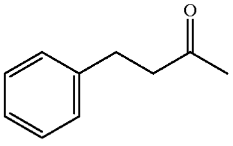

Another modification is the alkylation reaction illustrated in Scheme IV:

Scheme IV

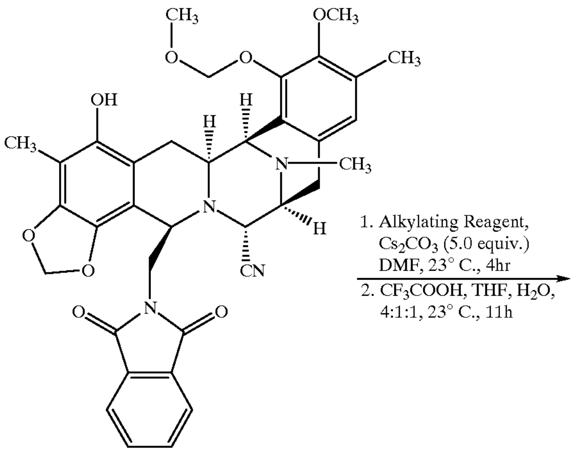

5

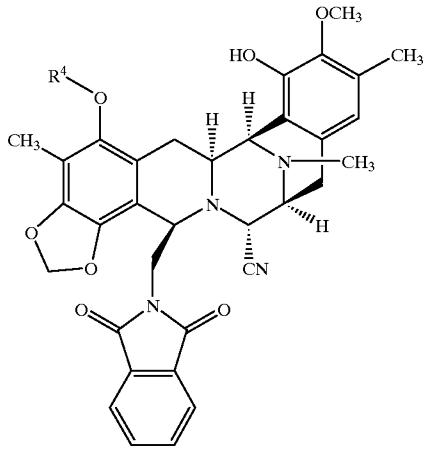

40-42

In Scheme IV, the phenol compound 5 is treated with an alkylating agent to afford the corresponding $R^4$ derivatives. Scheme IV can be used to produce numerous compounds having the formula:

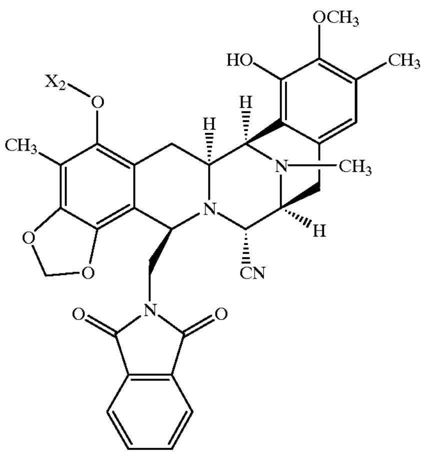

wherein $X_2$ is the radical provided by the alkylating agent. Representative derivatives of this type include the compounds wherein $X_2$ is selected from the group consisting of:

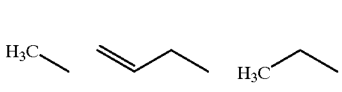

and

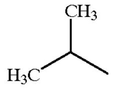

Several key intermediate compounds include the tosylate 29, the azide compound 30, and the free amine compound 31. The reaction sequence for these compounds is shown below in Scheme V:

Scheme V

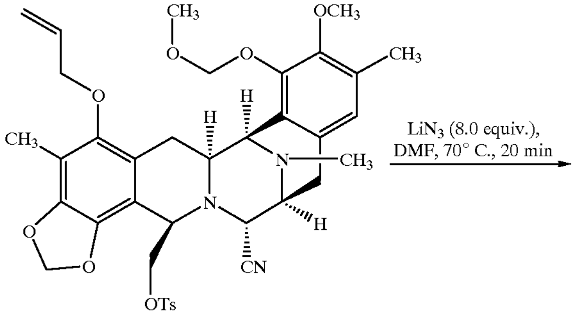

29

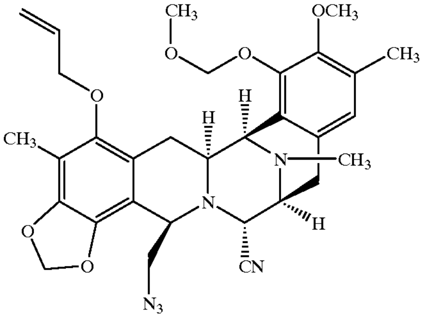

30 (73%)

-continued

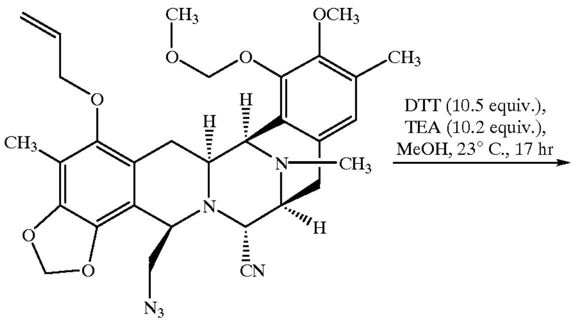

30

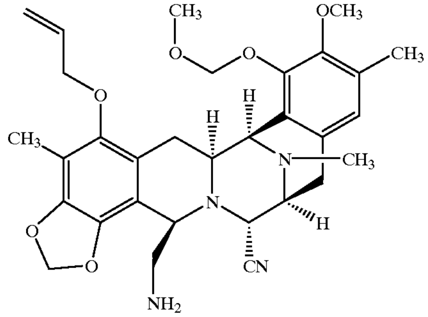

31 (59%)

The following additional compounds of the present invention (including for example, Compounds 43, 44, 45, 46, 47, 48, 49, 50, 51, 54, 55 and 56) have been prepared as described in detail in the Examples infra:

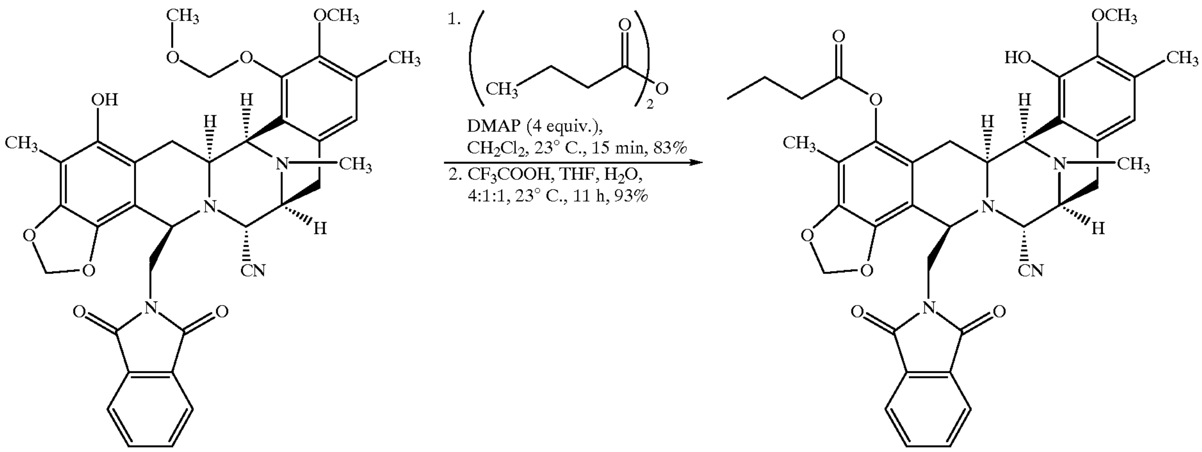

5

43

-continued
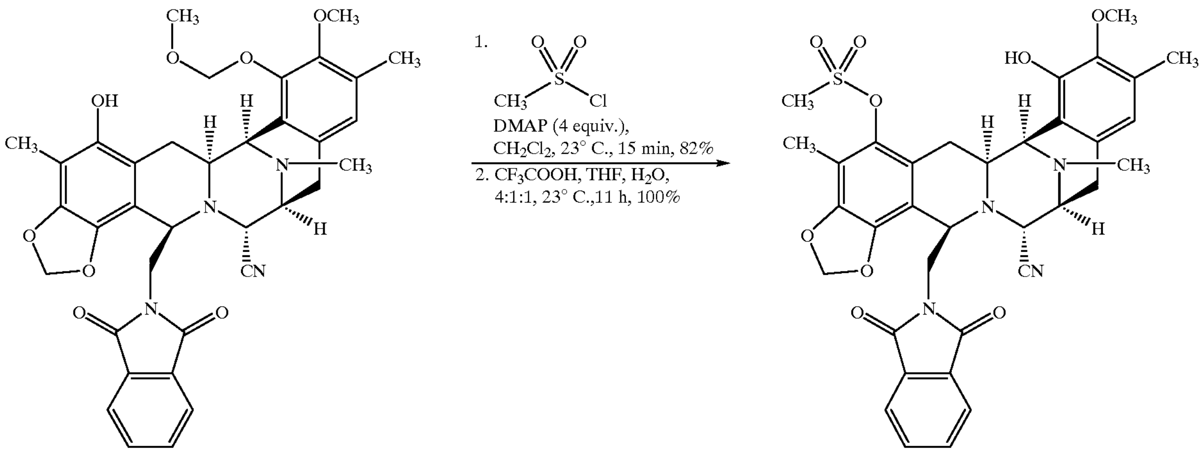
5 44
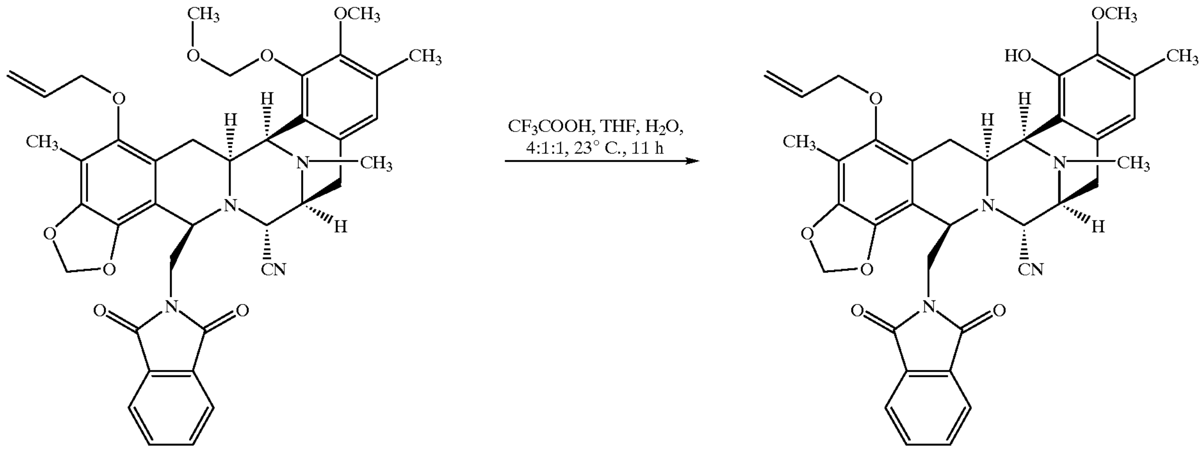
4 45 (85%)
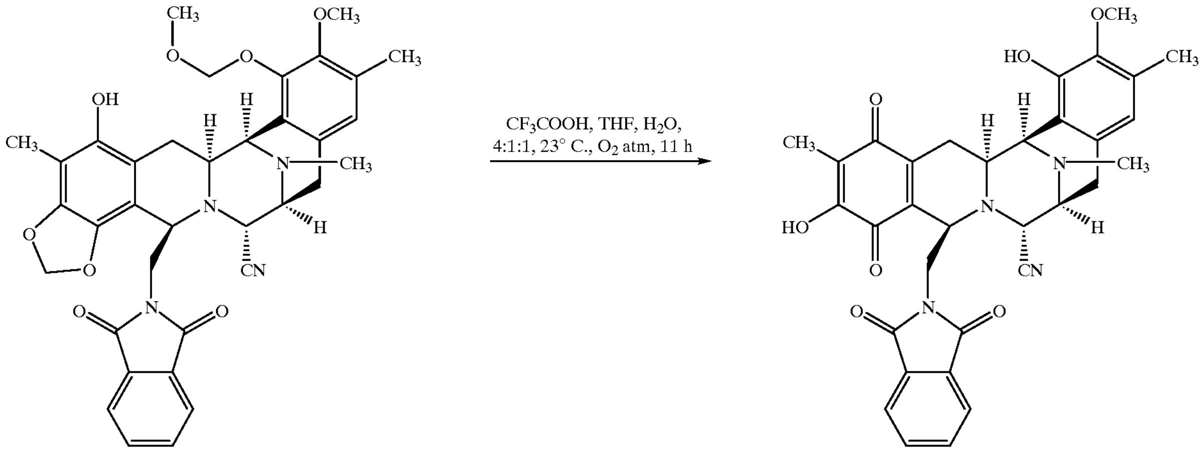
5 46 (50%)

-continued
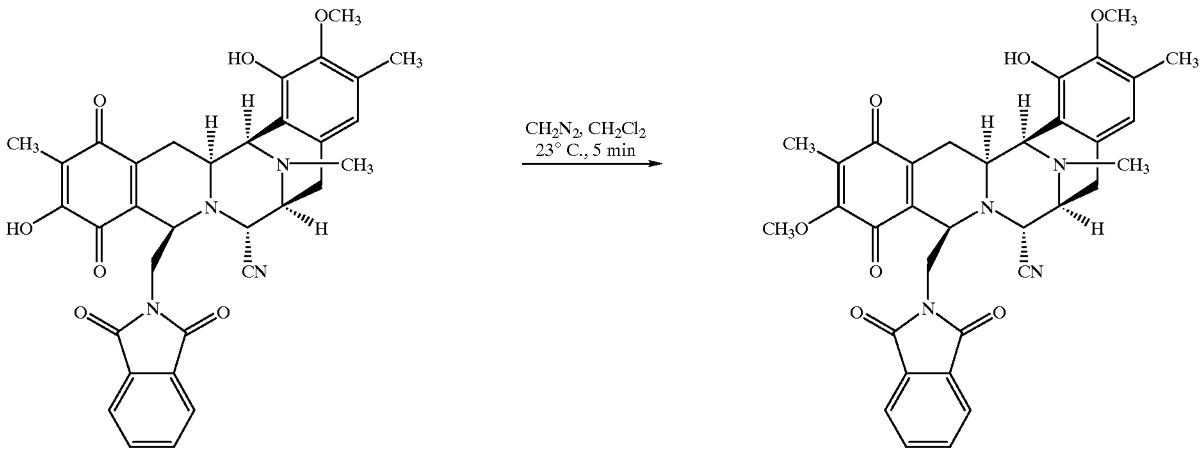
46
47 (42%)
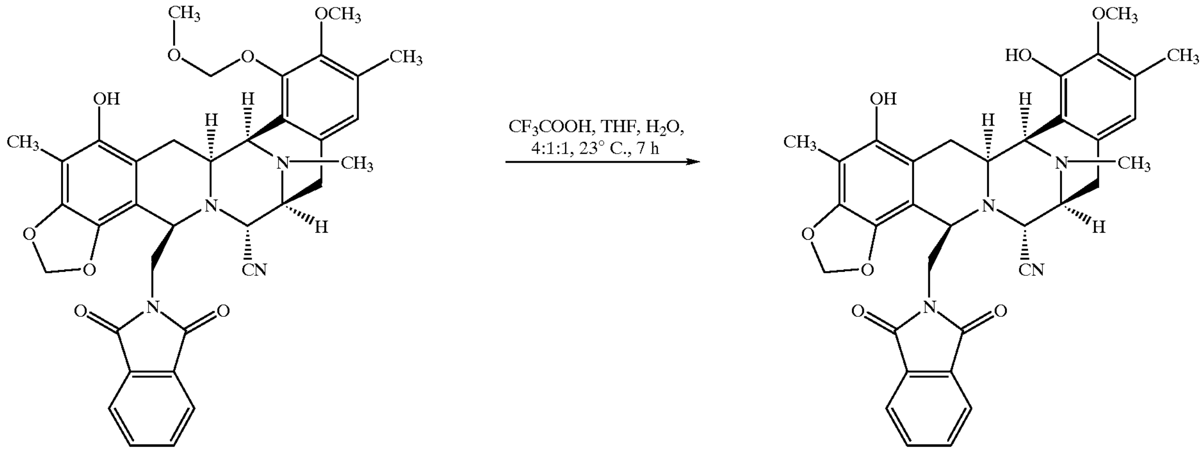
5
48 (71%)
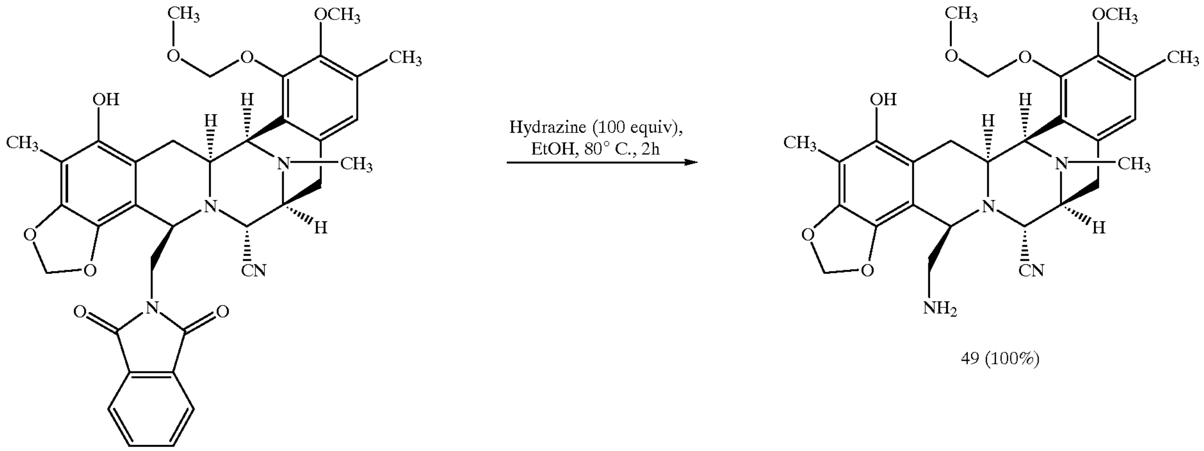
49 (100%)
5

-continued
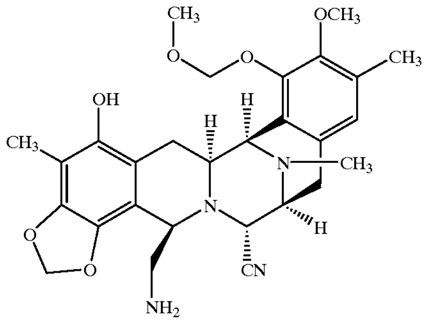
49
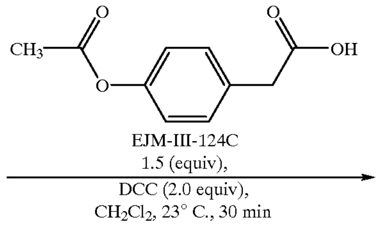
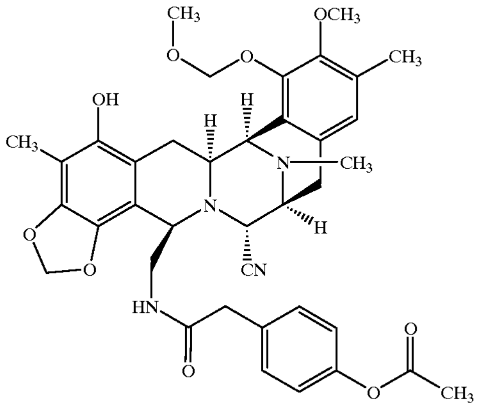
50 (50%)
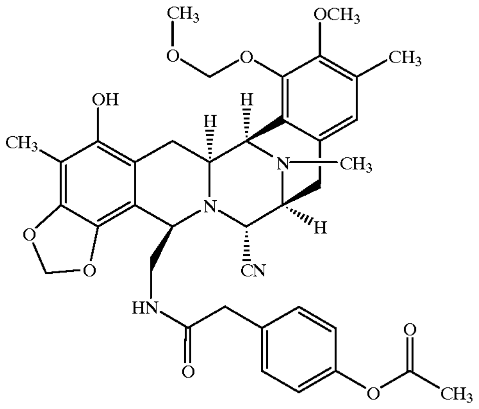
50
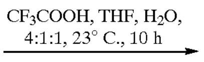
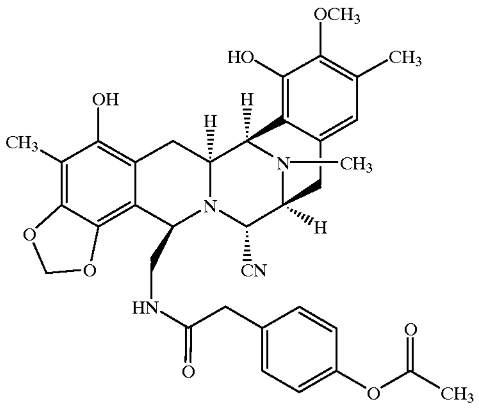
51 (42%)
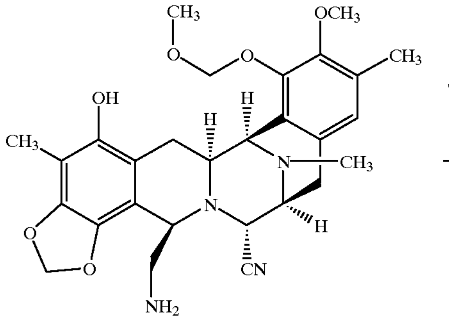
49
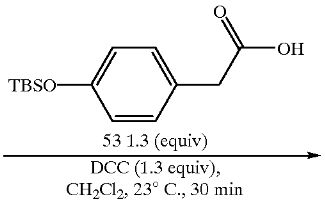
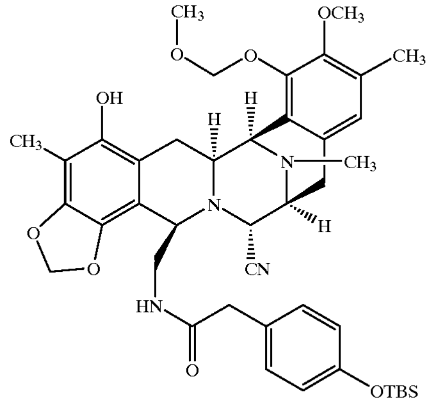
54 (47%)

-continued

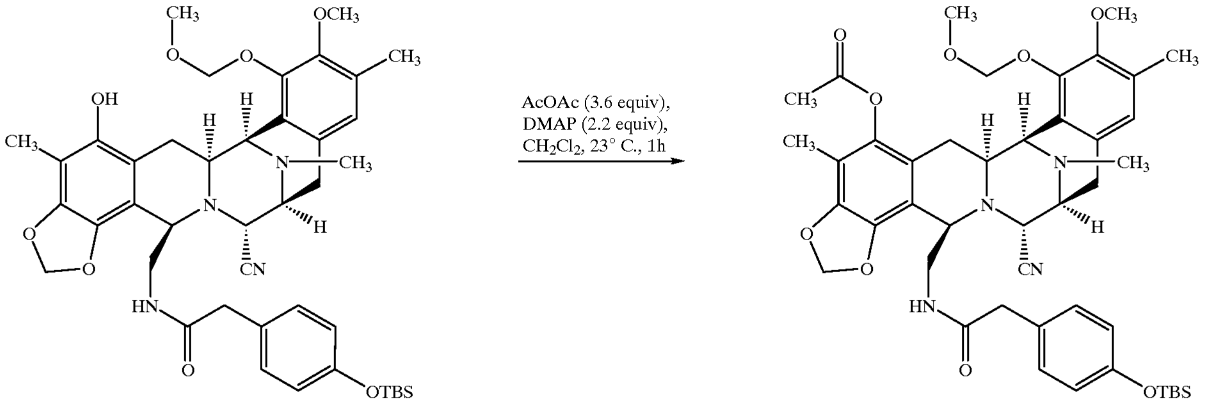

54

55 (100%)

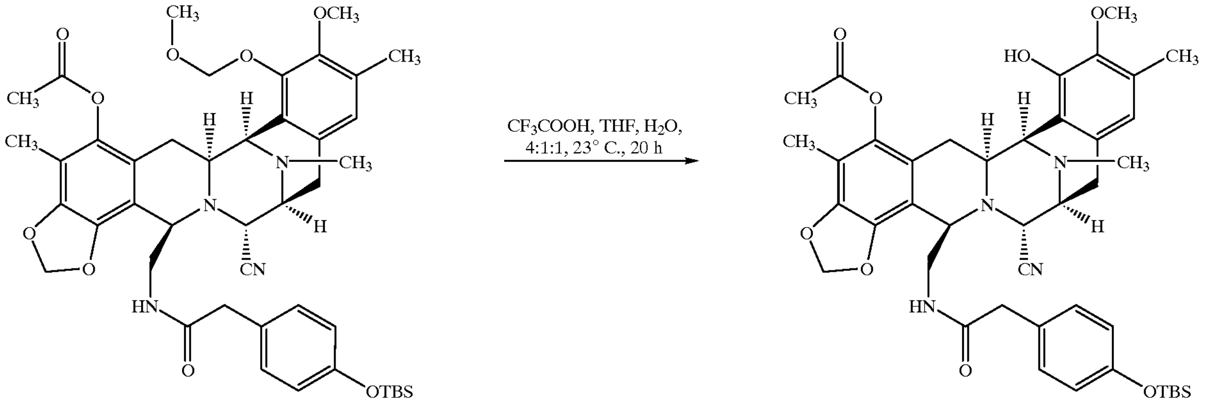

55

56 (44%)

As the skilled artisan will readily appreciate, the reaction schemes described herein may be modified and/or combined in various ways, and the compounds generated therefrom are to be considered as being part of this invention.

The present invention will be further illustrated with reference to the following examples which aid in the understanding, but which are not to be construed as limitations thereof. All percentages reported herein, unless otherwise specified, are percent by weight. All temperatures are expressed in degrees Celsius.

EXAMPLE 1

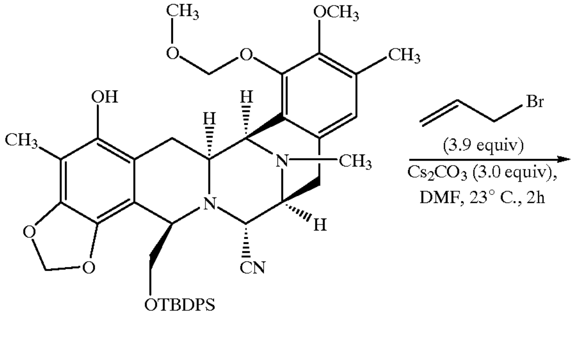

1

-continued

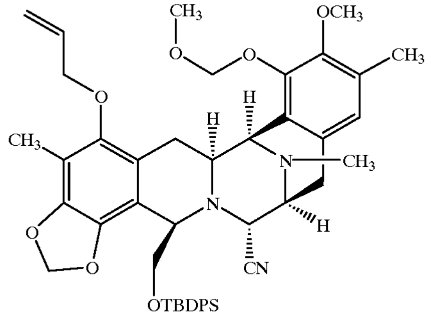

2 (93%)

Cesium carbonate (100.0 mg, 0.307 mmol) was gently flame dried and added as a solid to a solution of the phenol (1) (79.0 mg, 0.104 mmol) in DMF (5.5 mL). Allyl bromide (35.0 $\mu$L, 0.405 mmol) was then charged into the solution and the reaction was stirred at 23° C. for 2 h. The reaction was diluted with 1:1 ethyl acetate-hexane (100 mL), washed with water (3x100 mL), dried over sodium sulfate, decanted and concentrated in vacuo to afford Compound 2 as a pure clear viscous oil (77.2 mg, 93%). If necessary the material can be purified by flash column chromatography (70 mL silica gel, 1:2 ethyl acetate-hexane). m.p.: 167° (dec.); $R_f$0.57 (1:1 ethyl acetate-hexane); $^1$H NMR (400 MHz, $CDCl_3$) δ7.62–7.58 (m, 2H), 7.46–7.34 (m, 6H), 7.32–7.26 (m, 2H), 6.70 (s, 1H), 6.12 (m, 1H), 5.78 (d, J=1.5 Hz, 1H), 5.64 (d, J=1.5 Hz, 1H), 5.41 (dq, J=17.2, 1.4 Hz, 1H), 5.27 (dd, J=10.4, 1.5 Hz, 1H), 5.13 (dd, J=7.2, 5.9 Hz, 2H), 4.46 (d, J=2.6 Hz, 1H), 4.25 (d, J=1.9 Hz, 1H), 4.21–4.04 (m, 3H), 3.75 (s, 3H), 3.64 (dd, J=9.9, 2.3 Hz, 1H), 3.60 (s, 3H), 3.42–3.36 (m, 2H), 3.30–3.22 (m, 2H), 3.04 (dd, J=17.8, 8.2 Hz, 1H), 2.72 (d, J=17.8 Hz, 1H), 2.33 (s, 3H), 2.26 (s, 3H). 2.11 (s, 3H), 1.94 (dd, J=16.0, 12.2 Hz, 1H), 0.87 (s, 9H); $^{13}C$ NMR (100 MHz, $CDCl_3$) δ148.5, 148.3, 148.2, 144.1, 139.1, 135.7, 135.4, 133.8, 133.1, 132.7, 130.5, 130.4, 129.6, 129.5, 127.6, 127.5, 125.2, 124.3, 121.6, 118.5, 117.5, 113.0, 111.8, 100.9, 99.2, 74.1, 67.7, 61.5, 59.7, 59.0, 57.1, 57.2, 55.4, 41.6, 26.6, 26.5, 25.6, 18.9, 15.8, 9.2; FTIR (neat) 2931 (s br), 2857 (m), 1460 (m), 1447 (m br), 1429 (s), 1158 (m), 1107 (s), 1093 (s), 1022 (m), 999 (m br), 931 (m br) $cm^{-1}$; HRMS (FAB), [m+Na]/z calc'd for $C_{47}H_{55}O_7N_3SiNa$; 824.3707, found 824.3708; $[\alpha]_D^{23}$=+73.1° (c 1.0, methylene chloride).

EXAMPLE 2

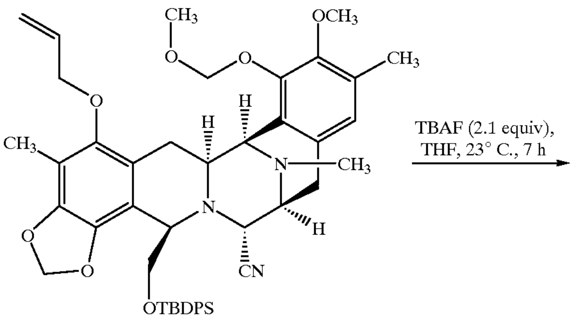

2

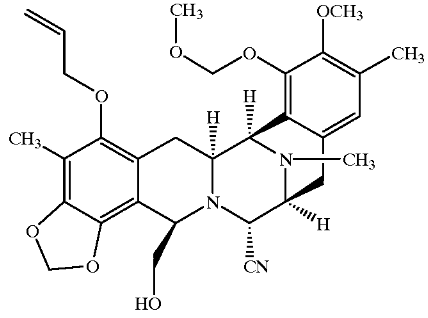

3 (99%)

Compound 2 (77.2 mg, 0.096 mmol) was dissolved in THF (8.0 mL) and a 1.0 M tetrabutylammoniun fluoride solution in THF (200 μL, 0.20 mmol) was added. After stirring at 23° C. for 7 h the reaction was concentrated in vacuo at 23° C. The reaction was diluted into ethyl acetate/hexane (1:1, 100 mL), washed with water (3×100 mL), dried over sodium sulfate, decanted and concentrated in vacuo. The residue was purified by flash column chromatography (30 mL silica gel, gradient 1:3 to 1:1 ethyl acetate-hexane) to afford Compound 3 as a clear film (53.3 mg, 99%). $R_f$0.28 (1:1 ethyl acetate-hexane); $^1H$ NMR (400 MHz, $CDCl_3$) δ6.71 (s, 1H), 6.16–6.06 (m, 1H), 5.92 (d, J=1.4 Hz, 1H), 5.87 (d, J=1.4 Hz, 1H), 5.42 (dq, J=17.1, 1.4 Hz, 1H), 5.28 (dd, J=10.3, 1.3 Hz, 1H), 5.12 (s, 2H), 4.26 (d, J=2.3 Hz, 1H), 4.19 (dd, J=12.1, 5.6 Hz, 1H), 4.14 (dd, J=12.1, 6.3 Hz, 1H), 4.05 (d, J=2.5 Hz, 1H), 3.97 (t, J=3.1 Hz, 1H), 3.70 (s, 3H), 3.65 (dt, J=11.4, 2.4 Hz, 1H), 3.58 (s, 3H), 3.46 (dt, J=10.6, 2.6 Hz, 1H), 3.39–3.33 (m, 2H), 3.24 (dd, J=15.8, 2.7 Hz, 1H), 3.12 (dd, J=17.9, 7.9 Hz, 1H), 2.51 (d, J=18.1 Hz, 1H), 2.36 (s, 3H), 2.21 (s, 3H), 2.11 (s, 3H), 1.87–1.68 (m, 2H); $^{13}C$ NMR (100 MHz, $CDCl_3$) δ148.7, 148.6, 148.5, 144.4, 139.0, 133.8, 131.1, 129.5, 125.1, 124.0, 120.8, 117.6, 117.4, 113.3, 112.3, 101.1, 99.2, 74.1, 63.4, 60.0, 59.7, 58.0, 57.7, 57.1, 56.6, 55.3, 41.6, 26.2, 25.7, 15.7, 9.2; FTIR (neat) 3495 (w br), 2934 (m br), 2253 (w), 1448 (m), 1432 (m br), 1340 (m), 1158 (m), 1104 (s br), 1065 (m), 998 (m), 917 (m br) $cm^{-1}$; HRMS (FAB), [m+Na]/z calc'd for $C_{31}H_{37}O_7N_3Na$: 586.2529, found 586.2543; $[\alpha]_D^{23}$=+96.1° (c 1.0, methylene chloride).

EXAMPLE 3

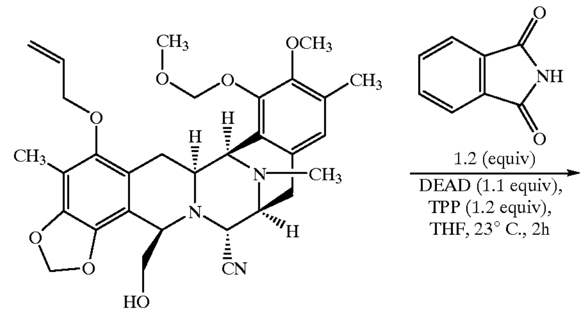

3

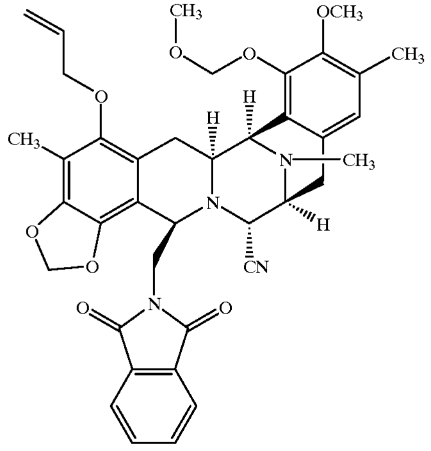

4 (91%)

Alcohol (3) (61.5 mg, 0.109 mmol) and phthalimide (18.8 mg, 0.128 mmol) were azeotropically dried with toluene (2×5 mL) and dissolved in THF (3.8 mL). Triphenylphosphine (35.0 mg, 0.133 mmol) was added followed by diethyl azodicarboxylate (19.0 μL, 0.121 mmol). The reaction turned yellow and then a bright orange color within 5 minutes. After stirring at 23° C. for 2 h the reaction was concentrated in vacuo at 23° C. The residue was purified by flash column chromatography (60 mL silica gel, gradient 2:1 diethyl ether-hexane to 2:3 to 1:1 ethyl acetate-hexane) to afford Compound 4 as a white foam (68.5 mg, 91%). $R_f$0.56 (2:1 ethyl acetate-hexane); $^1H$ NMR (400 MHz, $CDCl_3$) δ7.71–7.65 (m, 4H), 6.63 (s, 1H), 6.08 (m, 1H), 5.61 (d, J=1.5 Hz, 1H), 5.38 (dd, J=17.2, 1.6 Hz, 1H), 5.25–5.23 (m, 2H), 5.07 (dd, J=7.6, 6.0 Hz, 2H), 4.24–4.20 (m, 2H), 4.15–4.13 (m, 3H), 3.61 (d, J=5.6 Hz, 2H), 3.57 (s, 3H), 3.55 (s, 3H), 3.37 (dd, J=8.2, 5.5 Hz, 1H), 3.23 (dd, J=15.4, 2.2 Hz, 1H), 3.18 (dt, J=11.6, 2.6 Hz, 1H), 3.05 (dd, J=18.1, 8.1 Hz, 1H), 2.69 (d, J=18.1 Hz, 1H), 2.31 (s, 3H), 2.19 (s, 3H), 2.10 (s, 3H), 1.69 (dd, J=15.3, 11.6 Hz, 1H); $^{13}C$ NMR (100

MHz, $CDCl_3$) δ167.7, 151.3, 148.7, 148.3, 148.1, 144.2, 139.5, 133.8, 133.5, 131.9, 130.3, 130.2, 125.1, 123.8, 122.9, 121.0, 118.0, 117.5, 113.6, 112.4, 100.8, 99.2, 74.3, 60.3, 59.6, 57.7, 57.5, 56.9, 55.7, 55.5, 41.9, 41.5, 26.6, 25.4, 16.0, 9.4; FTIR (neat) 2935 (m br), 2256 (w), 1773 (m), 1716 (s), 1459 (m br), 1432 (m br), 1343 (m), 1267 (m br), 1233 (m), 1158 (m), 1100 (s), 1064 (m), 1024 (m), 947 (m br) $cm^{-1}$; HRMS (FAB), [m+Na]/z calc'd for $C_{39}H_{40}O_8N_4Na$: 715.2744, found 715.2730; $[\alpha]_D^{23}$=+72.7° (c 1.0, methylene chloride).

EXAMPLE 4

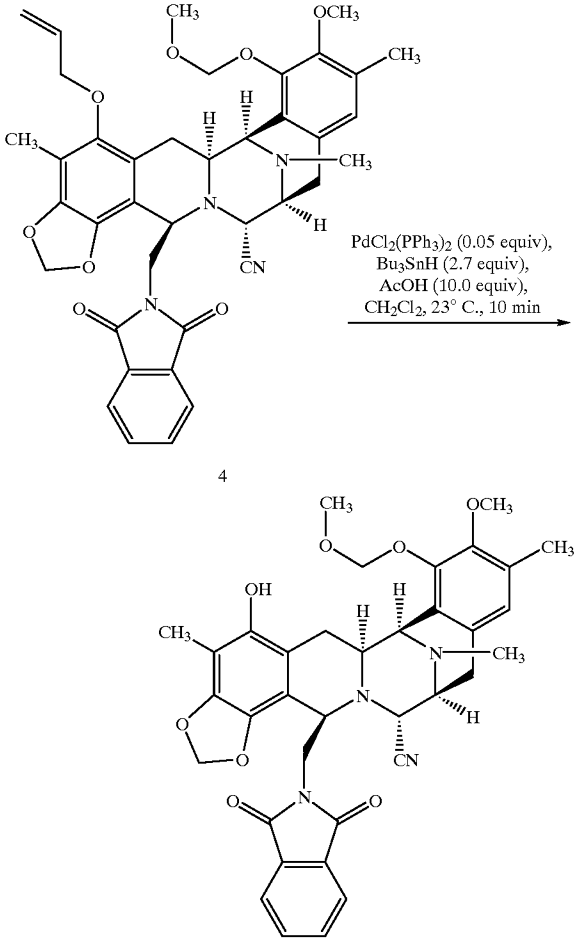

4

5 (97%)

Phthalimide (4) (20.0 mg, 0.0289 mmol) and acetic acid (16.5 μL, 0.289 mmol) were dissolved in methylene chloride (0.8 mL). $PdCl_2(PPh_3)_2$ (1.0 mg, 1.4 μmol) was added followed by tributyltin hydride (21.0 μL, 0.0779 mmol). Bubbling was observed and the reaction changes from a yellow to a dark orange color. After stirring at 23° C. for 10 min the reaction was quenched into water (20 mL), extracted with methylene chloride (2×20 mL), dried over sodium sulfate, decanted and concentrated in vacuo. The residue was purified by flash column chromatography (30 mL silica gel, gradient 1:4 to 1:1 to 2:1 ethyl acetate-hexane) to afford Compound 5 as a white foam (18.3 mg, 97%). $R_f$0.42 (2:1 ethyl acetate-hexane); $^1$H NMR (400 MHz, $CDCl_3$) δ7.75–7.71 (m, 2H), 7.69–7.65 (m, 2H), 6.61 (s, 1H), 5.51 (s, 1H), 5.27 (d, J=6.0 Hz, 1H), 5.23 (br s, 1H), 5.13 (d, J=6.0 Hz, 1H), 5.06 (s, 1H), 4.25 (d, J=2.4 Hz, 1H), 4.21 (d, J=5.0 Hz, 1H), 4.16 (d, J=2.1 Hz, 1H), 3.67 (s, 3H), 3.66 (s, 3H), 3.53 (m, 2H), 3.37 (d, J=7.8 Hz, 1H), 3.22 (d, J=11.5 Hz, 1H), 3.15 (d, J=14.7 Hz, 1H), 3.05 (dd, J=18.0, 8.1 Hz, 1H), 2.65 (d, J=18.0 Hz, 1H), 2.31 (s, 3H), 2.20 (s, 3H), 2.05 (s, 3H), 1.73 (m, 1H); $^{13}$C NMR (100 MHz, $CDCl_3$) δ167.9, 148.7, 147.5, 145.6, 145.5, 144.3, 136.9, 133.6, 132.0, 130.5, 124.9, 123.0, 117.9, 113.1, 112.4, 106.3, 100.5, 99.6, 60.3, 59.8, 57.7, 57.0, 56.7, 55.5, 55.3, 42.4, 41.6, 25.9, 25.4, 15.9, 8.9; FTIR (neat) 3464 (w br), 2936 (w br), 1773 (w), 1715 (s), 1484 (w), 1461 (m), 1433 (m), 1397 (m), 1235 (w), 1157 (w), 1101 (m), 1076 (w), 1060 (w), 1023 (w), 1007 (w), 957 (w) $cm^{-1}$; HRMS (FAB), [m+H]/z calc'd for $C_{36}H_{37}O_8N_4$: 653.2611, found 653.2608; $[\alpha]_D^{23}$=+3.1° (c 0.35, methylene chloride).

EXAMPLE 5

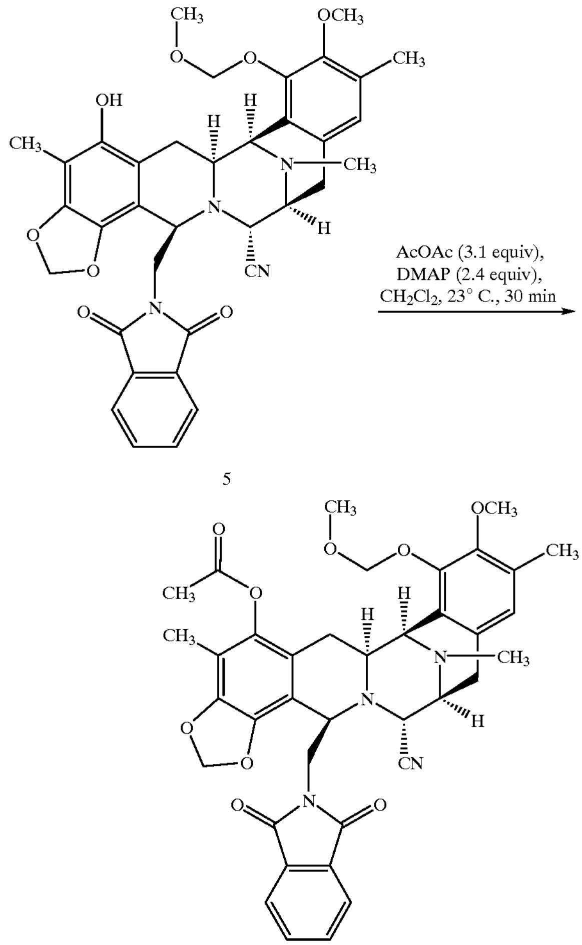

5

6 (94%)

Phenol (5) (1.1 mg, 0.0017 mmol) was dissolved in methylene chloride (0.15 mL). 4-Dimethylaminopyridine (0.5 mg, 0.0041 mmol) and acetic anhydride (0.5 μL, 0.0053 mmol) were added to the solution which was stirred at 23 ° C. for 30 min. The reaction mixture was concentrated in vacuo. The residue was purified by flash column chromatography (0.5 mL silica gel, gradient 1:4 to 1:1 to 2:1 ethyl acetate-hexane) to afford Compound 6 (1.1 mg, 94%). $R_f$0.53 (2:1 ethyl acetate-hexane); $^1$H NMR (400 MHz, $CDCl_3$) δ7.70–7.63 (m, 4H), 6.64 (s, 1H), 5.73 (s, 1H), 5.50 (s, 1H), 5.07 (d, J=5.7 Hz, 1H) 4.98 (d, J=5.7 Hz, 1H), 4.27 (d, J=2.1 Hz, 1H), 4.24 (m, 1H), 4.08 (d, J=2.5 Hz, 1H), 3.74–3.67 (m, 2H), 3.53 (s, 3H), 3.50 (s, 3H), 3.38 (d, J=7.1 Hz, 1H), 3.18 (d, J=11.5 Hz, 1H), 3.02 (dd, J=18.1, 8.1 Hz, 1H), 2.75 (d, J=16.1 Hz, 2H), 2.31 (s, 3H), 2.27 (s, 3H), 2.18 (s, 3H), 2.01 (s, 3H), 1.60 (m, 1H); $^{13}C$ NMR (100 MHz, $CDCl_3$) δ168.3, 167.5, 148.1, 147.8, 144.3, 141.2, 140.5, 133.4, 131.8, 130.2, 125.3, 123.4, 123.0, 120.8, 118.0, 113.6, 111.7, 101.3, 99.1, 59.8, 59.6, 57.7, 56.7, 56.6, 56.1, 55.4, 41.5, 40.9, 26.7, 25.0, 20.1, 16.0, 9.5; FTIR (neat) 2935 (m br), 17641 (m), 1716 (s), 1433 (m br), 1394 (m br), 1369 (m br), 1234 (m), 1198 (s), 1158 (m), 1101 (m br), 1072 (m), 1025 (m), 1000 (m), 947 (m), 933 (m) $cm^{-1}$; HRMS (FAB), [m+H]/z calc'd for $C_{38}H_{39}O_9N_4$: 695.2717, found 695.2744; $[\alpha]_D^{23}$+21.6° (c 1.0, methylene chloride).

EXAMPLE 6

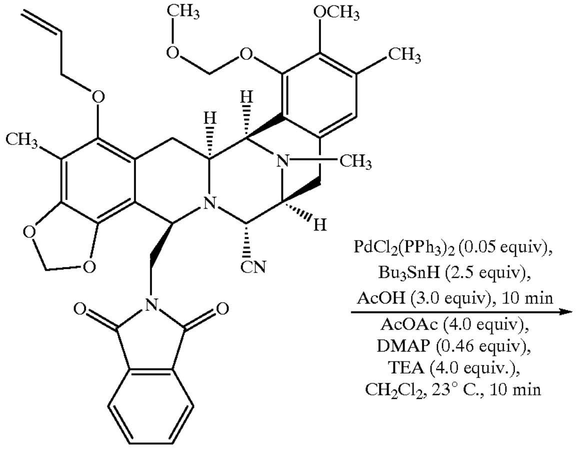

4

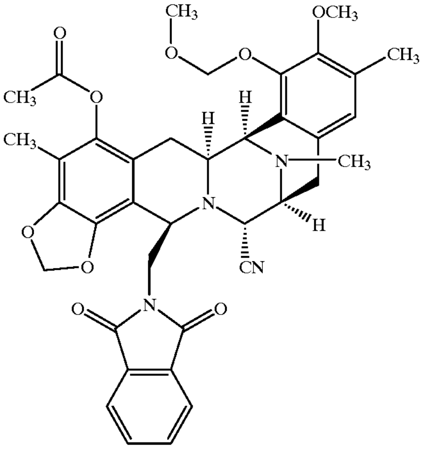

6 (91%)

Alternatively, phthalimide (4) (68.5 mg, 0.99 mmol) and acetic acid (17.0 μL, 0.30 mmol) were dissolved in methylene chloride (6.0 mL). $PdCl_2(PPh_3)_2$ (3.5 mg, 5 μmol) was added followed by tributyltin hydride (67.0 μL, 0.25 mmol). Bubbling was observed and the reaction changes from a yellow to a dark orange color. After stirring at 23° C. for 10 min to the reaction was added triethylamine (55.0 μL, 0.40 mmol), 4-dimethylaminopyridine (5.5 mg, 0.045 mmol) and acetic anhydride (38.0 μL, 0.39 mmol). The reaction was stirred at 23° C. for 10 min and was quenched into quarter-saturated aqueous sodium chloride solution (20 mL), extracted with methylene chloride (3x20 mL), dried over sodium sulfate, decanted and concentrated in vacuo. The residue was purified by flash column chromatography (40 mL silica gel, 1:1 ethyl acetate-hexane) to afford Compound 6 as a white foam (62.8 mg, 91%).

EXAMPLE 7

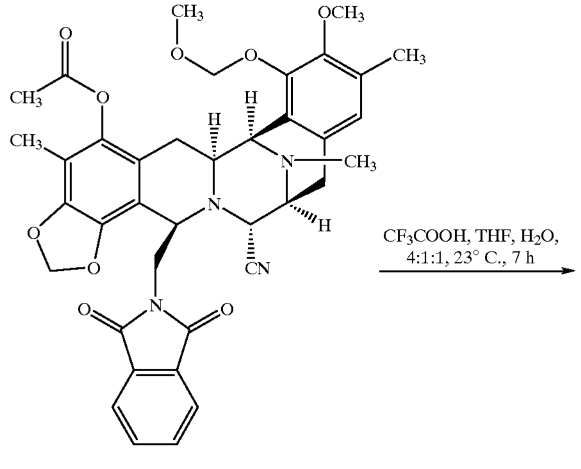

6

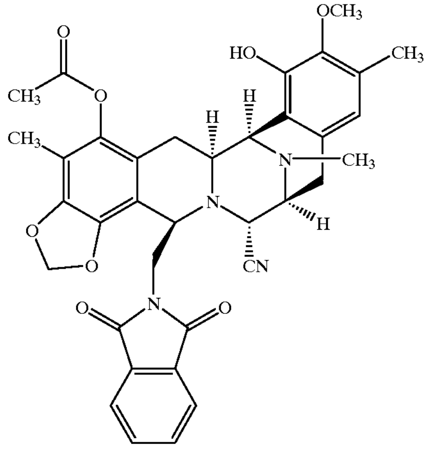

7 (94%)

The methoxymethyl ether (6) (3.8 mg, 0.00547 mmol) was dissolved in a mixture of trifluoroacetic acid-THF-water (4:1:1 (v/v), 4.0 mL) and the solution was stirred at 23° C. for 7 h. The reaction mixture was diluted with toluene (5 mL) and the solution was concentrated in vacuo. Additional volatiles were removed by repetitive in vacuo azeotropic concentration from toluene (3x5 mL). The residue was dissolved in ethyl acetate (10 mL) and washed with a saturated aqueous sodium bicarbonate solution (20 mL), the aqueous layer was extracted with ethyl acetate (2x10 mL) and the combined organic layers were dried over sodium sulfate, decanted and concentrated in vacuo. The residue was purified by flash column chromatography (1.5 mL silica gel, gradient methylene chloride to 2:1 ethyl acetate-hexane) to afford Compound 7 (3.4 mg, 94%). $R_f$0.41 (2:1 ethyl acetate-hexane); $^1H$ NMR (500 MHz, $CDCl_3$) δ7.73–7.71 (m, 2H), 7.67–7.65 (m, 2H), 6.39 (s, 1H), 5.66 (s, 1H), 5.59 (s, 1H), 5.33 (br s, 1H), 4.25–4.23 (m, 2H), 4.02 (d, J=2.5 Hz, 1H), 3.64 (m, 5H), 3.35 (d, J=8.3 Hz, 1H), 3.20 (d, J=12.0 Hz, 1H), 3.02 (dd, J=18.1, 8.1 Hz, 1H), 2.77 (d, J=14.6 Hz, 1H), 2.45 (d, J=18.1 Hz, 1H), 2.29 (s, 6H), 2.22 (s, 3H), 1.99 (s, 3H), 1.73 (t, J=14.3 Hz, 1H); $^{13}C$ NMR (125 MHz, $CDCl_3$) δ167.7, 146.3, 144.3, 142.6, 141.2, 140.6, 133.5, 131.9, 130.9, 128.3, 123.1, 121.0, 120.9, 118.0, 116.5, 113.7, 111.8, 101.2, 60.5, 60.2, 57.1, 56.4, 55.6, 55.5, 41.8, 41.6, 26.6, 25.3, 20.3, 15.9, 9.6; FTIR (neat) 3463 (m br), 2934 (m br), 1764 (m), 1716 (s), 1455 (m br), 1433 (m br), 1395 (m br), 1370 (m), 1233 (m), 1102 (m), 1073 (m) $cm^{-1}$; HPLC (Columbus, 5μ, $C_{18}$, 100 Å, 250×4.60 mm, flow rate: 1.0 mL/min, λ=254 nm), $R_T$=13.7 min (60% $CH_3CN$ in water) ; HRMS (FAB), [m+H]/z calc'd for $C_{36}H_{35}O_8N_4$: 651.2455, found 651.2444; $[\alpha]_D^{23}$=+21.9° (c 1.0, methylene chloride).

EXAMPLE 8

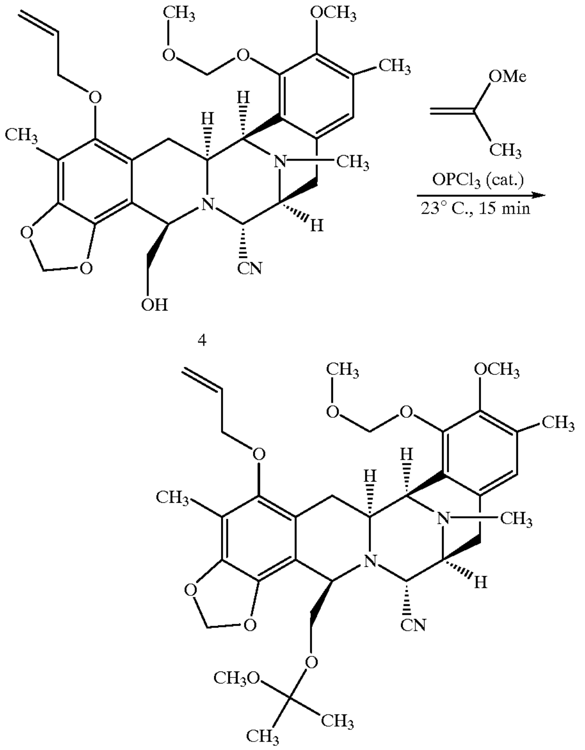

4

8 (99%)

Alcohol (4) (31.3 mg, 0.056 mmol) was dissolved in 2-methoxypropene. Catalytic phosphorus oxychloride was added and stirred at 23° C. for 15 min. One drop of triethylamine and methanol (1 mL) were added to quench the reaction which was then concentrated vacuo. The residue was purified by flash column chromatography (2 mL silica gel, gradient methylene chloride to 1:1 ethyl acetate-hexane) to afford Compound 8 (35.0 mg, 99%). $R_f$0.48 (1:1 ethyl acetate-hexane); $^1$H NMR (400 MHz, $CDCl_3$) δ6.62 (s, 1H), 6.17–6.06 (m, 1H), 5.92 (s, 1H), 5.85 (s, 1H), 5.41 (d, J=17.2 Hz, 1H), 5.27 (d, J=10.4 Hz, 1H), 5.13–5.08 (m, 2H), 4.41 (s, 1H), 4.23–4.10 (m, 3H), 4.04 (d, J=8.2 Hz, 1H), 3.73 (s, 3H), 3.43 (s, 3H), 3.42 (dd, J=8.8, 2.6 Hz, 1H), 3.29 (d, J=7.7 Hz, 1H), 3.22 (d, J=14.1 Hz, 2H), 3.07–2.96 (m, 4H), 2.84 (t, J=8.9 Hz, 1H), 2.64 (d, J=17.6 Hz, 1H), 2.31 (s, 3H), 2.12 (s, 3H), 2.02 (s, 3H), 1.82 (dd, J=15.3, 12.0 Hz, 1H), 1.29 (s, 3H), 1.17 (s, 3H); $^{13}$C NMR (100 MHz, $CDCl_3$) δ148.5, 148.3, 148.1, 144.2, 139.3, 133.8, 130.8, 130.2, 124.8, 124.2, 121.4, 118.9, 117.6, 113.0, 112.0, 101.0, 99.8, 99.2, 74.2, 67.0, 62.0, 59.7, 57.7, 57.4, 57.3, 56.7, 55.5, 48.3, 41.6, 26.3, 25.6, 24.4, 24.3, 15.7, 9.3; FTIR (neat) 2988 (w), 2933 (m br), 2825 (w), 1483 (m), 1460 (m), 1444 (m), 1432 (m), 1421 (m), 1380 (m), 1367 (w), 1341 (w), 1232 (w), 1212 (m), 1157 (m), 1104 (s), 1094 (s), 1076 (m), 1066 (m), 1046 (m), 1023 (m), 999 (m) $cm^{-1}$; HRMS (FAB), [m+Na]/z calc'd for $C_{35}H_{45}O_8N_3Na$: 658.3104, found 658.3114; $[\alpha]_D^{23}$+107° (c 0.10, methylene chloride).

EXAMPLE 9

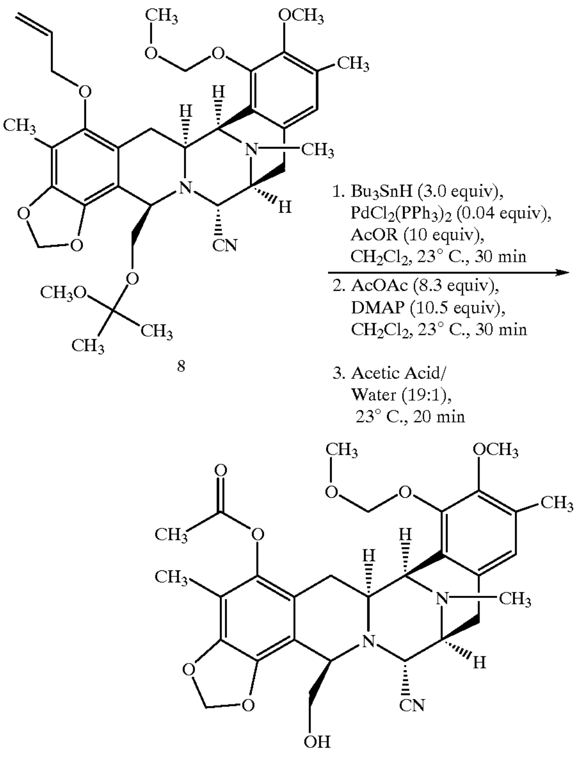

8

9 (89% yield over 3 steps)

Allyl ether (8) (35.0 mg, 0.055 mmol) and acetic acid (20.0 μL, 0.35 mmol) were dissolved in methylene chloride (2.0 mL). $PdCl_2(PPh_3)_2$ (2.5 mg, 0.0036 mmol) was added as a solid followed by tributyltin hydride (40.0 μL, 0.148 mmol). Bubbling was observed and the reaction changes color from a yellow to a dark orange. After stirring at 23° C. for 5 min, triethylamine (100 μL, 0.72 mmol), 4-dimethylaminopyridine (7.0 mg, 0.057 mmol) and acetic anhydride (10.0 μL, 0.10 mmol) were added to the solution. After stirring at 23° C. for 10 min, the reaction was concentrated in vacuo and dissolved in a solution of 19:1 acetic acid-water (2.0 mL). After stirring at 23° C. for 5 min the reaction was concentrated in vacuo and the residue was purified by flash column chromatography (14 mL silica gel, gradient 1:1 to 2:1 ethyl acetate-hexane) to afford Compound 9 (27.8 mg, 89%). $R_f$0.19 (1:1 ethyl acetate-hexane); $^1$H NMR (500 MHz, $CDCl_3$) δ6.70 (s, 1H), 5.96 (d, J=1.3 Hz, 1H), 5.90 (d, J=1.4 Hz, 1H), 5.14 (d, J=5.7 Hz, 1H), 5.07 (d, J=5.7 Hz, 1H), 4.21 (d, J=2.3 Hz, 1H) 4.10 (d, J=1.8 Hz, 1H), 3.99 (t, J=3.3 Hz, 1H), 3.72 (s, 3H), 3.66 (d, J=11.1 Hz, 1H), 3.58 (s, 3H), 3.49–3.44 (m, 1H), 3.40–3.32 (m, 2H), 3.10 (dd, J=18.0, 7.9 Hz, 1H), 2.79 (d, J=15.7 Hz, 1H), 2.51 (d, J=18.1 Hz, 1H), 2.36 (s, 3H), 2.32 (s, 3H), 2.21 (s, 3H), 2.00 (s, 3H), 1.82–1.70 (m, 2H); $^{13}$C NMR (125 MHz, $CDCl_3$) δ168.5, 148.6, 148.3, 144.5, 140.6, 140.4, 131.3, 129.5, 125.1, 123.6, 120.5, 117.6, 113.2, 111.7, 101.5, 99.2, 63.6, 59.9, 59.8, 58.0, 57.7, 56.9, 56.1, 55.3, 41.6, 26.3, 25.6, 20.1, 15.7, 9.3; FTIR (neat) 3500 (m br), 2935 (s br), 2854 (w), 1760 (s), 1484 (m), 1440 (m), 1434 (m), 1401 (m), 1370 (m), 1341 (w), 1324 (w), 1234 (m), 1201 (s), 1158 (m), 1106 (s), 1086 (s), 1075 (s), 1043 (m), 1023 (m), 1000 (m), 961 (m), 912 (m) $cm^{-1}$; HRMS (FAB), [m+Na]/z calc'd for $C_{30}H_{35}O_8N_3Na$: 588.2322, found 588.2303; $[\alpha]_D^{23}$+50.2° (c 0.66, methylene chloride).

Methods for Generating the Dicarboximides

Many of the phthalimides and dicarboximides were not commercially available and had to be synthesized from the commercially available anhydrides or dicarboxylic acids using a variety of established methodologies. The dicarboxylic acids were converted to the anhydrides by heating with acetic anhydride. Heating the anhydrides with urea[1], urethane[2] or formamide[3] at

[1] Campayo, L.; Jimenez, B.; Manzano, T.; Navarro, P. *Synthesis* 1985, 197 and Crockett, G. C.; Swanson, B. J.; Anderson, D. R.; Koch, T. H. *Synth. Commun.* 1981, 11 (6), 447–454.

[2] Weidner-Wells, M. A.; DeCamp, A.; Mazzocchi, P. H. *J. Org. Chem.* 1989, 54 (24), 5746–5758.

[3] Vostrova, V. N.; Plakidin, V. L. *J. Org. Chem. USSR* 1982, 18, 1754 and Ganin, E. V.; Makarov, V. F.; Nikitin, V. I. *J. Org. Chem. USSR* 1987, 23, 981–983. ~200° C. (15 minutes to 12 hours) and crystallization from water afforded pure to semi-pure dicarboximides. Filtration through a pad of silica gel and elution with ethyl acetate provided pure material. Alternatively the anhydrides were reacted with ammonium hydroxide followed by refluxing in ethanol with catalytic hydrochloric acid[4]. The 1,2-Naphthalimide was synthesized via a Diels-Alder with β-bromostyrene and maleimide.[5] p-Toluenesulfonyl isocyanate and t-butanol were reacted in order to generate the BOC-protected tolylsulfonamide.[6] The dicarboximides were systematically dried under vacuum (60° C., 30 mm) and by toluene azeotrope immediately before use.

[4] Alexion, M.; Tyman, J.; Wilson, I. *Tetrahedron Lett.* 1981, 22 (24), 2303.

[5] Newman, M. S.; Dhawan, B.; Hahem, M. M.; Khanna, V. K.; Springer, J. M. *J. Org. Chem.* 1976, 41 (24), 3925.

[6] Corey, E. J.; Su, Wei-juo *Tetrahedron Lett.* 1990, 31 (27), 3833–3836.

EXAMPLE 10

General Procedure for the Mitsunobu Coupling Reaction of Alcohol (9) with Dicarboximides

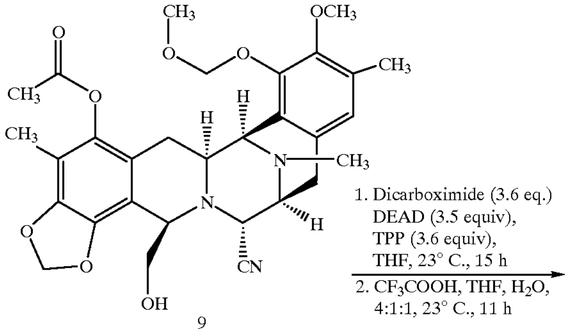

9

-continued

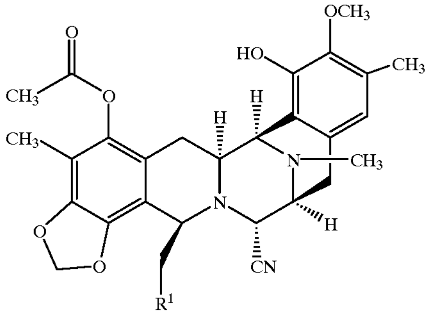

10–19

The alcohol (9) (1.0 mg, 0.0018 mmol) and the dicarboximide (0.0065 mmol, 3.6 equiv.) were azeotropically dried with toluene (2×0.1 mL) and dissolved in THF (0.2 mL). Triphenylphosphine (1.7 mg, 0.0065 mmol) was added as a solid followed by diethyl azodicarboxylate (1.0 μL, 0.0064 mmol) via syringe. The reaction turned yellow and after stirring at 23° C.[7] for 15 h the reaction was concentrated in vacuo. The residue was purified by flash column chromatography (1.0 mL silica gel, gradient methylene chloride to 2:1 diethyl ether-hexane to 1:1 to 2:1 ethyl acetate-hexane) followed by preparative thin layer chromatography to afford the desired product.

The methoxymethyl ether was dissolved in a mixture of trifluoroacetic acid-THF-water (4:1:1 (v/v), 1.2 mL) and the solution was stirred at 23° C. for 11 h. The reaction mixture was diluted with toluene (1 mL) and the solution was concentrated in vacuo. Additional volatiles were removed by repetitive in vacuo azeotropic concentration from toluene (3×1 mL). The residue was purified by flash column chromatography (0.5 mL silica gel, gradient methylene chloride to 2:1-ethyl acetate-hexane) to afford the desired product.

TABLE 1

General Procedure for the Coupling of Alcohol (9) with Dicarboximides.

| Entry | Compound # | Dicarboximide | Mitsunobu Coupling Yield (%) | MOM Removal Yield (%) |
|---|---|---|---|---|
| 1 | 10 | 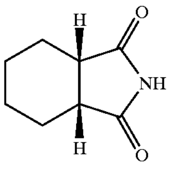 | 56 | 100 |
| 2 | 11 | 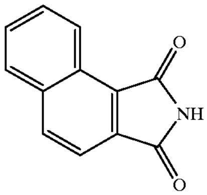 | 51 | 40 |

TABLE 1-continued
General Procedure for the Coupling of Alcohol (9) with Dicarboximides.
| Entry | Compound # | Dicarboximide | Mitsunobu Coupling Yield (%) | MOM Removal Yield (%) |
|---|---|---|---|---|
| 3 | 12 | 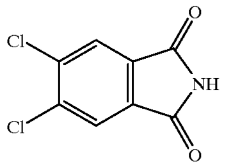 | 89 | 53 |
| 4 | 13 | 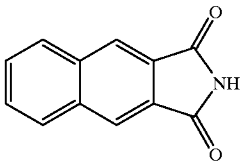 | 53 | 91 |
| 5 | 14 | 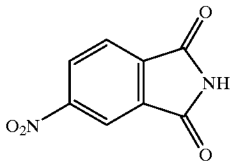 | 61 | 93 |
| 6 | 15 | 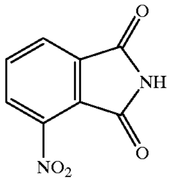 | 76 | 96 |
| 7 | 16 | 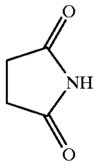 | 82 | 25 |
| 8 | 17 | 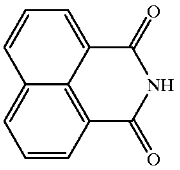 | 92 | 90 |
| 9 | 18 | 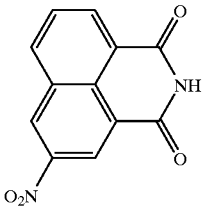 | 100 | 98 |

TABLE 1-continued

General Procedure for the Coupling of Alcohol (9) with Dicarboximides.

| Entry | Compound # | Dicarboximide | Mitsunobu Coupling Yield (%) | MOM Removal Yield (%) |
|---|---|---|---|---|
| 10 | 19 | 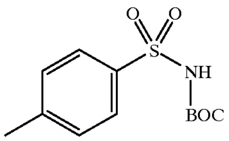 | 34 | 100 |

[7] Heating to 40° C. was required for entries 8 and 9.

EXAMPLE 11

Compound 10—Preparative thin layer chromatography of the first step done using 4:1 diethyl ether-hexane. $R_f$0.42 (2:1 ethyl acetate-hexane); $^1$H NMR (500 MHz, $CDCl_3$) δ6.50 (s, 1H), 5.99 (s, 1H), 5.91 (s, 1H), 5.62 (s, 1H), 4.28 (s, 1H), 4.16 (d, J=3.1 Hz, 1H), 4.02 (s, 1H), 3.76 (s, 3H), 3.75–3.70 (m, 2H), 3.37 (d, J=7.3 Hz, 1H), 3.15 (d, J=11.4 Hz, 1H), 2.96 (dd, J=18.0, 7.9 Hz, 1H), 2.86 (d, J=18.0 Hz, 1H), 2.74 (d, J=15.5 Hz, 1H), 2.43 (q, J=7.4 Hz, 1H), 2.29 (s, 6H), 2.26 (s, 3H), 2.01 (s, 3H), 2.04–2.02 (m, 1H), 1.80–1.45 (m, 4H), 1.40–1.17 (m, 5H); FTIR (neat) 3412 (m br), 2935 (m br), 2858 (m), 2256 (w), 1759 (m), 1706 (s), 1498 (w), 1452 (m), 1434 (m), 1396 (m), 1370 (m), 1334 (m), 1325 (m), 1295 (m), 1234 (m), 1201 (m), 1148 (m), 1105 (m), 1093 (m), 1075 (m), 1008 (m), 913 (m) $cm^{-1}$; HRMS (FAB), [m+Na]/z calc'd for $C_{36}H_{40}O_8N_4Na$: 679.2744, found 679.2727.

EXAMPLE 12

Compound 11—Preparative thin layer chromatography of the first step was done using 4:1 diethyl ether-hexane. $R_f$0.45 (2:1 ethyl acetate-hexane); $^1$H NMR (500 MHz, $CDCl_3$) δ8.85 (d, J=8.7 Hz, 1H), 8.12 (d, J=8.2 Hz, 1H), 7.95 (d, J=8.1 Hz, 1H), 7.76–7.72 (m, 2H), 7.67–7.65 (m, 1H), 6.26 (s, 1H) 5.63 (s, 1H), 5.58 (s, 1H), 5.34 (br s, 1H), 4.33–4.28 (m, 2H), 4.07 (s, 1H), 3.72–3.65 (m, 2H), 3.57 (s, 3H), 3.40 (d, J=8.0 Hz, 1H), 3.25 (d, J=11.5 Hz, 1H), 3.02 (dd, J=17.1, 7.6 Hz, 1H), 2.80 (d, J=14.9 Hz, 1H), 2.66 (d, J=18.6 Hz, 1H), 2.31 (s, 3H), 2.30 (s, 3H), 2.00 (s, 3H), 1.99 (s, 3H), 1.80 (dd, J=14.9, 11.7 Hz, 1H); FTIR (neat) 3438 (m br), 2938 (m br), 1763 (m), 1706 (s), 1588 (w), 1500 (w), 1456 (m), 1431 (m), 1388 (m), 1231 (m), 1200 (m), 1144 (w), 1100 (m), 1075 (m), 1031 (w), 1006 (w) $cm^{-1}$; HRMS (FAB), [m+Na]/z calc'd for $C_{40}H_{36}O_8N_4Na$: 723.2431, found 723.2443.

EXAMPLE 13

Compound 12—Preparative thin layer chromatography of the first step was done using 1:1 ethyl acetate-hexane. $R_f$0.34 (1:1 ethyl acetate-hexane); $^1$H NMR (500 MHz, $CDCl_3$) δ7.73 (s, 2H), 6.40 (s, 1H), 5.78 (s, 1H), 5.63 (br s, 1H), 5.55 (s, 1H), 4.24–4.21 (m, 2H), 4.00 (d, J=1.9 Hz, 1H), 3.74–3.71 (m, 2H), 3.60 (s, 3H), 3.36 (d, J=8.1 Hz, 1H), 3.18 (d, J=11.9 Hz, 1H), 3.00 (dd, J=17.9, 8.2 Hz, 1H), 2.75–2.69 (m, 2H), 2.28 (s, 6H), 2.24 (s, 3H), 2.01 (s, 3H), 1.61–1.54 (m, 1H); FTIR (neat) 3415 (m br), 2933 (m br), 2855 (w), 1762 (m), 1720 (s), 1500 (w), 1459 (m), 1452 (m), 1433 (m), 1387 (m), 1369 (m), 1265 (m), 1234 (m), 1196 (m), 1144 (m), 1102 (m), 1083 (m), 1074 (m) $cm^{-1}$; HRMS (FAB), [m+Na]/z calc'd for $C_{36}H_{32}O_8N_4Cl_2Na$: 741.1495, found 741.1498.

EXAMPLE 14

Compound 13—Preparative thin layer chromatography of the first step was done using 4:1 diethyl ether-hexane and again using 1:1 ethyl acetate-hexane. $R_f$0.20 (1:1 ethyl acetate-hexane); $^1$H NMR (500 MHz, $CDCl_3$) δ8.21 (s, 2H), 8.03 (dd, J=6.1, 3.2 Hz, 2H), 7.69 (dd, J=6.1, 3.2 Hz, 2H), 6.38 (s, 1H), 5.62 (s, 1H), 5.57 (s, 1H), 5.30 (s, 1H), 4.31–4.28 (m, 2H), 4.02 (s, 1H), 3.73–3.68 (m, 2H), 3.52 (s, 3H), 3.36 (d, J=7.3 Hz, 1H), 3.22 (d, J=11.7 Hz, 1H), 3.02 (dd, J=18.2, 7.7 Hz, 1H), 2.78 (d, J=15.3 Hz, 1H), 2.67 (d, J=18.0 Hz, 1H), 2.30 (s, 3H), 2.29 (s, 3H), 2.13 (s, 3H), 1.99 (s, 3H), 1.78 (dd, J=14.8, 12.4 Hz, 1H); FTIR (neat) 3428 (m br), 2983 (m br), 1766 (m), 1712 (s), 1432 (m), 1384 (m), 1197 (m), 1150 (w), 1103 (m), 905 (w) $cm^{-1}$; HRMS (FAB), [m+Na]/z calc'd for $C_{40}H_{36}O_8N_4Na$: 723.2431, found 723.2416.

EXAMPLE 15

Compound 14—Preparative thin layer chromatography of the first step was done using 4:1 diethyl ether-hexane. $R_f$0.20 (4:1 diethyl ether-hexane); $^1$H NMR (400 MHz, $CDCl_3$) δ8.50 (d, J=7.9 Hz, 1H), 8.46 (s, 1H), 7.85 (d, J=8.1 Hz, 1H), 6.43 (s, 1H), 5.76 (s, 1H), 5.58 (br s, 1H), 5.54 (s, 1H), 4.27 (t, J=4.6 Hz, 1H), 4.24 (d, J=2.0 Hz, 1H), 4.00 (d, J=2.5 Hz, 1H), 3.79 (d, J=4.0 Hz, 2H), 3.57 (br s, 3H), 3.38 (d, J=8.0 Hz, 1H), 3.18 (d, J=11.6 Hz, 1H), 3.02 (dd, J=18.1, 8.1 Hz, 1H), 2.74 (d, J=16.7 Hz, 2H), 2.28 (s, 3H), 2.26 (s, 3H), 2.21 (s, 3H), 2.01 (s, 3H), 1.65–1.55 (m, 1H); FTIR (neat) 3488 (w br), 2932 (m br), 1761 (m), 1725 (s), 1622 (w), 1584 (w), 1541 (m), 1499 (w), 1435 (m), 1393 (w), 1345 (m), 1233 (m), 1196 (m), 1146 (w), 1105 (m), 1075 (m), 1030 (m), 1001 (w), 951 (w), 907 (w) $cm^{-1}$; HRMS (FAB), [m+Na]/z calc'd for $C_{36}H_{33}O_{10}N_5Na$: 718.2125, found 718.2125.

EXAMPLE 16

Compound 15—Preparative thin layer chromatography of the first step was done using 1:1 ethyl acetate-hexane. $R_f$0.25 (2:1 ethyl acetate-hexane); $^1$H NMR (500 MHz, $CDCl_3$) δ8.07 (dd, J=8.1, 0.7 Hz, 1H), 7.96 (dd, J=7.5, 0.8 Hz, 1H), 7.84 (t, J=7.8 Hz, 1H), 6.36 (s, 1H), 5.68 (s, 1H), 5.60 (s, 1H), 5.46 (br s, 1H), 4.30–4.20 (m, 2H), 4.03 (d, J=1.8 Hz, 1H), 3.75–3.65 (m, 5H), 3.35 (d, J=8.4 Hz, 1H), 3.21 (d, J=12.3 Hz, 1H), 3.02 (dd, J=18.2, 8.2 Hz, 1H), 2.78 (d, J=16.5 Hz, 1H), 2.61 (d, J=17.8 Hz, 1H), 2.30 (s, 3H), 2.28 (s, 3H), 2.21 (s, 3H), 2.00 (s, 3H), 1.80–1.70 (m, 1H); FTIR (neat) 3490 (w br), 2938 (m br), 1762 (m), 1722 (s), 1543 (m), 1459 (m), 1448 (m), 1444 (m), 1433 (m), 1394 (m), 1369 (m), 1233 (m), 1196 (m), 1103 (m), 1074 (m) $cm^{-1}$; HRMS (FAB), [m+Na]/z calc'd for $C_{36}H_{33}O_{10}N_5Na$: 718.2125, found 718.2122.

EXAMPLE 17

Compound 16—Preparative thin layer chromatography of the first step was done using 2:1 ethyl acetate-hexane. $R_f$0.19 (2:1 ethyl acetate-hexane); $^1$H NMR (400 MHz, $CDCl_3$) δ6.49 (s, 1H), 5.94 (s, 1H), 5.87 (s, 1H), 5.64 (s, 1H), 4.20

(d, J=2.2 Hz, 1H), 4.15 (t, J=4.4 Hz, 1H), 4.03 (d, J=1.2 Hz, 1H), 3.78 (s, 3H), 3.65–3.43 (m, 2H), 3.35 (d, J=7.8 Hz, 1H), 3.17 (d, J=12.3 Hz, 1H), 2.99 (dd, J=18.5, 7.9 Hz, 1H), 2.76 (dd, J=15.6, 1.8 Hz, 2H), 2.43–2.10 (m, 13H), 2.01 (s, 3H), 1.70–1.60 (m, 1H); FTIR (neat) 3428 (m br), 2926 (s br), 2853 (m), 1757 (m), 1705 (s), 1497 (w), 1431 (m br), 1233 (w), 1198 (m), 1150 (w), 1086 (m), 920 (w) $cm^{-1}$; HRMS (FAB), [m+Na]/z calc'd for $C_{32}H_{34}O_8N_4Na$: 625.2274, found 625.2274.

EXAMPLE 18

Compound 17—The Mitsunobu was conducted at 40° C. and the purification by preparative thin layer chromatography was done using 10% ethyl acetate-methylene chloride and again using 5% methanol-methylene chloride. $R_f$0.31 (2:1 ethyl acetate-hexane); $^1H$ NMR (500 MHz, $CDCl_3$) δ8.48 (m, 2H), 8.21 (dd, J=8.3, 0.9 Hz, 2H), 7.75 (t, J=7.6 Hz, 2H), 6.34 (s, 1H), 5.68 (s, 1H), 5.29 (s, 1H), 4.62 (br s, 1H), 4.46 (d, J=2.2 Hz, 1H), 4.34 (dd, J=9.4, 3.3 Hz, 1H), 4.23 (dd, J=12.7, 9.7 Hz, 1H), 4.07 (d, J=2.2 Hz, 1H), 3.90 (dd, J=13.0, 3.3 Hz, 1H), 3.79 (s, 3H), 3.35 (d, J=9.5 Hz, 1H), 3.24 (d, J=11.9 Hz, 1H), 3.04 (dd, J=18.3, 8.4 Hz, 1H), 2.85 (d, J=14.9 Hz, 1H), 2.58 (d, J=17.8 Hz, 1H), 2.34 (s, 3H), 2.30 (s, 3H), 2.24 (s, 3H), 2.02–1.95 (m, 1H), 1.94 (s, 3H); FTIR (neat) 3422 (m br), 2929 (m br), 1761 (m), 1704 (m), 1660 (s), 1591 (m), 1456 (m), 1439 (m), 1378 (m), 1236 (s), 1198 (m), 1105 (m), 1074 (m) $cm^{-1}$; HRMS (FAB), [m+Na]/z calc'd for $C_{40}H_{36}O_8N_4Na$: 723.2431, found 723.2433.

EXAMPLE 19

Compound 18—The Mitsunobu was conducted at 40° C. and the purification by preparative thin layer chromatography of the first step was done using 5% methanol-methylene chloride. $R_f$0.45 (2:1 ethyl acetate-hexane); $^1H$ NMR (500 MHz, $CDCl_3$) δ9.19 (s, 1H), 9.12 (d, J=2.2 Hz, 1H), 8.66 (d, J=6.5 Hz, 1H), 8.41 (d, J=8.3 Hz, 1H), 7.93 (t, J=7.8 Hz, 1H), 6.34 (s, 1H), 5.67 (s, 1H), 5.34 (s, 1H), 4.75 (br s, 1H), 4.42 (d, J=2.3 Hz, 1H), 4.34 (dd, J=9.3, 3.2 Hz, 1H), 4.29–4.21 (m, 1H), 4.07 (d, J=2.0 Hz, 1H), 3.95 (dd, J=13.1, 3.1 Hz, 1H), 3.77 (s, 3H), 3.37 (d, J=7.9 Hz, 1H), 3.23 (d, J=11.8 Hz, 1H), 3.06 (dd, J=18.1, 8.2 Hz, 1H), 2.84 (d, J=15.5 Hz, 1H), 2.59 (d, J=18.1 Hz, 1H), 2.33 (s, 3H), 2.30 (s, 3H), 2.22 (s, 3H), 2.03–1.85 (m, 4H); FTIR (neat) 3463 (m br), 2931 (m br), 1762 (m), 1711 (m), 1668 (s), 1600 (m), 1542 (m), 1458 (m), 1433 (m), 1420 (m), 1370 (m), 1345 (m), 1328 (m), 1234 (m), 1197 (m), 1104 (m), 1075 (m) $cm^{-1}$; HRMS (FAB), [m+Na]/z calc'd for $C_{40}H_{35}O_{10}N_5Na$: 768.2282, found 768.2308.

EXAMPLE 20

Compound 19—Preparative thin layer chromatography of the first step was done using 4:1 diethyl ether-hexane. $R_f$0.50 (2:1 ethyl acetate-hexane); $^1H$ NMR (500 MHz, $CDCl_3$) δ7.28 (d, J=8.2 Hz, 2H), 7.00 (d, J=8.0 Hz, 2H), 6.59 (s, 1H), 5.76 (s, 2H), 5.53 (br s, 1H), 4.11 (s, 1H), 4.00 (d, J=6.3 Hz, 1H), 3.93 (s, 1H), 3.89 (s, 1H), 3.80 (s, 3H), 3.57–3.45 (m, 1H), 3.35–3.29 (m, 2H), 3.18–3.11 (m, 2H), 2.72–2.87 (m, 1H), 2.49 (d, J=16.9 Hz, 1H), 2.39 (s, 3H), 2.36 (s, 3H), 2.33 (s, 3H), 2.32 (s, 3H), 1.99 (s, 3H), 1.82 (dd, J=16.4, 12.4 Hz, 1H); FTIR (neat) 3425 (w br), 3331 (m br), 2958 (m), 2927 (s br), 2855 (m), 1759 (s), 1719 (w), 1498 (w), 1459 (m), 1390 (m), 1370 (m), 1326 (m), 1233 (s), 1201 (s), 1154 (s), 1111 (m), 1088 (s), 1074 (s), 1028 (m), 1007 (m), 995 (w) $cm^{-1}$; HRMS (FAB), [m+Na]/z calc'd for $C_{35}H_{38}O_8N_4SNa$: 697.2308, found 697.2318.

EXAMPLE 21

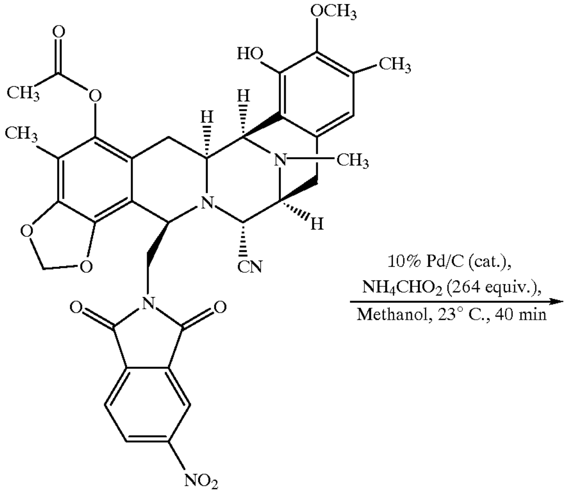

14

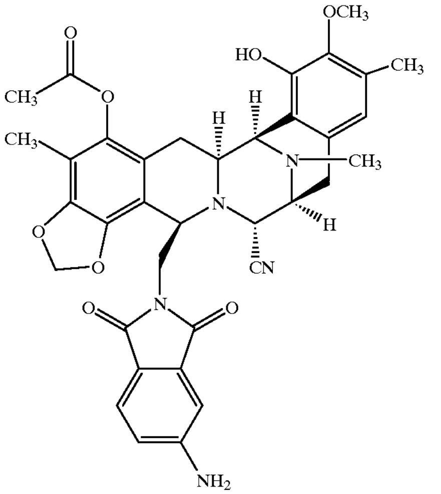

20 (63%)

Nitro compound (14) (0.5 mg, 0.00072 mmol) was dissolved in methanol (0.4 mL), 10% Pd/C (0.2 mg) and ammonium formate (12.0 mg, 0.19 mmol) were added at 23° C. and the reaction was stirred for 40 min. The mixture was diluted with ethyl acetate (2 mL), filtered through a plug of Celite, concentrated in vacuo and the residue was purified by flash column chromatography (1.5 mL silica gel, 2:1 ethyl acetate-hexane) to afford Compound 20 (0.3 mg, 63%). $R_f$0.20 (2:1 ethyl acetate-hexane); $^1H$ NMR (500 MHz, $CDCl_3$) □ 7.49 (d 8.1 1), 6.91 (d 2.1, 1H), 6.77 (dd, J=8.1, 2.2 Hz, 1H), 6.38 (s, 1H), 5.67 (s, 1H), 5.61 (s, 1H), 5.34 (br s, 1H), 4.28 (br s, 2H), 4.23–4.19 (m, 2H), 4.03 (d, J=1.8 Hz, 1H), 3.71 (s, 3H), 3.53 (d, J=5.7 Hz, 2H), 3.33 (d, J=8.2 Hz, 1H), 3.20 (d, J=12.3 Hz, 1H), 3.01 (dd, J=17.6, 8.1 Hz, 1H), 2.78 (d, J=14.7 Hz, 1H), 2.61 (d, J=18.6 Hz, 1H), 2.31 (s, 3H), 2.29 (s, 3H), 2.24 (s, 3H), 1.98 (s, 3H), 1.79 (dd, J=14.4, 11.8 Hz, 1H); FTIR (neat) 3456 (w br), 3374 (m br), 3243 (w br), 2932 (m br), 2853 (w), 1760 (m), 1703 (m), 1699 (s), 1617 (m), 1501 (m), 1463 (m), 1457 (m), 1431 (m), 1398 (m), 1232 (m), 1199 (m), 1103 (m), 1073 (m) $cm^{-1}$; HRMS (FAB), [m+Na]/z calc'd for $C_{36}H_{35}O_8N_5Na$: 688.2383, found 688.2367.

EXAMPLE 22

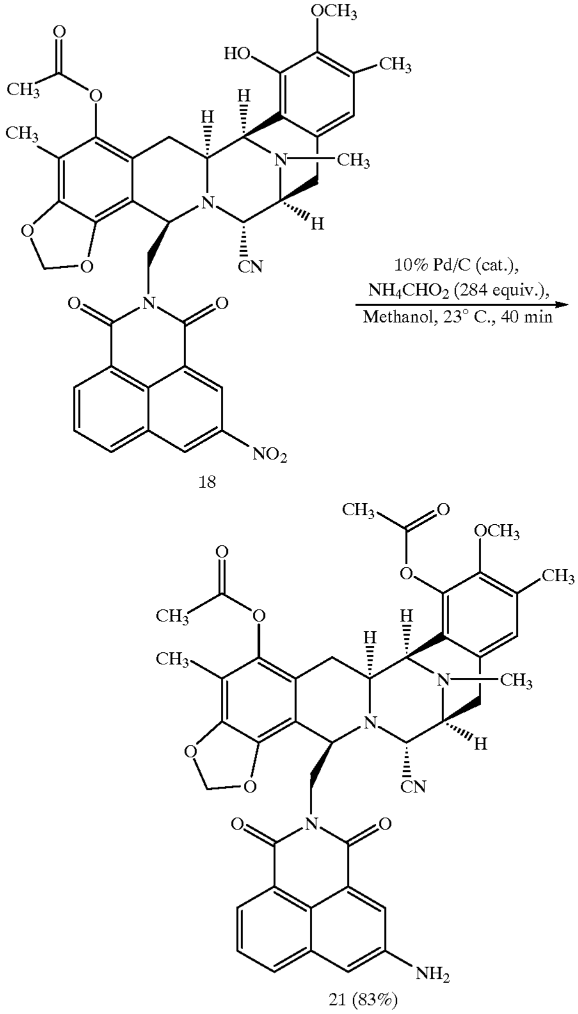

18

21 (83%)

Nitro compound (18) (0.5 mg, 0.00067 mmol) was dissolved in methanol (0.4 mL), 10% Pd/C (0.2 mg) and ammonium formate (12.0 mg, 0.19 mmol) were added at 23° C. and the reaction was stirred for 40 min. The mixture was diluted with ethyl acetate (2 mL), filtered through a plug of Celite, concentrated in vacuo and the residue was purified by flash column chromatography (1.5 mL silica gel, 2:1 ethyl acetate-hexane) to afford Compound 21 (0.4 mg, 83%). $R_f$0.28 (2:1 ethyl acetate-hexane); $^1$H NMR (500 MHz, $CDCl_3$) δ8.21 s (1), 7.93–7.91 (m, 2H), 7.59 (t, J=7.8 Hz, 1H), 7.28 (d, J=2.3 Hz, 1H), 6.35 (s, 1H), 5.68 (s, 1H), 5.32 (s, 1H), 4.67 (br s, 1H), 4.44 (s, 1H), 4.32 (dd, J=9.6, 3.2 Hz, 1H), 4.20 (t, J=11.0 Hz, 1H), 4.14 (s, 2H), 4.07 (d, J=2.3 Hz, 1H), 3.86 (dd, J=13.1, 3.3 Hz, 1H), 3.80 (s, 3H), 3.34 (d, J=8.5 Hz, 1H), 3.24 (d, J=12.1 Hz, 1H), 3.04 (dd, J=17.8, 7.9 Hz, 1H), 2.84 (d, J=14.4 Hz, 1H), 2.57 (d, J=17.6 Hz, 1H), 2.34 (s, 3H), 2.30 (s, 3H), 2.24 (s, 3H), 2.05–1.93 (m, 4H); FTIR (neat) 3456 (m br), 3369 (s br), 3250 (w br), 2931 (m br), 2856 (w), 1750 (m), 1700 (s), 1656 (s), 1619 (s), 1581 (m), 1450 (s), 1375 (m), 1331 (w), 1300 (m), 1231 (m), 1219 (m), 1150 (w), 1106 (m), 1075 (m) cm$^{-1}$; HRMS (FAB), [m+Na]/z calc'd for $C_{40}H_{37}O_8N_5Na$: 738.2540, found 738.2566.

EXAMPLE 23

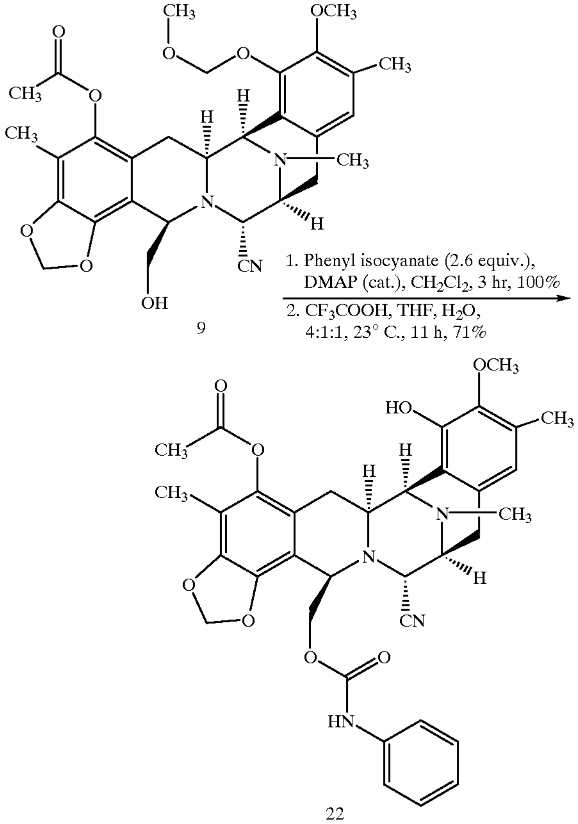

9

22

Alcohol (9) (1.0 mg, 0.0018 mmol) was dissolved in methylene chloride (0.2 mL) and 4-dimethylaminopyridine (0.1 mg, 0.00082 mmol) and phenyl isocyanate (0.5 μL, 0.0046 mmol) were added to the solution. The reaction was stirred at 23° C. for 3 hr and then quenched into a saturated solution of aqueous sodium bicarbonate (10 mL). The mixture was extracted with methylene chloride (2×5 mL) and the organic layers were dried over sodium sulfate, decanted and concentrated in vacuo to afford a residue (1.2 mg, 100%). This crude material was dissolved in a mixture of trifluoroacetic acid-THF-water (4:1:1 (v/v), 1.0 mL) and the solution was stirred at 23° C. for 11 hr. The reaction mixture was diluted with toluene (1 mL) and the solution was concentrated in vacuo. Additional volatiles were removed by repetitive in vacuo azeotropic concentration from toluene (3×1 mL). The residue was purified by flash column chromatography (1 mL silica gel, gradient methylene chloride to 1:4 to 1:1 to 2:1 ethyl acetate-hexane) to afford Compound 22 (0.8 mg, 71%). $R_f$0.54 (2:1 ethyl acetate-hexane); $^1$H NMR (500 MHz, $CD_2Cl_2$) δ7.28–7.25 (m, 4H), 7.04–7.01 (m, 1H), 6.33 (br s, 1H), 6.27 (s, 1H), 5.98 (d, J=1.2 Hz, 1H), 5.94 (d, J=1.3 Hz, 1H), 5.68 (s, 1H), 4.50 (dd, J=11.2, 3.2 Hz, 1H), 4.13–4.11 (m, 2H), 4.05 (d, J=2.2 Hz, 1H), 3.90 (dd, J=11.2, 3.4 Hz, 1H), 3.57 (br s, 3H), 3.33 (d, J=7.8 Hz, 1H), 3.17 (dt, J=11.9, 2.7 Hz, 1H), 2.95 (dd, J=17.9, 8.2 Hz, 1H), 2.83 (d, J=14.4 Hz, 1H), 2.63 (d, J=17.8 Hz, 1H), 2.34 (s, 3H), 2.24 (s, 3H), 2.03 (s, 3H), 1.87–1.81 (m, 1H), 1.81 (br s, 3H); FTIR (neat) 3375 (m br), 2933 (m br), 2873 (w), 1733 (m br), 1601 (m), 1533 (m), 1501 (m), 1445 (m), 1417 (m), 1371 (m), 1314 (m), 1299 (m), 1266 (m), 1214 (s), 1155 (m), 1145 (m), 1109 (m), 1086 (m), 1070 (m), 1029 (m), 1007 (m), 953 (w) cm$^{-1}$; HRMS (FAB), [m+Na]/z calc'd for $C_{35}H_{36}O_8N_4Na$: 663.2431, found 663.2417.

EXAMPLE 24

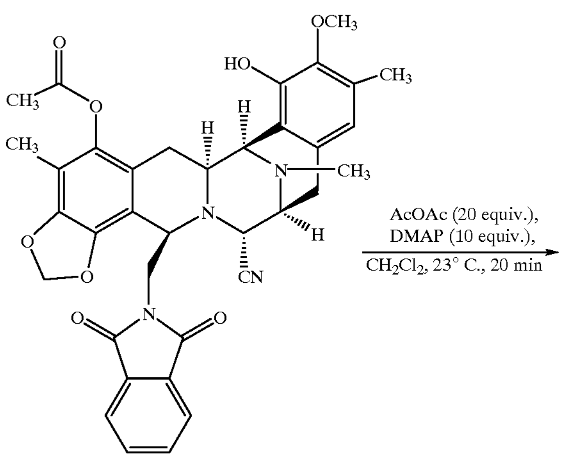

7

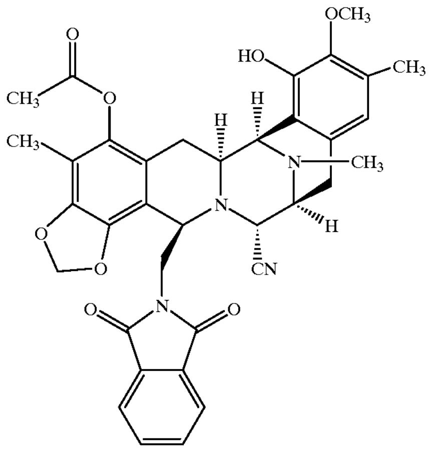

23 (94%)

Phthalimide (7) (0.3 mg, 0.00046 mmol) was dissolved in methylene chloride (0.2 mL) and 4-dimethylaminopyridine (0.6 mg, 0.0049 mmol) and acetic anhydride (1.0 $\mu$L, 0.010 mmol) were added to the solution. The reaction was stirred at 23° C. for 20 min and then purified by flash column chromatography (0.3 mL silica gel, gradient methylene chloride to ethyl acetate) to afford Compound 23 (0.3 mg, 94%). $R_f$0.19 (1:1 ethyl acetate-hexane); $^1$H NMR (400 MHz, $CDCl_3$) δ7.72–7.65 (m, 4H), 6.78 (s, 1H), 5.70 (s, 1H), 5.40 (br s, 1H), 4.25–4.23 (m, 2H), 3.72–3.63 (m, 2H), 3.63–3.50 (m, 4H), 3.38 (d, J=7.6 Hz, 1H), 3.19 (d, J=12.2 Hz, 1H), 3.05 (dd, J=18.1, 8.0 Hz, 1H), 2.72 (d, J=18.0 Hz, 1H), 2.62 (d, J=14.6 Hz, 1H), 2.33 (s, 3H), 2.31 (s, 3H), 2.25 (s, 3H), 2.23 (s, 3H), 2.00 (s, 3H), 1.78–1.63 (m, 1H); FTIR (neat) 2931 (m br), 2850 (w), 1769 (s), 1713 (s), 1494 (w), 1431 (m br), 1394 (m), 1369 (m), 1238 (m), 1194 (s), 1100 (m), 1075 (m) cm$^{-1}$; HRMS (FAB), [m+Na]/z calc'd for $C_{38}H_{36}O_9N_4Na$: 715.2380, found 715.2360.

EXAMPLE 25

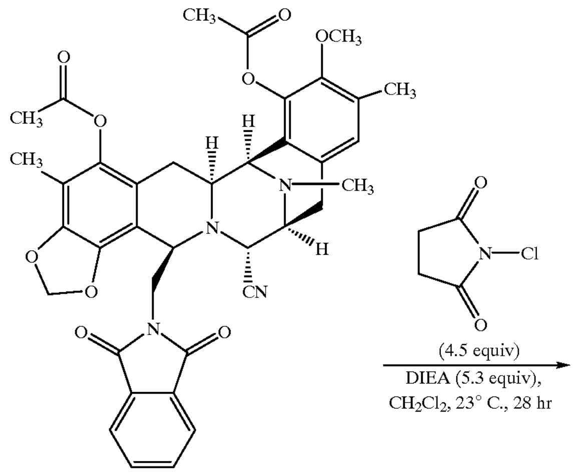

7

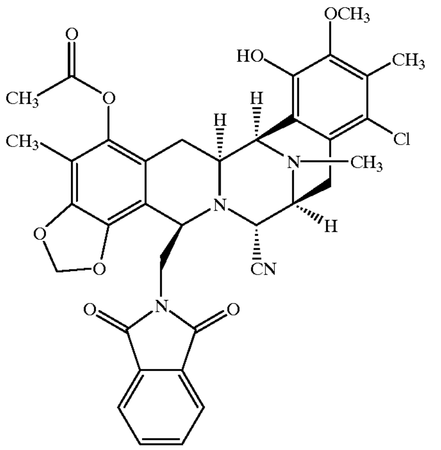

24 (68%)

Phthalimide (7) (0.7 mg, 0.0011 mmol) was dissolved in methylene chloride (0.2 mL) and N,N-diisopropylethylamine (1.0 $\mu$L, 0.0058 mmol) and N-chlorosuccinimide (0.66 mg, 0.0049 mmol) were added to the solution. The reaction was stirred at 23° C. for 28 hr and passed through a small plug of silica gel with ethyl acetate. The mixture was concentrated in vacuo and the residue was purified by preparative thin layer chromatography (10% ethyl acetate-methylene chloride, three elutions) to afford Compound 24 (0.5 mg, 68%). $R_f$0.19 (10% ethyl acetate-methylene chloride); $^1$H NMR (500 MHz, $CDCl_3$) δ7.72–7.70 (m, 2H), 7.65–7.63 (m, 2H), 5.70 (s, 1H), 5.56 (s, 1H), 5.39 (br s, 1H), 4.28 (d, J=2.2 Hz, 1H), 4.25 (t, J=5.4 Hz, 1H), 4.07 (s, 1H), 3.66 (d, J=4.9 Hz, 2H), 3.60 (s, 3H), 3.46 (d, J=8.3 Hz, 1H), 3.22 (d, J=11.7 Hz, 1H), 2.96 (dd, J=18.7, 8.0 Hz, 1H), 2.76 (d, J=15.8 Hz, 1H), 2.70 (d, J=18.6 Hz, 1H), 2.30 (s, 3H), 2.28 (s, 6H), 1.99 (s, 3H), 1.67 (t, J=12.4 Hz, 1H); FTIR (neat) 3407 (m br), 2936 (m br), 2854 (w), 1764 (m), 1716 (s), 1466 (m), 1452 (m), 1431 (m), 1408 (m), 1395 (m), 1369 (m), 1315 (w), 1273 (w), 1235 (m), 1197 (m), 1146 (w), 1102 (m), 1086 (m), 1074 (m), 1031 (m), 1003 (w), 947 (m) cm$^{-1}$; HRMS (FAB), [m+Na]/z calc'd for $C_{36}H_{33}O_8N_4ClNa$: 707.1885, found 707.1888.

EXAMPLE 26

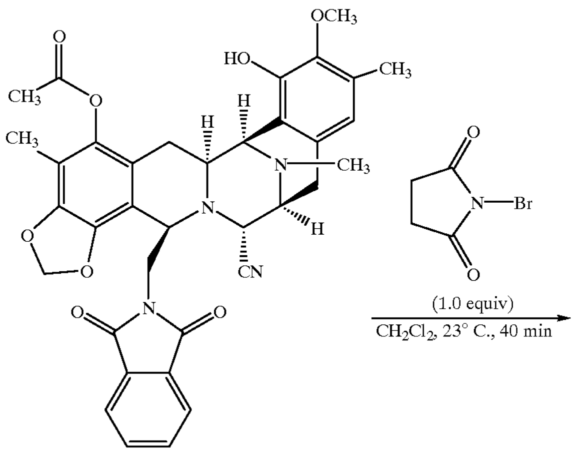

7

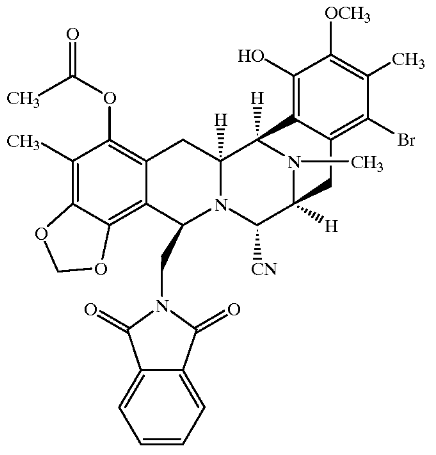

25 (89%)

Phthalimide (7) (0.5 mg, 0.00077 mmol) was dissolved in a 0.0056 M solution of N-bromosuccinimide in methylene chloride (0.14 mL, 0.00079 mmol). The reaction was stirred at 23° C. for 40 min and was then quenched into a saturated solution of sodium thiosulfate (10 mL). The mixture was extracted with ethyl acetate (10 mL) and the organic layers were washed with water (2×20 mL) and saturated aqueous sodium chloride (20 mL), dried over sodium sulfate, decanted and concentrated in vacuo. The residue was purified by preparative thin layer chromatography (10% ethyl acetate-methylene chloride, two elutions) to afford Compound 25 (0.5 mg, 89%). $R_f$0.16 (10% ethyl acetate-methylene chloride); $^1$H NMR (500 MHz, $CDCl_3$) δ7.73–7.71 (m, 2H), 7.65–7.63 (m, 2H), 5.68 (s, 1H), 5.60 (s, 1H), 5.36 (br s, 1H), 4.28 (s, 1H), 4.25 (t, J=5.3 Hz, 1H), 4.08 (s, 1H), 3.65 (d, J=5.0 Hz, 2H), 3.61 (s, 3H), 3.46 (d, J=8.1 Hz, 1H), 3.22 (d, J=11.5 Hz, 1H), 2.94 (dd, J=18.7, 8.1 Hz, 1H), 2.76 (d, J=15.7 Hz, 1H), 2.69 (d, J=18.4 Hz, 1H), 2.35 (s, 3H), 2.28 (s, 6H), 1.99 (s, 3H), 1.69–1.63 (m, 1H); FTIR (neat) 3412 (m br), 2935 (m br), 2856 (w), 1764 (m), 1717 (s), 1461 (m), 1449 (m), 1431 (m), 1405 (m), 1395 (m), 1369 (m), 1196 (m), 1101 (m), 1075 (m) $cm^{-1}$; HRMS (FAB), [m+Na]/z calc'd for $C_{36}H_{33}O_8N_4BrNa$: 751.1379, found 751.1399.

EXAMPLE 27

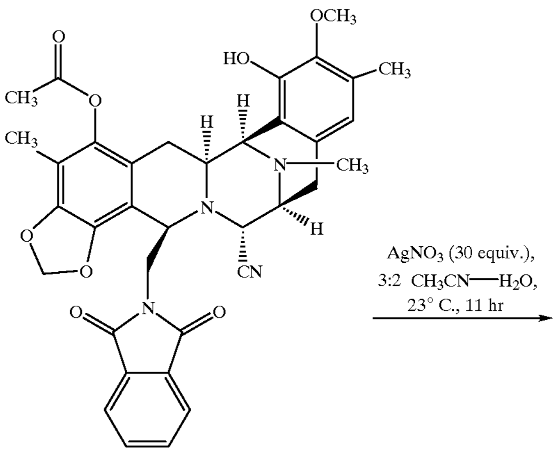

7

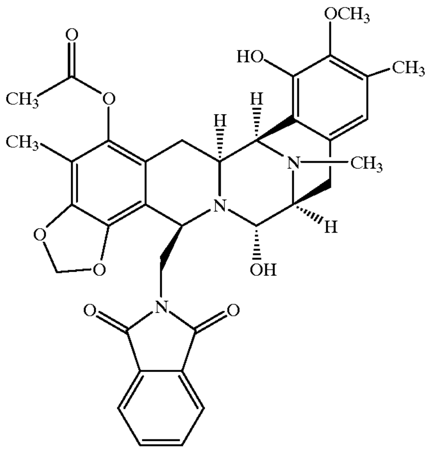

26 (60%)

Phthalimide (7) (0.5 mg, 0.00077 mmol) was dissolved in 3:2 acetonitrile-water (0.25 mL). Silver nitrate (4.0 mg, 0.024 mmol) was added as a solid and the solution was stirred at 23° C. for 11 hr. The reaction was quenched by stirring with a 1:1 mixture of saturated aqueous sodium chloride and saturated aqueous sodium bicarbonate (0.5 mL) for 15 min. The mixture was poured into a 1:1 mixture of saturated aqueous sodium chloride and saturated aqueous sodium bicarbonate (2 mL) and extracted with methylene chloride (3×4 mL), dried over sodium sulfate, filtered through Celite and concentrated in vacuo to afford Compound 26 (0.3 mg, 60%). $^1$H NMR (400 MHz, $CDCl_3$) δ7.72–7.70 (m, 2H), 7.66–7.62 (m, 2H), 6.43 (s, 1H), 5.58 (s, 1H), 5.59 (s, 1H), 5.15 (br s, 1H), 4.65–4.58 (m, 2H), 4.01 (d, J=10.6 Hz, 1H), 3.93 (s, 1H), 3.69–3.50 (m, 5H), 3.26 (d, J=11.8 Hz, 1H), 3.15 (d, J=7.2 Hz, 1H), 2.92 (dd, J=18.2, 8.4 Hz, 1H), 2.71 (d, J=15.2 Hz, 1H), 2.58 (d, J=17.5 Hz, 1H), 2.30 (s, 3H), 2.25 (s, 3H), 2.24 (s, 3H), 1.96 (s, 3H), 1.76–1.67 (m, 1H); FTIR (neat) 3436 (m br), 2960 (m br), 2929 (m br), 2855 (w), 1762 (m), 1716 (s), 1499 (m), 1459 (m), 1432 (m), 1394 (m), 1367 (m), 1293 (w), 1262 (w), 1233 (m), 1199 (m), 1149 (w), 1103 (m), 1073 (m), 1030 (m), 1007 (m), 946 (w) $cm^{-1}$.

EXAMPLE 28

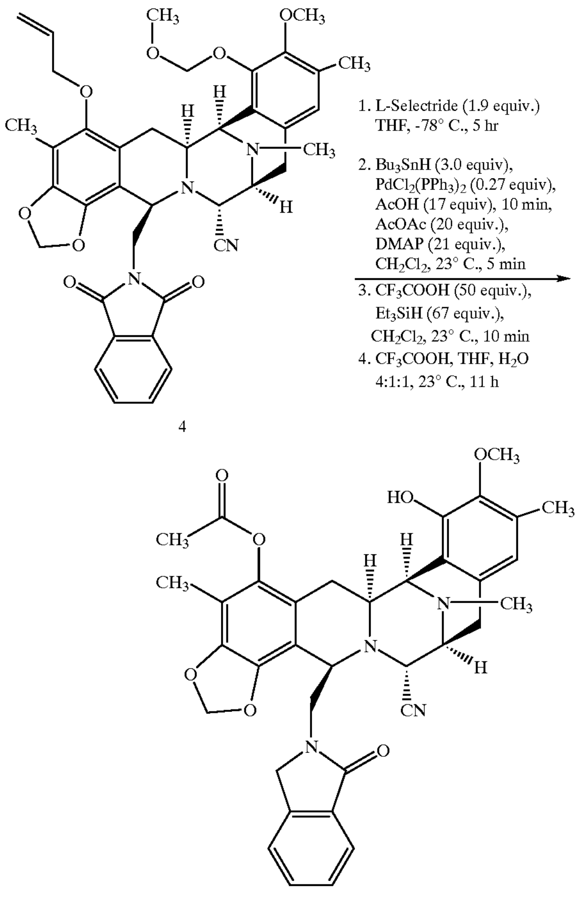

4

27 (44% over 4 steps)

Phthalimide (4) (3.6 mg, 0.0052 mmol) was azeotropically dried with toluene (2x2 mL) and dissolved in THF (0.5 mL). The mixture was cooled to −78° C. in a dry ice-acetone bath and a 1.0 M solution of L-Selectride in THF (10 μL, 0.010 mmol) was added drop-wise. The reaction was warmed to 23° C. slowly over 5 hr and was quenched with 2 drops of 5% acetic acid in water. After stirring at 23° C. for 30 min the reaction was concentrated in vacuo, dissolved in ethyl acetate, passed through a short pad a silica gel using ethyl acetate and concentrated in vacuo. This residue was dissolved in methylene chloride (0.8 mL) and to this solution was added acetic acid (5.0 □L, 0.088 mmol), $PdCl_2(PPh_3)_2$ (1.0 mg, 1.4 μmol) and tributyltin hydride (4.0 μL, 0.015 mmol). Bubbling was observed and the reaction changes from a yellow to a dark orange color. After stirring at 23° C. for 10 min the reaction was charged with 4-dimethylaminopyridine (13.2 mg, 0.11 mmol) and acetic anhydride (10 μL, 0.10 mmol). The reaction was stirred at 23 ° C. for 5 min and purified by flash column chromatography (1 mL silica gel, gradient methylene chloride to 2:1 ethyl acetate-hexane). This residue was further purified by preparative thin layer chromatography (2:1 ethyl acetate-hexane) to afford a 55:45 mixture of isomers (3.2 mg, 84%).

The mixture of compounds (1.9 mg, 0.0026 mmol) was dissolved in methylene chloride (0.5 mL) and the solution treated with triethylsilane (28 μL, 0.175 mmol) and trifluoroacetic acid (10 μL, 0.129 mmol). After stirring at 23° C. for 10 min the reaction was concentrated in vacuo and purified twice by preparative thin layer chromatography (2:1 ethyl acetate-hexane and 5% methanol-methylene chloride) to afford a residue (0.9 mg, 51%).

This material (0.8 mg, 0.0012 mmol) was dissolved in a mixture of trifluoroacetic acid-THF-water (4:1:1 (v/v), 1.2 mL) and the solution was stirred at 23° C. for 11 hr. The reaction mixture was diluted with toluene (1 mL) and the solution was concentrated in vacuo. Additional volatiles were removed by repetitive in vacuo azeotropic concentration from toluene (3x1 mL). The residue was purified by flash column chromatography (1.0 mL silica gel, methylene chloride to 1:1 to 2:1 ethyl acetate-hexane) to afford Compound 27 (0.8 mg, 100%). $R_f$ 0.20 (2:1 ethyl acetate-hexane); $^1$H NMR (400 MHz, $CDCl_3$) δ7.75–7.73 (m, 1H), 7.39–7.35 (m, 2H), 7.08 (d, J=7.2 Hz, 1H), 6.14 (s, 1H), 5.97 (s, 1H), 5.92 (s, 1H), 5.44 (s, 1H), 4.36 (d, J=1.9 Hz, 1H), 4.24 (d, J=4.4 Hz, 1H), 3.97 (d, J=2.3 Hz, 1H), 3.59 (s, 3H), 3.55–3.34 (m, 5H), 3.24 (d, J=11.6 Hz, 1H), 2.89–2.84 (m, 2H), 2.77 (d, J=15.6 Hz, 1H), 2.29 (s, 3H), 2.27 (s, 3H), 2.05 (s, 3H), 1.96 (s, 3H), 1.62–1.60 (m, 1H); FTIR (neat) 3379 (m br), 2932 (m br), 2857 (w), 1759 (s), 1682 (s), 1619 (w), 1588 (w), 1499 (w), 1455 (m), 1434 (m), 1416 (m), 1370 (m), 1327 (w), 1303 (w), 1234 (m), 1199 (s), 1148 (w), 1105 (m), 1085 (m), 1076 (m), 1030 (w), 1000 (w), 956 (w), 913 (w) $cm^{-1}$; HRMS (FAB), [m+Na]/z calc'd for $C_{36}H_{36}O_7N_4Na$: 659.2482, found 659.2488.

EXAMPLE 29

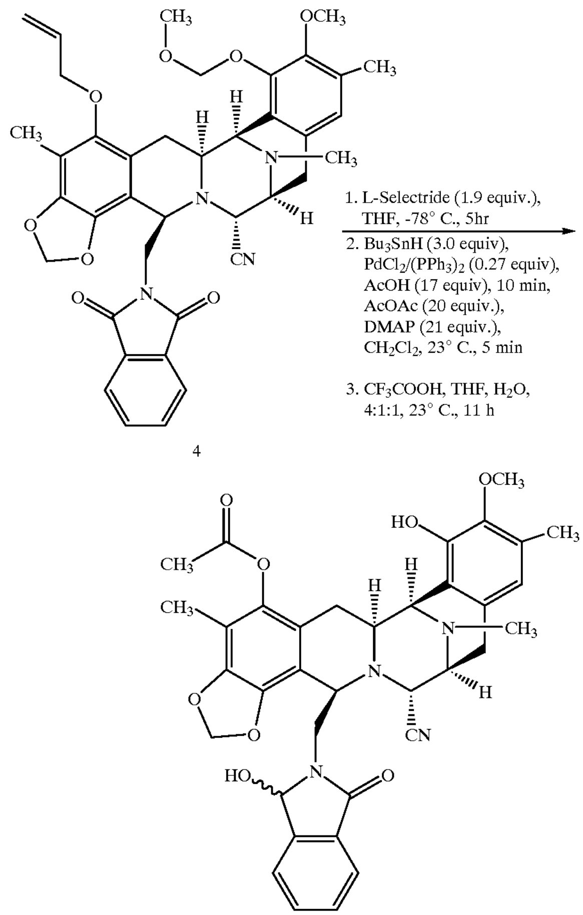

4

28 (39% over 3 steps)
(Only on isomer isolated)

Phthalimide (4) (3.6 mg, 0.0052 mmol) was azeotropically dried with toluene (2x2 mL) and dissolved in THF (0.5 mL). The mixture was cooled to −78° C. in a dry ice-acetone bath and a 1.0 M solution of L-Selectride in THF (10 μL, 0.010 mmol) was added dropwise. The reaction was warmed to 23° C. slowly over 5 hr and was quenched with 2 drops of 5% acetic acid in water. After stirring at 23° C. for 30 min the reaction was concentrated in vacuo, dissolved in ethyl acetate, passed through a short pad a silica gel using ethyl acetate and concentrated in vacuo. This residue was dissolved in methylene chloride (0.8 mL) and to this solution was added acetic acid (5.0 μL, 0.088 mmol), $PdCl_2(PPh_3)_2$ (1.0 mg, 1.4 μmol) and tributyltin hydride (4.0 μL, 0.015 mmol). Bubbling was observed and the reaction changes from a yellow to a dark orange color. After stirring at 23° C. for 10 min the reaction was charged with 4-dimethylaminopyridine (13.2 mg, 0.11 mmol) and acetic anhydride (10 μL, 0.10 mmol). The reaction was stirred at 23° C. for 5 min and purified by flash column chromatography (1 mL silica gel, gradient methylene chloride to 2:1 ethyl acetate-hexane). This residue was further purified by preparative thin layer chromatography (2:1 ethyl acetate-hexane) to afford a 55:45 mixture of isomers (3.2 mg, 84%).

This material (3.0 mg, 0.004 mmol) was dissolved in a mixture of trifluoroacetic acid-THF-water (4:1:1 (v/v), 1.2 mL) and the solution was stirred at 23° C. for 11 h. The reaction mixture was diluted with toluene (1 mL) and the solution was concentrated in vacuo. Additional volatiles were removed by repetitive in vacuo azeotropic concentration from toluene (3x1 mL). The residue was purified by flash column chromatography (1.0 mL silica gel, methylene chloride to 2:1 ethyl acetate-hexane) and then purified by preparative thin layer chromatography (2:1 ethyl acetate-hexane) to afford isomerically pure (28) (1.2 mg, 46%). $R_f$0.18 (2:1 ethyl acetate-hexane); $^1$H NMR (400 MHz, $CDCl_3$) δ7.67 (d, J=6.7 Hz, 1H), 7.44–7.40 (m, 2H), 7.26–7.24 (m, 1H), 6.09 (s, 1H), 5.98 (s, 1H), 5.96 (s, 1H), 5.42 (s, 1H), 4.95 (d, J=9.5 Hz, 1H), 4.34 (d, J=2.3 Hz, 1H), 4.31 (br s, 1H), 4.24 (d, J=4.5 Hz, 1H), 3.96 (d, J=2.2 Hz, 1H), 3.64 (d, J=14.2 Hz, 1H), 3.39–3.12 (m, 6H), 3.25 (dt, J=11.7, 2.7 Hz, 1H), 2.85 (dd, J=18.1, 7.4 Hz, 1H), 2.77 (d, J=17.9 Hz, 1H), 2.29 (s, 3H), 2.26 (s, 3H), 2.07 (s, 3H), 1.91 (s, 3H), 1.79 (d, J=9.6 Hz, 1H); FTIR (neat) 3375 (m br), 2933 (m br), 2857 (w), 2256 (w), 1758 (m), 1686 (s), 1499 (w), 1435 (s), 1370 (m), 1326 (m), 1299 (s), 1292 (s), 1234 (s), 1199 (s), 1147 (w), 1124 (m), 1105 (m), 1084 (s), 1075 (s), 1031 (m), 1008 (m), 953 (m) $cm^{-1}$; HRMS (FAB), [m+Na]/z calc'd for $C_{36}H_{36}O_8N_4Na$: 675.2431, found 675.2439.

-continued

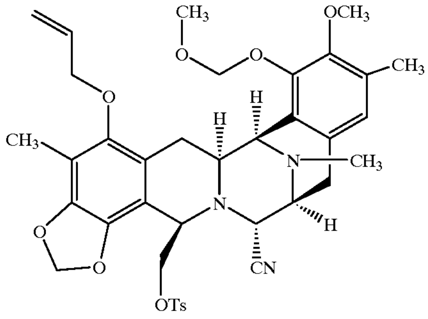

29 (69%)

Alcohol (4) (14.3 mg, 0.025 mmol) was azeotropically dried with toluene (2x1 mL) in vacuo. The residue was dissolved in methylene chloride (0.5 mL) and to this solution was added N,N-diisopropylethylamine (9.0 μL, 0.052 mmol), 4-dimethylaminopyridine (9.4 mg, 0.077 mmol) and p-toluenesulfonic anhydride (29.0 mg, 0.089 mmol). The reaction was stirred at 23° C. for 13 hr and was then quenched into a half-saturated solution of aqueous sodium bicarbonate (10 mL). The mixture was extracted with methylene chloride (3x10 mL) and the organic layers were dried over sodium sulfate, decanted and concentrated in vacuo. The residue was purified by flash column chromatography (10 mL silica gel, 1:1 ethyl acetate-hexane) to afford Compound 29 (12.6 mg, 69% yield). $R_f$0.32 (1:1 ethyl acetate-hexane); $^1$H NMR (500 MHz, $CDCl_3$) δ7.62 (d, J=8.1 Hz, 2H), 7.27 (d, J=7.9 Hz, 2H), 6.70 (s, 1H), 6.10–6.07 (m, 1H), 5.79 (s, 2H), 5.40 (d, J=15.8 Hz, 1H), 5.27 (d, J=10.3 Hz, 1H), 5.13–5.09 (m, 2H), 4.20–4.10 (m, 5H), 3.95 (dd, J=9, 3, 3.0 Hz, 1H), 3.74 (s, 3H), 3.57 (s, 3H), 3.51 (t, J=9.8 Hz, 1H), 3.30 (d, J=8.0 Hz, 1H), 3.22 (d, J=13.6 Hz, 2H), 3.02 (d, J=17.9, 7.9 Hz, 1H), 2.65 (d, J=17.9 Hz, 1H), 2.44 (s, 3H), 2.31 (s, 3H), 2.26 (s, 3H), 2.10 (s, 3H), 1.78 (dd, J=15.7, 12.2 Hz, 1H); $^{13}$C NMR (125 MHz, $CDCl_3$) δ148.6, 148.3, 148.2, 144.7, 144.4, 139.3, 133.7, 132.9, 130.5, 129.7, 127.8, 125.3, 123.7, 121.4, 118.0, 117.7, 113.0, 110.2, 101.2, 99.3, 74.3, 73.5, 61.6, 59.7, 57.7, 57.5, 57.1, 55.9, 55.6, 41.5, 26.2, 25.4, 21.6, 15.8, 9.3; FTIR (neat) 2935 (m br), 2256 (w), 1738 (w), 1600 (w), 1484 (w), 1449 (m), 1402 (w), 1364 (m), 1342 (m), 1295 (w), 1268 (w), 1232 (m), 1189 (m), 1177 (s), 1158 (m), 1096 (s), 1066 (m), 1021 (m), 998 (m), 970 (m), 962 (m), 930 (m) $cm^{-1}$; HRMS (FAB), [m+Na]/z calc'd for $C_{38}H_{43}O_9N_3SNa$: 740.2618, found 740.2649; $[\alpha]_D^{23}$ +78.7° (c 0.97, methylene chloride).

EXAMPLE 30

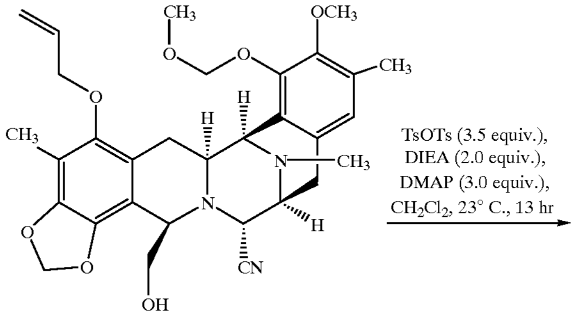

4

EXAMPLE 31

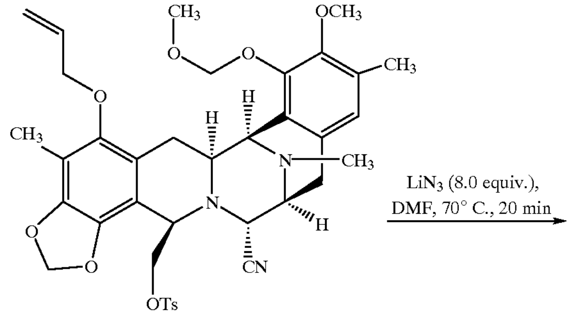

29

-continued

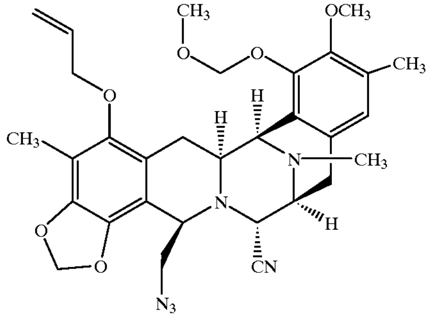

30 (73%)

-continued

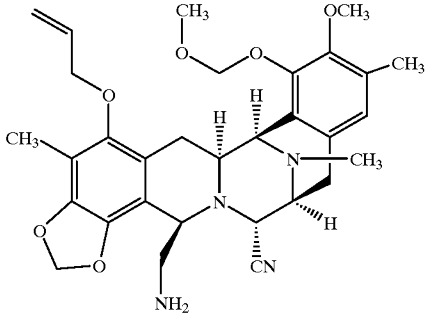

31 (59%)

Tosylate (29) (14.0 mg, 0.020 mmol) was dissolved in DMF (0.5 mL). Lithium azide (7.7 mg, 0.16 mmol) was added and the reaction was placed in a 70° C. oil bath for 20 min. The reaction was cooled to room temperature, diluted with 1:1 ethyl acetate-hexane (20 mL) and washed with water (3x20 mL) and saturated aqueous sodium chloride (20 mL). The organic layers were dried over sodium sulfate, decanted and concentrated in vacuo. The residue was purified by preparative thin layer chromatography (2:1 diethyl ether-hexane, two elutions) to afford Compound 30 (8.4 mg, 73% yield). $R_f$0.43 (1:1 ethyl acetate-hexane); $^1$H NMR (400 MHz, $CDCl_3$) δ6.61 (s, 1H), 6.15–6.08 (m, 1H), 5.94 (d, J=1.4 Hz, 1H), 5.87 (d, J=1.4 Hz, 1H), 5.41 (dq, J=17.2, 1.5 Hz, 1H), 5.28 (ddd, J=11.5, 1.6, 1.1 Hz, 1H), 5.14 (d, J=5.9 Hz, 1H), 5.11 (d, J=5.9 Hz, 1H), 4.24–4.12 (m, 4H), 4.01 (dd, J=7.1, 2.9 Hz, 1H), 3.73 (s, 3H), 3.58 (s, 3H), 3.40 (dd, J=12.1, 3.0 Hz, 1H), 3.35 (d, J=7.6 Hz, 1H), 3.27 (dd, J=6.7, 2.6 Hz, 1H), 3.24 (d, J=2.6 Hz, 1H), 3.12–3.02 (m, 2H), 2.63 (d, J=17.9 Hz, 1H), 2.33 (s, 3H), 2.22 (s, 3H), 2.13 (s, 3H), 1.89 (dd, J=15.8, 12.1 Hz, 1H); $^{13}$C NMR (100 MHz, $CDCl_3$) δ148.6, 148.4, 148.3, 144.4, 139.0, 133.7, 130.6, 130.2, 125.4, 123.7, 121.3, 118.1, 117.7, 112.7, 112.4, 101.2, 99.3, 74.2, 61.3, 59.7, 57.7, 57.1, 56.9, 56.5, 55.5, 41.5, 26.3, 25.6, 15.7, 9.3; FTIR (neat) 2934 (s br), 2857 (m), 2105 (s), 1725 (w), 1650 (w), 1613 (w), 1581 (w), 1484 (m), 1444 (s), 1342 (m), 1323 (m), 1302 (m), 1269 (m), 1232 (m), 1158 (m), 1104 (s), 1096 (m), 1078 (m), 1024 (m), 999 (s), 977 (m), 928 (m), 914 (m) $cm^{-1}$; HRMS (FAB), [m+Na]/z calc'd for $C_{31}H_{36}O_6N_6Na$: 611.2594, found 611.2613; $[\alpha]_D^{23}$+71.0° (c 0.73, methylene chloride).

Azide (30) was dissolved in nitrogen degassed methanol (0.5 mL). To the solution was added triethylamine (21 μL, 0.15 mmol) and dithiothreitol (24.0 mg, 0.16 mmol). The reaction was stirred at 23° C. for 17 hr and then concentrated in vacuo. The residue was dissolved in ethyl acetate (20 mL) and washed with water (20 mL). The aqueous layer was extracted with ethyl acetate (20 mL) and the combined organic layers were washed with saturated aqueous sodium chloride (20 mL), dried over sodium sulfate, decanted and concentrated in vacuo. The residue was purified by flash column chromatography (5 mL silica gel, gradient diethyl ether to 5% methanol-methylene chloride) to afford Compound 31 (4.9 mg, 59% yield). $R_f$0.10 (5% methanol-methylene chloride); $^1$H NMR (400 MHz, $CDCl_3$) δ6.70 (s, 1H), 6.14–6.10 (m, 1H), 5.93 (d, J=1.4 Hz, 1H), 5.86 (d, J=1.4 Hz, 1H), 5.40 (dd, J=17.1, 1.5 Hz, 1H), 5.27 (dd, J=10.3, 1.4 Hz, 1H), 5.12 (s, 2H), 4.23 (d, J=2.0 Hz, 1H), 4.22–4.18 (m, 1H), 4.14 (dd, J=12.1, 5.8 Hz, 1H), 3.99 (d, J=2.5 Hz, 1H), 3.91 (s, 1H), 3.71 (s, 3H), 3.59 (s, 3H), 3.37 (d, J=7.3 Hz, 1H), 3.28 (dt, J=11.7, 2.7 Hz, 1H), 3.21 (dd, J=15.8, 2.7 Hz, 1H), 3.09 (dd, J=17.9, 8.0 Hz, 1H), 2.76 (dd, J=17.7, 2.5 Hz, 1H), 2.71 (dd, J=13.7, 3.3 Hz, 1H), 2.49 (d, J=17.9 Hz, 1H), 2.35 (s, 3H), 2.21 (s, 3H), 2.13 (s, 3H), 1.81 (dd, J=15.7, 11.8 Hz, 1H), 1.34 (br s, 2H); $^{13}$C NMR (100 MHz, $CDCl_3$) δ148.6, 148.43, 148.37, 144.5, 138.8, 133.8, 130.8, 130.0, 125.1, 124.0, 121.3, 117.9, 117.6, 113.7, 112.2, 101.1, 99.3, 74.1, 59.9, 59.8, 58.9, 57.7, 57.1, 56.3, 55.3, 44.2, 41.7, 26.5, 25.7, 15.8, 9.3; FTIR (neat) 3100 (v/v br), 2934 (m br), 2860 (w), 1484 (w), 1446 (m), 1432 (m), 1385 (m), 1376 (w), 1341 (m), 1323 (w), 1299 (w), 1269 (m), 1233 (w), 1158 (m), 1103 (s), 1075 (m), 1064 (m), 1042 (m), 1023 (s), 998 (m), 977 (m), 964 (m), 927 (m) $cm^{-1}$; HRMS (FAB), [m+Na]/z calc'd for $C_{31}H_{38}O_6N_4Na$: 585.2689, found 585.2693; $[\alpha]_D^{23}$ +86.8° (c 0.41, methylene chloride).

EXAMPLE 32

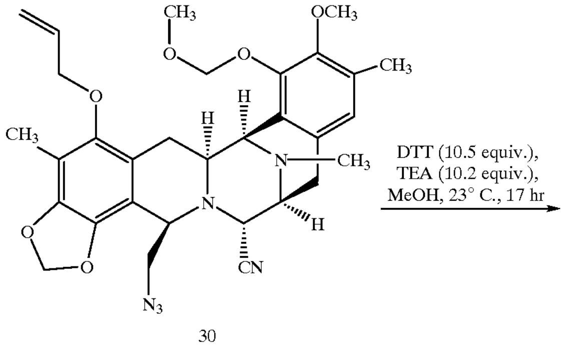

30

EXAMPLE 33

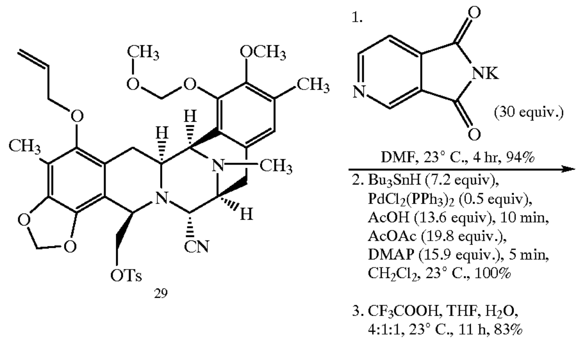

29

-continued

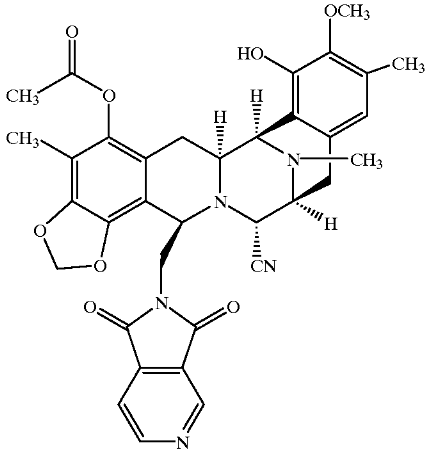

32 (78% over 3 steps)

Tosylate (29) (1.0 mg, 0.0014 mmol) was dissolved in a saturated solution of potassium 4-pyridinedicarboimide (0.2 mL, ~30 equiv.). After stirring at 23° C. for 4 hr the reaction was diluted with 1:1 ethyl acetate-hexane (10 mL) and washed with water (10 mL). The aqueous was extracted with 1:1 ethyl acetate-hexane (10 mL) and the combined organic layers were washed with saturated aqueous sodium chloride (10 mL), dried over sodium sulfate, decanted and concentrated in vacuo. The residue was purified by flash column chromatography (1.0 mL silica gel, gradient methylene chloride to 2:1 diethyl ether-hexane) to afford a residue (0.9 mg, 94%).

This material was dissolved in methylene chloride (0.3 mL) and to this solution was added acetic acid (1.0 μL, 0.018 mmol), $PdCl_2(PPh_3)_2$ (0.5 mg, 0.6 μmol) and tributyltin hydride (2.5 μL, 0.0093 mmol). Bubbling was observed and the reaction changes from a yellow to a dark orange color. After stirring at 23° C. for 10 min the reaction was charged with 4-dimethylaminopyridine (2.5 mg, 0.020 mmol) and acetic anhydride (2.5 μL, 0.025 mmol). The reaction was stirred at 23° C. for 5 min and purified by preparative thin layer chromatography (2:1 ethyl acetate-hexane) to afford a residue (0.9 mg, 100 %).

This material was dissolved in a mixture of trifluoroacetic acid-THF-water (4:1:1 (v/v), 1.2 mL) and the solution was stirred at 23° C. for 11 hr. The reaction mixture was diluted with toluene (1 mL) and the solution was concentrated in vacuo. Additional volatiles were removed by repetitive in vacuo azeotropic concentration from toluene (3×1 mL). The residue was purified by flash column chromatography (1.0 mL silica gel, gradient methylene chloride to 2:1 diethyl ether-hexane to ethyl acetate) and then by preparative thin layer chromatography (2:1 ethyl acetate-hexane, two elutions) to afford Compound 32 (0.7 mg, 83%). $R_f$ 0.14 (2:1 ethyl acetate-hexane); $^1H$ NMR (400 MHz, $C_6D_6$) δ8.75 (s, 1H), 8.27 (d, J=4.8 Hz, 1H), 6.91 (s, 1H), 6.39 (s, 1H), 5.31 (br s, 1H), 5.24 (s, 1H), 5.01 (br s, 1H), 4.47 (d, J=3.7 Hz, 1H), 3.93 (d, J=2.2 Hz, 1H), 3.81–3.76 (m, 2H), 3.62 (dd, J=13.9, 5.5 Hz, 1H), 3.37 (d, J=11.4 Hz, 1H), 2.99 (s, 3H), 2.86 (d, J=4.2 Hz, 1H), 2.79 (d, J=17.1 Hz, 1H), 2.62–2.60 (m, 2H), 2.16 (s, 3H), 2.08 (s, 3H), 2.01 (s, 3H), 1.76 (s, 3H), 1.59 (m, 1H); FTIR (neat) 3431 (w br), 2935 (m br), 2856 (w), 1761 (m), 1723 (s), 1615 (w), 1499 (m), 1434 (m), 1388 (m), 1369 (w), 1327 (w), 1301 (w), 1294 (m), 1268 (m), 1234 (m), 1197 (m), 1145 (m), 1137 (m), 1100 (m), 1074 (m), 1030 (m), 1007 (m), 997 (m), 947 (m) $cm^{-1}$; HRMS (FAB), [m+Na]/z calc'd for $C_{35}H_{33}O_8N_5Na$: 674.2227, found 674.2237.

EXAMPLE 34

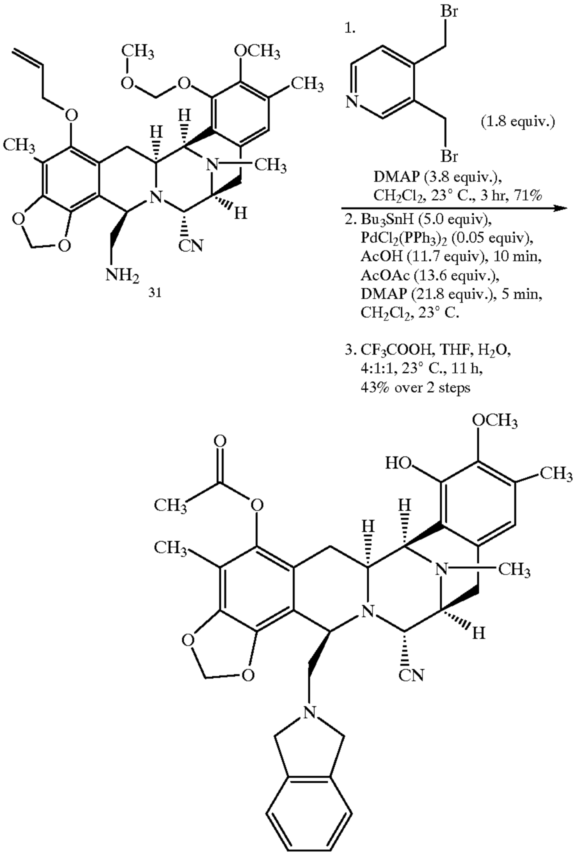

33 (31% over 3 steps)

Amine (31) (0.6 mg, 0.0011 mmol) was dissolved in methylene chloride (0.5 mL). To this mixture was added 4-dimethylaminopyridine (0.5 mg, 0.0041 mmol) and α,α-dibromoxylene (0.5 mg, 0.0019 mmol). After stirring at 23° C. for 3 hr the reaction was purified by flash column chromatography (0.6 mL silica gel, gradient methylene chloride to 1:1 ethyl acetate-hexane) to afford a film (0.5 mg, 71%).

This residue was dissolved in methylene chloride (0.5 mL) and to this solution was added acetic acid (0.5 μL, 0.0088 mmol), $PdCl_2(PPh_3)_2$ (0.02 mg, 0.04 μmol) and tributyltin hydride (1.0 μL, 0.0037 mmol). Bubbling was observed and the reaction changes from a yellow to a dark orange color. After stirring at 23° C. for 10 min the reaction was charged with 4-dimethylaminopyridine (2.0 mg, 0.016 mmol) and acetic anhydride (1.0 μL, 0.010 mmol). The reaction was stirred at 23° C. for 5 min and purified by preparative thin layer chromatography (1:1 ethyl acetate-hexane, three elutions).

This material was dissolved in a mixture of trifluoroacetic acid-THF-water (4:1:1 (v/v), 0.5 mL) and the solution was stirred at 23° C. for 11 hr. The reaction mixture was diluted with toluene (1 mL) and the solution was concentrated in vacuo. Additional volatiles were removed by repetitive in vacuo azeotropic concentration from toluene (3×1 mL). The residue was purified by preparative thin layer chromatography (2:1 ethyl acetate-hexane, two elutions) to afford Compound 33 (0.2 mg, 43% over two steps). $R_f$ 0.43 (2:1 ethyl acetate-hexane); $^1H$ NMR (500 MHz, $CDCl_3$) δ7.20–7.19 (m, 4H), 6.46 (s, 1H), 5.95 (d, J=1.2 Hz, 1H), 5.91 (d, J=1.3 Hz, 1H), 5.64 (s, 1H), 4.94 (br s, 1H), 4.10 (d, J=8.3 Hz, 1H), 4.07 (s, 1H), 3.99 (d, J=11.9 Hz, 2H), 3.87 (d, J=11.4 Hz, 2H), 3.77 (s, 3H), 3.26 (d, J=12.0 Hz, 1H), 3.20 (d, J=7.2 Hz, 1H), 2.91 (dd, J=17.7, 8.1 Hz, 1H), 2.87 (d, J=12.6 Hz, 1H), 2.79 (d, J=16.6 Hz, 1H), 2.75–2.71 (m, 1H), 2.59 (d, J=17.8 Hz, 1H), 2.33 (s, 3H), 2.30 (s, 3H), 2.26 (s, 3H), 2.00 (s, 3H), 1.91 (dd, J=16.1, 11.2 Hz, 1H); FTIR (neat) 3406 (w br), 2927 (s), 2854 (m), 1762 (m), 1719 (m), 1459 (m), 1500 (w), 1432 (m), 1370 (m), 1325 (w), 1294 (w), 1233 (m), 1199 (s), 1144 (m), 1105 (m), 1085 (m), 1074 (m), 1029 (m), 1006 (w) $cm^{-1}$; HRMS (FAB), [m+H]/z calc'd for $C_{36}H_{39}O_6N_4$: 623.2870, found 623.2878.

EXAMPLE 35

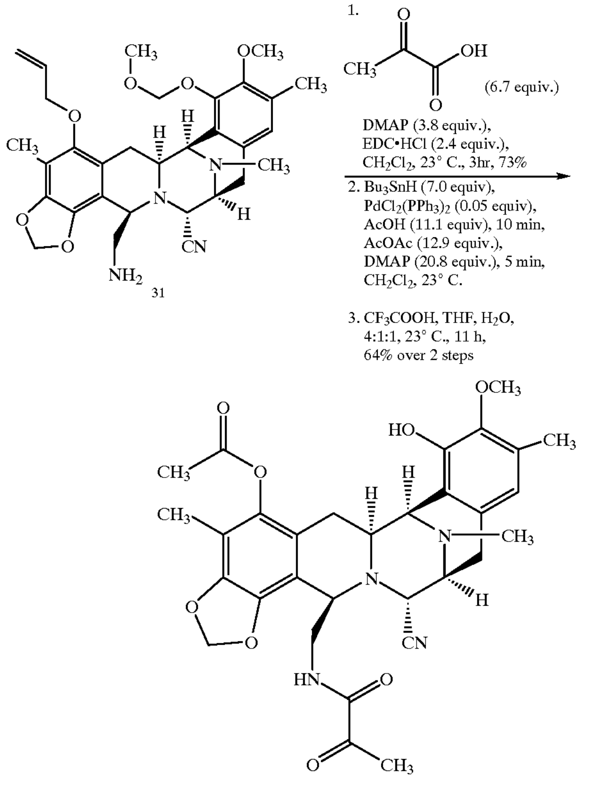

31

34 (48% over 3 steps)

Amine (31) (0.6 mg, 0.0011 mmol) was dissolved in methylene chloride (0.5 mL). To this mixture was added 4-dimethylaminopyridine (0.5 mg, 0.0041 mmol), pyruvic acid (0.5 μL, 0.0072 mmol) and 1-(3-dimethylaminopropyl)-3-ethylcarbodiimide hydrochloride (0.5 mg, 0.0026 mmol). After stirring at 23° C. for 3 hr the reaction was purified by flash column chromatography (0.6 mL silica gel, gradient methylene chloride to 1:1 ethyl acetate-hexane) to afford a film (0.5 mg, 73%).

This residue was dissolved in methylene chloride (0.5 mL) and to this solution was added acetic acid (0.5 μL, 0.0088 mmol), $PdCl_2(PPh_3)_2$ (0.02 mg, 0.04 μmol) and tributyltin hydride (1.5 μL, 0.0056 mmol). Bubbling was observed and the reaction changes from a yellow to a dark orange color. After stirring at 23° C. for 10 min the reaction was charged with 4-dimethylaminopyridine (2.0 mg, 0.016 mmol) and acetic anhydride (1.0 μL, 0.010 mmol). The reaction was stirred at 23° C. for 5 min and purified by preparative thin layer chromatography (1:1 ethyl acetate-hexane, three elutions).

This material was dissolved in a mixture of trifluoroacetic acid-THF-water (4:1:1 (v/v), 0.5 mL) and the solution was stirred at 23° C. for 11 hr. The reaction mixture was diluted with toluene (1 mL) and the solution was concentrated in vacuo. Additional volatiles were removed by repetitive in vacuo azeotropic concentration from toluene (3×1 mL). The residue was purified by preparative thin layer chromatography (2:1 ethyl acetate-hexane, two elutions) to afford Compound 34 (0.3 mg, 64% over two steps). $R_f$0.30 (2:1 ethyl acetate-hexane); $^1H$ NMR (500 MHz, $CDCl_3$) δ6.45 (s, 1H), 6.42 (br s, 1H), 5.99 (d, J=1.1 Hz, 1H), 5.93 (d, J=1.2 Hz, 1H), 5.66 (s, 1H), 4.08–4.06 (m, 2H), 4.01 (d, J=2.4 Hz, 1H), 3.79 (s, 3H), 3.46–3.42 (m, 2H), 3.35 (d, J=7.8 Hz, 1H), 3.25 (d, J=11.7 Hz, 1H), 3.03 (dd, J=18.1, 8.5 Hz, 1H), 2.79 (d, J=14.1 Hz, 1H), 2.56 (d, J=17.7 Hz, 1H), 2.31 (s, 3H), 2.30 (s, 3H), 2.26 (s, 3H), 2.21 (s, 3H), 2.00 (s, 3H), 1.77 (t, J=13.6 Hz, 1H); FTIR (neat) 3382 (m br), 2929 (m br), 2854 (w), 1761 (m), 1735 (m), 1721 (m), 1687 (s), 1519 (w), 1509 (w), 1500 (w), 1458 (m), 1417 (m), 1368 (m), 1325 (w), 1294 (w), 1233 (m), 1199 (s), 1155 (m), 1108 (m), 1087 (m), 1030 (w), 1006 (w), 956 (w) $cm^{-1}$; HRMS (FAB), [m+Na]/z calc'd for $C_{31}H_{34}O_8N_4Na$: 613.2274, found 613.2195.

EXAMPLE 36

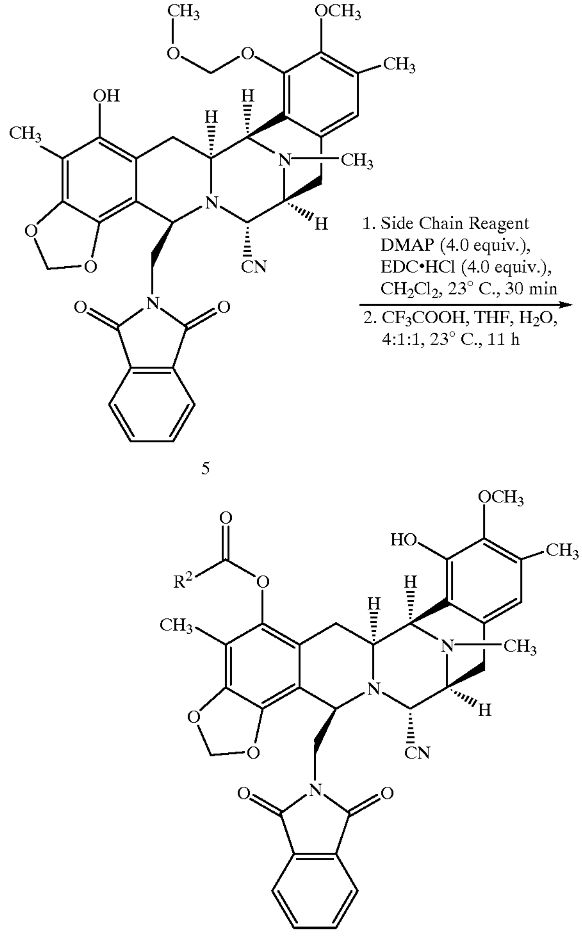

5

35–39

TABLE 2

General procedure for the EDC-HCl Coupling of Carboxylic to phenol (5).

| Entry | Cmpd # | Side Chain Reagent | Stoichiometry (equiv.) | Coupling Yield (%) | MOM Removal Yield (%) |
|---|---|---|---|---|---|
| 1 | 35 | 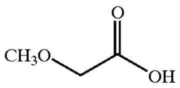 | 70 | 100 | 82 |
| 2 | 36 | 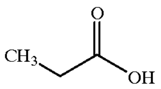 | 4.5 | 94 | 100 |
| 3 | 37 | 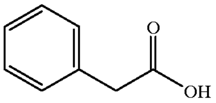 | 5.9 | 95 | 96 |
| 4 | 38 | 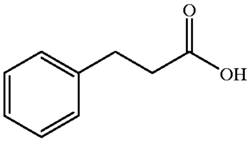 | 4.9 | 93 | 96 |
| 5 | 39 | 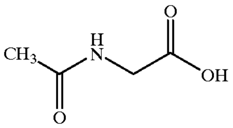 | 6.8 | 55 | 100 |

Phenol (5) (1.0 mg, 0.0015 mmol) was dissolved in a 0.0126 M solution of 1-(3-dimethylaminopropyl)-3-ethylcarbodiimide hydrochloride and 4-dimethylaminopyridine in methylene chloride (0.5 mL, 0.0064 mmol of each). The carboxylic acid was added and the reaction was stirred at 23° C. for 30 min and then quenched into a saturated solution of aqueous sodium bicarbonate (2 mL). The mixture was extracted with methylene chloride (2x5 mL) and the organic layers were dried over sodium sulfate, decanted and concentrated in vacuo. The residue was purified by flash column chromatography (1 mL silica gel, gradient methylene chloride to 1:1 to 2:1 ethyl acetate-hexane) to afford the corresponding phenolic esters. This material was dissolved in a mixture of trifluoroacetic acid-THF-water (4:1:1 (v/v), 1.0 mL) and the solution was stirred at 23° C. for 11 h. The reaction mixture was diluted with toluene (1 mL) and the solution was concentrated in vacuo. Additional volatiles were removed by repetitive in vacuo azeotropic concentration from toluene (3x1 mL). The residue was purified by flash column chromatography (1 mL silica gel, gradient methylene chloride to 2:1 ethyl acetate-hexane to ethyl acetate)[8] to afford the desired product.

[8] Entry 5 was purified using 5% methanol-methylene chloride as the eluent.

EXAMPLE 37

Compound 35—$R_f$0.30 (1:1 ethyl acetate-hexane); $^1$H NMR (400 MHz, $CDCl_3$) α 77.2–7.69 (m, 2H), 7.67–7.64 (m, 2H), 6.39 (s, 1H), 5.69 (s, 1H), 5.60 (s, 1H), 5.38 (br s, 1H), 4.36–4.22 (m, 4H), 4.00 (d, J=1.9 Hz, 1H), 3.67 (d, J=5.2 Hz, 2H), 3.61 (s, 3H), 3.55 (s, 3H), 3.36 (d, J=8.3 Hz, 1H), 3.19 (d, J=12.0 Hz, 1H), 3.02 (dd, J=18.0, 8.3 Hz, 1H), 2.73 (dd, J=15.6, 2.3 Hz, 1H), 2.68 (d, J=18.3 Hz, 1H), 2.29 (s, 3H), 2.21 (s, 3H), 2.00 (s, 3H), 1.73 (dd, J=15.4, 12.3 Hz, 1H); FTIR (neat) 3420 (w), 2933 (m), 2872 (w), 2854 (w), 1774 (m), 1716 (s), 1432 (m), 1394 (m), 1118 (m), 1105 (m), 1071 (m), 1231 (m), 1162 (m) $cm^{-1}$; HRMS (FAB), [m+Na]/z calc'd for $C_{37}H_{36}O_9N_4Na$: 703.2380, found 703.2373.

EXAMPLE 38

Compound 36—$R_f$ 0.52 (2:1 ethyl acetate-hexane); $^1$H NMR (400 MHz, $CDCl_3$) α 7.74–7.71 (m, 2H), 7.68–7.65 (m, 2H), 6.39 (s, 1H), 5.65 (s, 1H), 5.57 (s, 1H), 5.27 (br s, 1H), 4.25–4.23 (m, 2H), 4.06 (s, 1H), 3.65 (s, 3H), 3.63–3.61 (m, 2H), 3.38 (d, J=6.2 Hz, 1H), 3.22 (d, J=12.0 Hz, 1H), 3.03 (dd, J=17.9, 8.0 Hz, 1H), 2.77 (d, J=14.1 Hz, 1H), 2.66 (d, J=18.1 Hz, 1H), 2.60 (q, J=7.6 Hz, 2H), 2.31 (s, 3H), 2.22 (s, 3H), 1.97 (s, 3H), 1.79–1.72 (m, 1H), 1.31 (t, J=7.6 Hz, 3H); FTIR (neat) 3450 (m br), 2979 (w), 2935 (m br), 1771 (w), 1759 (m), 1716 (s), 1460 (m), 1432 (m), 1418 (m), 1394 (m), 1234 (m), 1191 (m), 1144 (m), 1102 (m), 1089 (m), 1070 (m) $cm^{-1}$; HRMS (FAB), [m+Na]/z calc'd for $C_{37}H_{36}O_8N_4Na$: 687.2431, found 687.2421.

EXAMPLE 39

Compound 37—$R_f$ 0.60 (2:1 ethyl acetate-hexane); $^1$H NMR (400 MHz, $CDCl_3$) α 7.73–7.69 (m, 2H), 7.67–7.64 (m 2), 7.47–7.36 (m, 5H), 6.35 (s, 1H), 5.63 (s, 1H), 5.25 (br s, 1H), 5.13 (br s, 1H), 4.22–4.19 (m, 2H), 3.94 (d, J=2.3 Hz, 1H), 3.86 (s, 2H), 3.60–3.58 (m, 2H), 3.53 (br s, 3H), 3.33 (d, J=8.2 Hz, 1H), 3.16 (d, J=12.0 Hz, 1H), 3.00 (dd, J=17.9, 8.1 Hz, 1H), 2.67 (d, J=15.6 Hz, 1H), 2.60 (d, J=18.1 Hz, 1H), 2.27 (s, 3H), 2.19 (s, 3H), 1.89 (s, 3H), 1.68–1.61 (m, 1H); FTIR (neat) 3429 (m br), 2932 (m br), 2856 (w), 1761 (w), 1735 (m), 1715 (s), 1498 (w), 1456 (m), 1432 (m), 1395 (m), 1324 (m), 1296 (w), 1233 (m), 1191 (w), 1120 (ml, 1104 (m), 1083 (m), 1071 (m), 1029 (w), 1004 (w), 946 (w)

$cm^{-1}$; HRMS (FAB), [m+Na]/z calc'd for $C_{42}H_{38}O_8N_4Na$: 749.2587, found 749.2577.

EXAMPLE 40

Compound 38—$R_f$ 0.61 (2:1 ethyl acetate-hexane); $^1H$ NMR (400 MHz, $CDCl_3$) α 7.74–7.72 (m, 2H), 7.67–7.65 (m, 2H), 7.37–7.24 (m, 5H), 6.38 (s, 1H), 5.63 (s, 1H), 5.50 (s, 1H), 5.25 (br s, 1H), 4.25–4.21 (m, 2H), 4.01 (d, J=2.1 Hz, 1H), 3.64 (s, 3H), 3.62–3.60 (m, 2H), 3.34 (d, J=8.1 Hz, 1H), 3.20 (d, J=1.02 Hz, 1H), 3.13–3.08 (m, 2H), 3.02 (dd, J=18.1, 8.0 Hz, 1H), 2.92–2.88 (m, 2H), 2.76 (d, J=14.8 Hz, 1H), 2.63 (d, J=18.0 Hz, 1H), 2.29 (s, 3H), 2.22 (s, 3H), 1.87 (s, 3H), 1.76 (dd, J=15.2, 12.0 Hz, 1H); FTIR (neat) 3427 (m br), 2934 (m br), 2858 (w), 1758 (m), 1716 (s), 1455 (m), 1432 (m), 1395 (m), 1350 (w), 1316 (w), 1256 (m), 1132 (m), 1104 (m) $cm^{-1}$; HRMS (FAB), [m+Na]/z calc'd for $C_{43}H_{40}O_8N_4Na$: 763.2744, found 763.2755.

EXAMPLE 41

Compound 39—$R_f$ 0.17 (4:1 ethyl acetate-hexane); $^1H$ NMR (500 MHz, $CDCl_3$) α 7.73–7.71 (m, 2H), 7.67–7.64 (m, 2H), 6.36 (s, 1H), 6.00 (s, 1H), 5.65 (d, J=1.4 Hz, 1H), 5.27 (d, J=1.4 Hz, 1H), 4.70 (br s, 1H), 4.27 (d, J=2.3 Hz, 1H), 4.22 (t, J=6.2 Hz, 1H), 4.11 (s, 1H), 4.01 (s, 1H), 3.68–3.62 (m, 5H), 3.35 (d, J=7.3 Hz, 1H), 3.17 (d, J=11.8 Hz, 1H), 3.03 (dd, J=18.0, 8.2 Hz, 1H), 2.85 (d, J=14.3 Hz, 1H), 2.63 (d, J=17.9 Hz, 1H), 2.32 (s, 3H), 2.20 (s, 3H), 2.14 (s, 3H), 1.99 (s, 3H), 1.70 (dd, J=15.4, 12.2 Hz, 1H); FTIR (neat) 3382 (m br), 2934 (m br), 1774 (m), 1716 (s), 1673 (m), 1538 (w), 1500 (w), 1459 (m), 1432 (m), 1419 (m), 1396 (m), 1377 (m), 1293 (w), 1234 (m), 1153 (m), 1133 (m), 1103 (m), 1072 (m), 1031 (w), 944 (w) $cm^{-1}$; HRMS (FAB), [m+Na]/z calc'd for $C_{38}H_{37}O_9N_5Na$: 730.2489, found 730.2492.

EXAMPLE 42

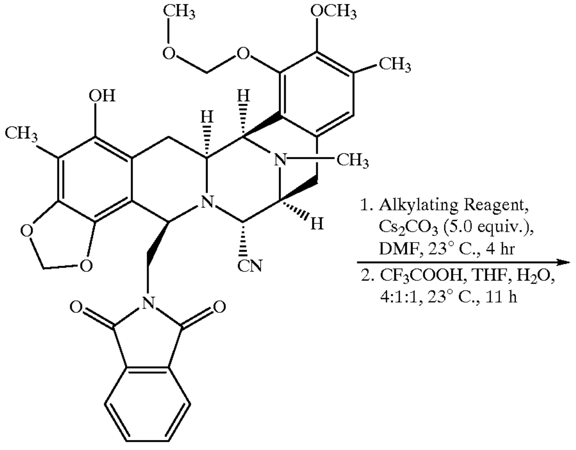

5

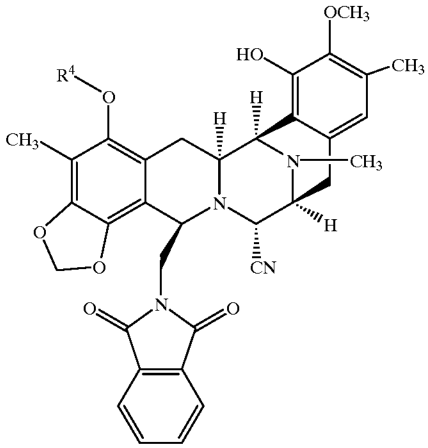

40–42

TABLE 3

General Procedure for the Alkylation of Phenol (5).

| Entry | Cmpd # | Alkylating Reagent | Stoichiometry (equiv.) | Alkylation Yield (%) | MOM Removal Yield (%) |
|---|---|---|---|---|---|
| 1 | 40 | 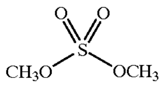 | 5.7 | 92 | 90 |
| 2 | 41 | 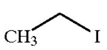 | 5.7 | 48 | 100 |
| 3 | 42 | 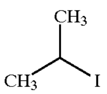 | 5.9 | 75 | 100 |

Phenol (5) (1.0 mg, 0.0015 mmol) was azeotropically dried with toluene (2x1 mL) in vacuo and dissolved in DMF (0.1 mL). Cesium carbonate (3.0 mg, 0.0092 mmol) was gently flame dried in vacuo, cooled and added as a solid to the reaction mixture. The alkylation agent was added via syringe and the solution was stirred at 23° C. for 4 hr and then quenched into a saturated solution of aqueous sodium bicarbonate (2 mL). The mixture was extracted with 1:1 ethyl acetate-hexane (2x5 mL) and the organic layers were dried over sodium sulfate, decanted and concentrated in vacuo. The residue was purified by preparative thin layer chromatography (2:1 ethyl acetate-hexane, one elution). This material was dissolved in a mixture of trifluoroacetic acid-THF-water (4:1:1 (v/v), 1.0 mL) and the solution was stirred at 23° C. for 11 hr. The reaction mixture was diluted with toluene (1 mL) and the solution was concentrated in vacuo. Additional volatiles were removed by repetitive in vacuo azeotropic concentration from toluene (3x1 mL). The residue was purified by flash column chromatography (1 mL silica gel, gradient methylene chloride to 2:1 ethyl acetate-hexane) to afford the desire product.

EXAMPLE 43

Compound 40—$R_f$ 0.43 (2:1 ethyl acetate-hexane); $^1H$ NMR (500 MHz, $CDCl_3$) δ7.73–7.72 (m, 2H), 7.67–7.66 (m, 2H), 6.40 (s, 1H), 5.67 (s, 1H), 5.56 (d, J=1.5 Hz, 1H), 5.10 (d, J=1.5 Hz, 1H), 4.22–4.19 (m, 2H), 4.10 (d, J=2.0 Hz, 1H), 3.70 (s, 3H), 3.61 (s, 3H), 3.59–3.51 (m, 2H), 3.35 (d, J=8.3 Hz, 1H), 3.24–3.19 (m, 2H), 3.05 (dd, J=18.1, 8.2 Hz, 1H), 2.63 (d, J=17.9 Hz, 1H), 2.31 (s, 3H), 2.25 (s, 3H), 2.09 (s, 3H), 1.85 (dd, J=15.7, 12.2 Hz, 1H); FTIR (neat) 3428 (w br), 2935 (m br), 1774 (m), 1716 (s), 1619 (w), 1588 (w), 1499 (w), 1432 (m), 1423 (m), 1396 (m), 1324 (m), 1301 (m), 1266 (m), 1233 (m), 1191 (m), 1145 (w), 1101 (m), 1066 (m), 1028 (m), 998 (m), 948 (m) $cm^{-1}$; HRMS (FAB), [m+Na]/z calc'd for $C_{35}H_{34}O_7N_4Na$: 645.2325, found 645.2325.

EXAMPLE 44

Compound 41—$R_f$ 0.45 (2:1 ethyl acetate-hexane); $^1H$ NMR (400 MHz, $CDCl_3$) δ7.72–7.65 (m, 4H), 6.41 (s, 1H), 5.65 (s, 1H), 5.57 (d, J=1.4 Hz, 1H), 5.11 (d, J=1.4 Hz, 1H), 4.22–4.19 (m, 2H), 4.08 (s, 1H), 3.73 (q, J=7.0 Hz, 2H), 3.68 (s, 3H), 3.62–3.53 (m, 2H), 3.35 (d, J=8.2 Hz, 1H), 3.25–3.17 (m, 2H), 3.05 (dd, J=18.2, 8.2 Hz, 1H), 2.65 (d, J=18.0 Hz, 1H), 2.31 (s, 3H), 2.24 (s, 3H), 2.09 (s, 3H), 1.80 (dd, J=15.3, 11.6 Hz, 1H), 1.35 (t, J=7.0 Hz, 3H); FTIR (neat) 3412 (m br), 2930 (m br), 1773 (m), 1716 (s), 1619 (w), 1588 (w), 1500 (w), 1455 (m), 1395 (m), 1386 (m), 1370 (m), 1265 (m), 1233 (m), 1145 (m), 1101 (m), 1066 (m), 1028 (m), 1006 (m), 950 (m) $cm^{-1}$; HRMS (FAB), [m+Na]/z calc'd for $C_{36}H_{36}O_7N_4Na$: 659.2482, found 659.2477.

EXAMPLE 45

Compound 42—$R_f$0.53 (2:1 ethyl acetate-hexane); $^1H$ NMR (400 MHz, $CDCl_3$) δ7.69–7.63 (m, 4H), 6.43 (s, 1H), 5.62–5.61 (m, 2H), 5.18 (d, J=1.5 Hz, 1H), 4.23–4.20 (m, 2H), 4.07 (d, J=2.5 Hz, 1H), 3.93 (m, 1H), 3.62 (m, 5H), 3.35 (d, J=8.4 Hz, 1H), 3.25 (dd, J=15.4, 2.0 Hz, 1H), 3.14 (d, J=12.1 Hz, 1H), 3.03 (dd, J=17.9, 8.1 Hz, 1H), 2.69 (d, J=17.9 Hz, 1H), 2.29 (s, 3H), 2.24 (s, 3H), 2.08 (s, 3H), 1.72 (dd, J=15.3, 11.9 Hz, 1H), 1.24 (d, J=4.4 Hz, 3H), 1.22 (d, J=4.4 Hz, 3H); FTIR (neat) 3435 (m br), 2973 (m br), 2933 (m br), 1773 (m), 1716 (s), 1619 (w), 1588 (w), 1500 (w), 1461 (m), 1432 (m), 1395 (m), 1384 (m), 1233 (m), 1144 (m), 1100 (m), 1075 (m), 1064 (m), 1029 (m), 1006 (w), 998 (w), 947 (w) $cm^{-1}$; HRMS (FAB), [m+Na]/z calc'd for $C_{37}H_{38}O_7N_4Na$: 673.2638, found 673.2663.

EXAMPLE 46

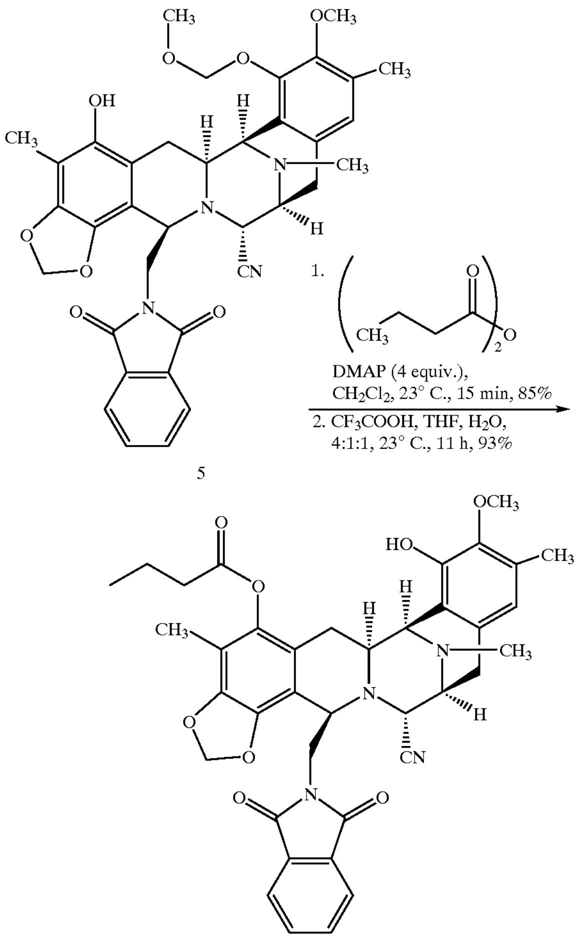

5

43

Phenol (5) (1.0 mg, 0.0015 mmol) was dissolved in methylene chloride (0.5 mL) to this solution were added 4-dimethylaminopyridine (0.8 mg, 0.0066 mmol) and n-butyric anhydride (1.0 μL, 0.0061 mmol). The reaction was stirred at 23° C. for 15 min and then quenched into a saturated solution of aqueous sodium bicarbonate (2 mL). The mixture was extracted with methylene chloride (2x5 mL) and the organic layers were dried over sodium sulfate, decanted and concentrated in vacuo. The residue was purified by flash column chromatography (1 mL silica gel, gradient methylene chloride to 1:1 to 2:1 ethyl acetate-hexane) to afford a residue (0.9 mg, 83%). This material was dissolved in a mixture of trifluoroacetic acid-THF-water (4:1:1 (v/v), 1.0 mL) and the solution was stirred at 23° C. for 11 hr. The reaction mixture was diluted with toluene (1 mL) and the solution was concentrated in vacuo. Additional volatiles were removed by repetitive in vacuo azeotropic concentration from toluene (3x1 mL). The residue was purified by flash column chromatography (1 mL silica gel, gradient methylene chloride to 2:1 ethyl acetate-hexane) to afford Compound 43 (0.7 mg, 93%). $R_f$0.56 (2:1 ethyl acetate-hexane); $^1H$ NMR (400 MHz, $CDCl_3$) δ7.74–7.71 (m, 2H), 7.68–7.65 (m, 2H), 6.38 (s, 1H), 5.64 (s, 1H), 5.55 (s, 1H), 5.25 (s, 1H), 4.27–4.21 (m, 2H), 4.02 (d, J=2.3 Hz, 1H), 3.66 (s, 3H), 3.62–3.60 (m, 2H), 3.34 (d, J=7.7 Hz, 1H), 3.20 (d, J=11.9 Hz, 1H), 3.02 (dd, J=18.0, 8.0 Hz, 1H), 2.78 (d, J=15.3 Hz, 1H), 2.63 (d, J=18.0 Hz, 1H), 2.55 (dt, J=2.5, 7.3 Hz, 2H), 2.28 (s, 3H), 2.23 (s, 3H), 1.97 (s, 3H), 1.82 (q, J=7.4 Hz, 2H), 1.78–1.72 (m, 1H), 1.08 (t, J=7.4 Hz, 3H); FTIR (neat) 3433 (m br), 2934 (m br), 2876 (w), 1758 (m), 1716 (s), 1499 (w), 1459 (m), 1432 (m), 1395 (m), 1328 (w), 1296 (w), 1234 (m), 1190 (w), 1172 (m), 1146 (m), 1102 (m), 1072 (m), 1029 (w), 1005 (w), 998 (w), 947 (w) $cm^{-1}$; HRMS (FAB), [m+Na]/z calc'd for $C_{38}H_{38}O_8N_4Na$: 701.2587, found 701.2581.

EXAMPLE 47

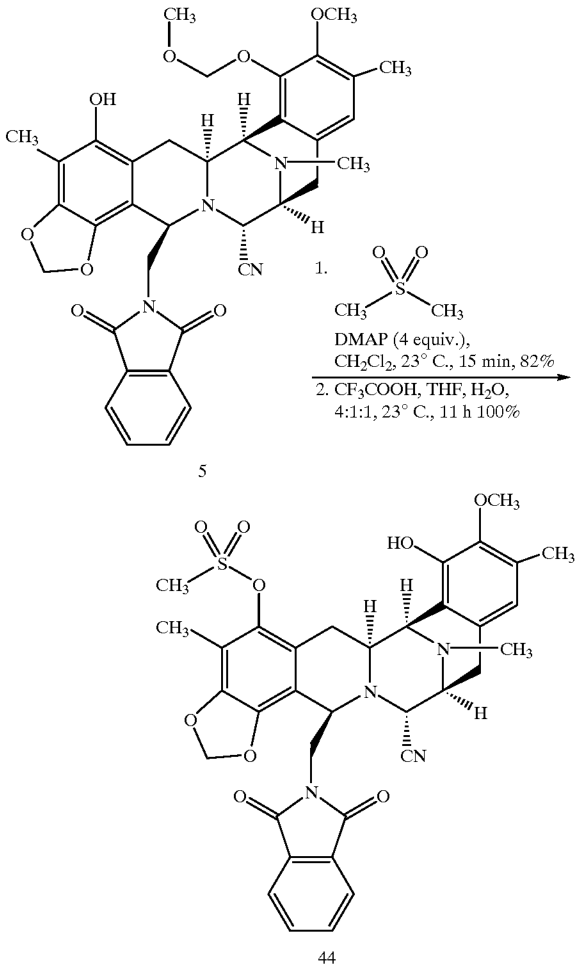

5

44

Phenol (5) (1.0 mg, 0.0015 mmol) was dissolved in methylene chloride (0.5 mL) to this solution were added 4-dimethylaminopyridine (0.8 mg, 0.0066 mmol) and methanesulfonyl chloride (0.5 μL, 0.0065 mmol). The reaction was stirred at 23° C. for 15 min and then quenched into a saturated solution of aqueous sodium bicarbonate (2 mL). The mixture was extracted with methylene chloride (2×5 mL) and the organic layers were dried over sodium sulfate, decanted and concentrated in vacuo. The residue was purified by flash column chromatography (1 mL silica gel, gradient methylene chloride to 1:1 to 2:1 ethyl acetate-hexane) to afford a residue (0.9 mg, 82%). This material was dissolved in a mixture of trifluoroacetic acid-THF-water (4:1:1 (v/v), 1.0 mL) and the solution was stirred at 23° C. for 11 h. The reaction mixture was diluted with toluene (1 mL) and the solution was concentrated in vacuo. Additional volatiles were removed by repetitive in vacuo azeotropic concentration from toluene (3×1 mL). The residue was purified by flash column chromatography (1 mL silica gel, gradient methylene chloride to 2:1 ethyl acetate-hexane) to afford Compound 44 (0.8 mg, 100%). $R_f$0.45 (2:1 ethyl acetate-hexane); $^1H$ NMR (400 MHz, $CDCl_3$) δ7.68–7.62 (m, 4H), 6.43 (s, 1H), 5.76 (d, J=1.5 Hz, 1H), 5.60 (s, 1H), 5.47 (d, J=1.5 Hz, 1H), 4.25–4.22 (m, 2H), 4.06 (d, J=2.2 Hz, 1H), 3.73 (dd, J=14.0, 6.9 Hz, 1H), 3.67 (dd, J=14.0, 3.3 Hz, 1H), 3.55 (s, 3H), 3.37 (d, J=8.0 Hz, 1H), 3.20–3.13 (m, 5H), 3.03 (dd, J=18.1, 8.1 Hz, 1H), 2.73 (d, J=18.0 Hz, 1H), 2.30 (s, 3H), 2.22 (s, 3H), 2.21 (s, 3H), 1.85 (dd, J=16.0, 12.0 Hz, 1H); FTIR (neat) 3464 (m br), 2936 (m br), 2855 (w), 1774 (w), 1716 (s), 1499 (w), 1461 (m), 1433 (m), 1394 (m), 1366 (m), 1295 (w), 1234 (w), 1178 (m), 1145 (w), 1101 (m), 1081 (w), 1070 (m), 1058 (m), 1030 (w), 996 (w), 971 (w), 948 (w), 890 (m), 808 (w) $cm^{-1}$; HRMS (FAB), [m+Na]/z calc'd for $C_{35}H_{34}O_9N_4SNa$: 709.1944, found 709.1956.

EXAMPLE 48

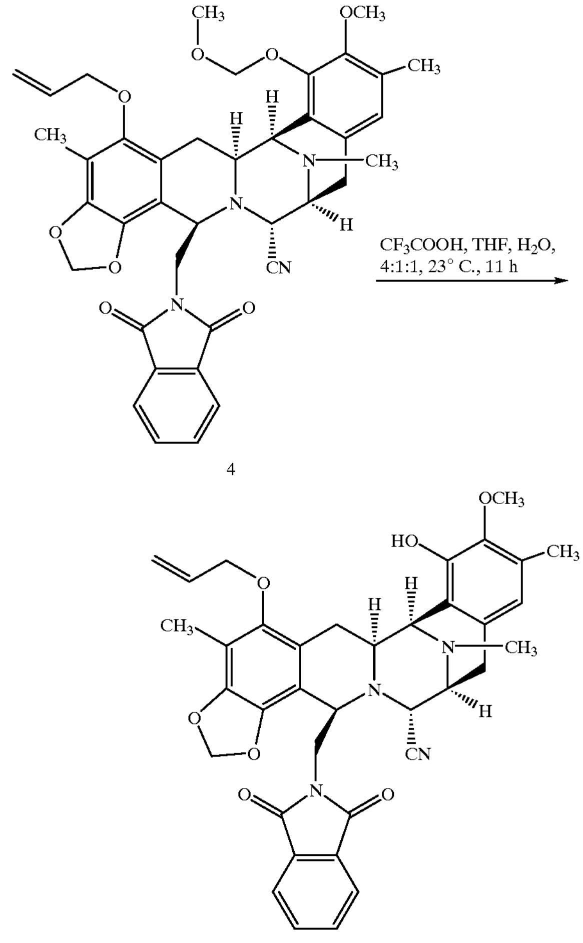

4

45 (85%)

Methoxymethyl ether (4) (0.5 mg, 0.00072 mmol) was dissolved in a mixture of trifluoroacetic acid-THF-water (4:1:1 (v/v), 1.0 mL) and the solution was stirred at 23° C. for 11 h. The reaction mixture was diluted with toluene (1 mL) and the solution was concentrated in vacuo. Additional volatiles were removed by repetitive in vacuo azeotropic concentration from toluene (3×1 mL). The residue was purified by flash column chromatography (0.5 mL silica gel, gradient methylene chloride to 2:1 ethyl acetate-hexane) to afford Compound 45 (0.4 mg, 85%). $R_f$0.53 (2:1 ethyl acetate-hexane); $^1H$ NMR (400 MHz, $CDCl_3$) δ7.73–7.65 (m, 4H), 6.41 (s, 1H), 6.18–6.02 (m, 1H), 5.61 (s, 1H), 5.58

(d, J=1.5 Hz, 1H), 5.38 (dd, J=17.2, 1.5 Hz, 1H), 5.24 (d, J=10.3 Hz, 1H), 5.13 (d, J=1.4 Hz, 1H), 4.23–4.13 (m, 3H), 4.08 (s, 1H), 3.97 (dd, J=7.5, 5.9 Hz, 1H), 3.68 (s, 3H), 3.59–3.52 (m, 2H), 3.35 (d, J=8.2 Hz, 1H), 3.24 (dd, J=17.3, 2.1 Hz, 1H), 3.18 (d, J=11.4 Hz, 1H), 3.04 (dd, J=17.3, 8.0 Hz, 1H), 2.64 (d, J=18.2 Hz, 1H), 2.30 (s, 3H), 2.24 (s, 3H), 2.09 (s, 3H), 1.80 (dd, J=15.2, 11.7 Hz, 1H); FTIR (neat) 3413 (w br), 2931 (m br), 2856 (w), 1775 (w), 1713 (s), 1463 (m), 1431 (m), 1394 (m), 1300 (w), 1269 (w), 1231 (w), 1144 (w), 1100 (m), 1063 (w), 1031 (w), 994 (w), 950 (w) $cm^{-1}$; HRMS (FAB), [m+Na]/z calc'd for $C_{37}H_{36}O_7N_4Na$: 671.2482, found 671.2498.

EXAMPLE 49

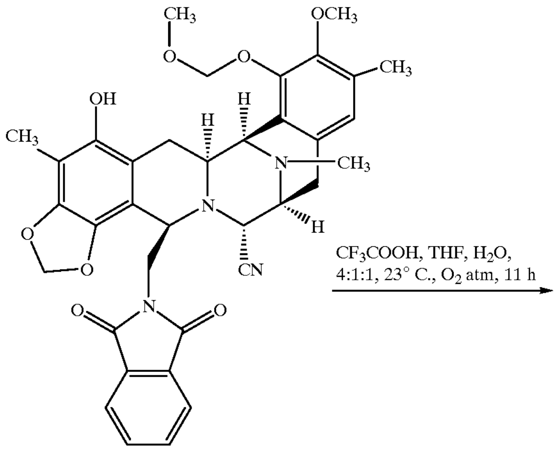

5

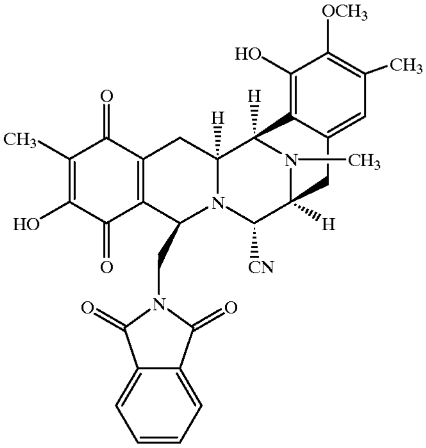

46 (50%)

The methoxymethyl ether (5) (5.0 mg, 0.0077 mmol) was dissolved in a mixture of trifluoroacetic acid-THF-water (4:1:1 (v/v), 1.2 mL) and the solution. was stirred at 23° C. for 11 h under an atmosphere of oxygen. The reaction mixture was diluted with toluene (5 mL) and the solution was concentrated in vacuo. Additional volatiles were removed by repetitive in vacuo azeotropic concentration from toluene (3x5 mL). The residue was purified by preparative TLC (2:1 ethyl acetate-hexane) to afford Compound 46 (2.3 mg, 50%). $R_f$ 0.38 (5% methanol-methylene chloride, $^1H$ NMR (400 MHz, $C_6D_6$) δ7.07–7.05 (m, 2H), 6.66–6.64 (m, 2H), 6.31 (s, 1H), 5.10 (s, 1H), 4.07 (br s, 1H), 4.06 (d, J=2.0 Hz, 1H), 3.81 (d, J=2.3 Hz, 1H), 3.74 (dd, J=14.5, 1.8 Hz, 1H), 3.67 (dd, J=14.6, 4.5 Hz, 1H), 3.53 (br s, 1H), 3.19–3.14 (m, 2H), 2.86 (d, J=7.9 Hz, 1H), 2.79 (d, J=18.3 Hz, 1H), 2.72 (s, 3H), 2.60 (dd, J=18.1, 7.7 Hz, 1H), 2.29–2.17 (m, 1H), 2.10 (s, 3H), 1.94 (s, 3H), 1.88 (s, 3H); FTIR (neat) 3399 (m br), 2928 (m br), 2855 (m), 1773 (w), 1713 (s), 1657 (m), 1644 (m), 1631 (m), 1436 (m), 1416 (m), 1396 (m), 1382 (m), 1378 (m), 1360 (m), 1334 (m), 1303 (m), 1245 (m), 1234 (w), 1172 (w) $cm^{-1}$; HRMS (FAB), [m+Na]/z calc'd for $C_{33}H_{30}O_7N_4Na$: 617.2012, found 617.2036.

EXAMPLE 50

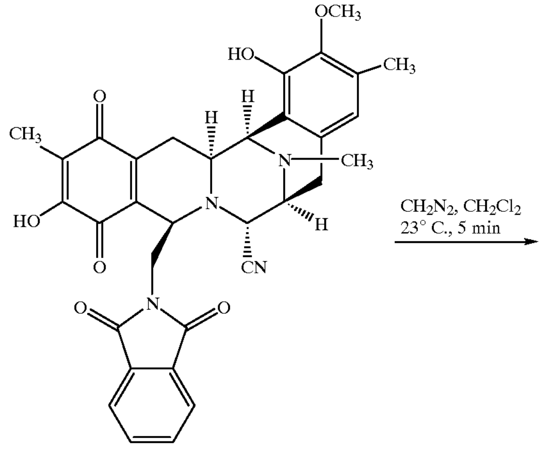

46

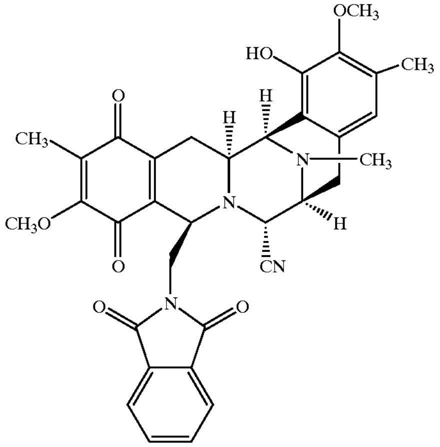

47 (42%)

The hydroxyquinone (46) (2.3 mg, 0.0038 mmol) was dissolved in methylene chloride (3 mL). A dilute diazomethane solution in diethyl ether was added in small portions while monitoring the reaction by TLC analysis. Upon complete conversion to the product, acetic acid (50 μL) was added to quench the reaction. Purification via preparative TLC (1:1 ethyl acetate-hexane) afforded pure (47) (1.0 mg, 42%). $R_f$ 0.33 (1:1 ethyl acetate-hexane); $^1H$ NMR (500 MHz, $CDCl_3$) δ7.59 (m, 4H), 6.43 (s, 1H), 5.48 (s, 1H), 4.39 (d, J=2.3 Hz, 1H), 4.11 (br s, 1H), 4.07 (s, 3H), 4.07–4.03 (m, 1H), 4.01 (d, J=2.0 Hz, 1H), 3.81 (dd, J=14.5, 1.3 Hz, 1H), 3.43–3.39 (m, 1H), 3.40 (s, 3H), 3.03 (dt, J=11.1, 2.7 Hz, 1H), 2.98–2.93 (m, 3H), 2.30 (s, 3H), 2.12 (s, 3H), 1.96 (s, 3H); FTIR (neat) 3459 (m br), 2934 (m br), 2855 (m), 1773 (m), 1713 (s), 1659 (s), 1641 (m), 1622 (m), 1499 (m), 1437 (s), 1396 (m), 1362 (m), 1302 (m), 1282 (m), 1267 (m), 1239 (s), 1163 (m), 1149 (m), 1138 (m), 1104 (m), 1087 (m), 1061 (m), 997 (m), 969 (m), 921 (m) $cm^{-1}$; HRMS (FAB), [m+Na]/z calc'd for $C_{34}H_{32}O_7N_4Na$: 631.2169, found 631.2183.

EXAMPLE 51

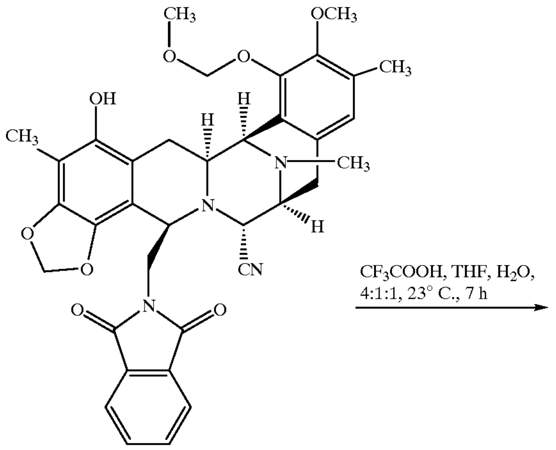

5

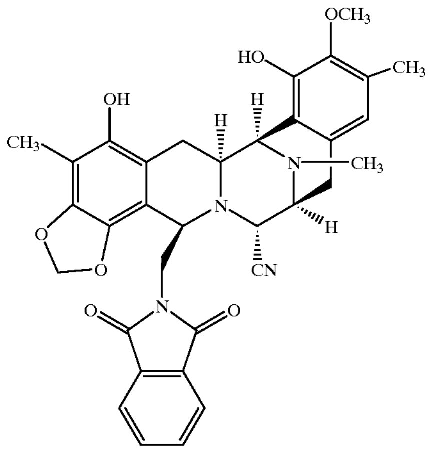

48 (71%)

The methoxymethyl ether (5) (0.6 mg, 0.00092 mmol) was dissolved in a mixture of trifluoroacetic acid-THF-water (4:1:1 (v/v), 1.0 mL) and the solution was stirred at 23° C. for 7 h. The reaction mixture was diluted with toluene (1 mL) and the solution was concentrated in vacuo. Additional volatiles were removed by repetitive in vacuo azeotropic concentration from toluene (3×1 mL). The residue was purified by flash column chromatography (0.4 mL silica gel, gradient methylene chloride to 2:1 ethyl acetate-hexane) to afford Compound 48 (0.4 mg, 71%). $R_f$0.37 (2:1 ethyl acetate-hexane); $^{1}$H NMR (500 MHz, $CDCl_3$) δ7.45–7.73 (m, 2H), 7.69–7.66 (m, 2H), 6.39 (s, 1H), 5.71 (s, 1H), 5.51 (s, 1H), 5.02 (s, 1H), 4.28–4.17 (m, 3H), 4.15–4.07 (m, 1H), 3.74 (s, 3H), 3.59–3.49 (m, 2H), 3.35 (d, J=8.0 Hz, 1H), 3.23 (d, J=11.9 Hz, 1H), 3.11–3.02 (m, 2H), 2.62 (d, J=18.0 Hz, 1H), 2.31 (s, 3H), 2.24 (s, 3H), 2.07 (s, 3H), 1.86 (dd, J=14.9, 11.8 Hz, 1H); FTIR (neat) 3464 (m br), 2934 (m br), 1772 (m), 1713 (s), 1460 (m br), 1433 (m br), 1416 (m br), 1367 (w), 1324 (w), 1234 (m), 1102 (m), 1075 (w), 1061 (w), 1028 (w), 1006 (w) cm$^{-1}$; HRMS (FAB), [m+H]/z calc'd for $C_{34}H_{33}O_7N_4$: 609.2349, found 609.2341.

EXAMPLE 52

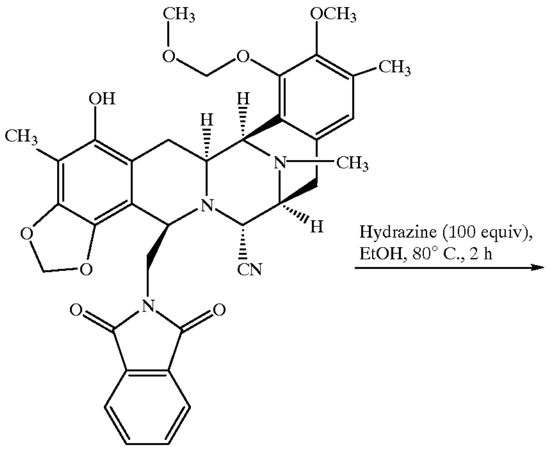

5

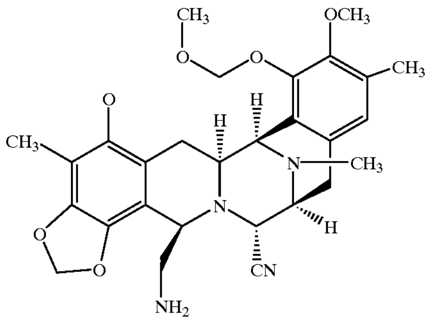

49 (100%)

Phthalimide (5) (5.4 mg, 0.0083 mmol) was dissolved in ethanol (0.3 mL) and hydrazine (26 μL, 0.829 mmol) was added. The vessel was sealed and heated to 80° C. for 2 h. The reaction was concentrated in vacuo. Additional volatiles were removed by repetitive in vacuo azeotropic concentration from toluene (2×1 mL). The residue was purified by flash column chromatography (0.5 mL silica gel, gradient methylene chloride to 5% methanol-ethyl acetate) to afford Compound 49 (4.3 mg, 100%). $R_f$0.18 (5% methanol-ethyl acetate); $^{1}$H NMR (400 MHz, $CDCl_3$) δ6.66 (s, 1H), 5.88 (s, 1H), 5.80 (s, 1H), 5.34 (d, J=6.1 Hz, 1H), 5.19 (d, J=6.0 Hz, 1H), 4.23 (d, J=2.3 Hz, 1H), 4.01 (d, J=2.6 Hz, 1H), 3.94 (s, 1H), 3.70 (s, 3H), 3.69 (s, 3H), 3.37 (d, J=7.7 Hz, 1H), 3.33 (d, J=9.0 Hz, 1H), 3.10–3.04 (m, 2H), 2.83 (d, J=13.8 Hz, 1H), 2.74 (dd, J=13.7, 2.5 Hz, 1H), 2.49 (d, J=18.0 Hz, 1H), 2.34 (s, 3H), 2.20 (s, 3H), 2.08 (s, 3H), 1.79 (dd, J=15.0, 11.9 Hz, 1H); $^{13}$C NMR (100 MHz, $CDCl_3$) δ149.1, 147.6, 145.5, 144.6, 135.9, 131.0, 130.2, 124.8, 122.9, 117.8, 113.1, 112.6, 106.1, 100.7, 99.8, 59.8, 59.5, 58.8, 57.7, 56.7, 55.6, 55.3, 43.6, 41.7, 26.2, 25.7, 15.7, 8.8; FTIR (neat) 3346 (w br), 3000 (w v br), 2935 (s br), 1446 (s br), 1419 (m), 1401 (m), 1327 (m), 1152 (m), 1101 (s), 1075 (m), 1060 (m), 998 (m), 975 (m) cm$^{-1}$; HRMS (FAB), [m+H]/z calc'd for $C_{28}H_{35}O_6N_4$: 523.2557, found 523.2552; $[\alpha]_D^{23}$=−16.5° (c 0.20, methylene chloride).

EXAMPLE 53

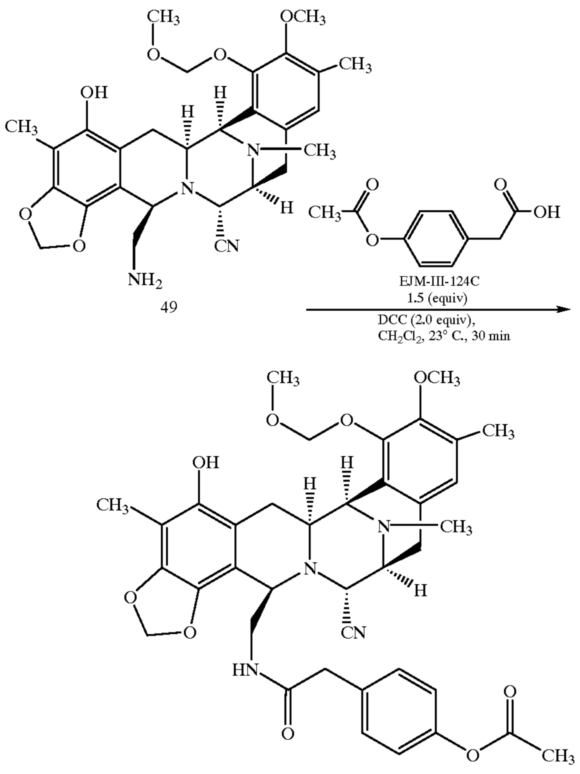

49

50 (50%)

EXAMPLE 54

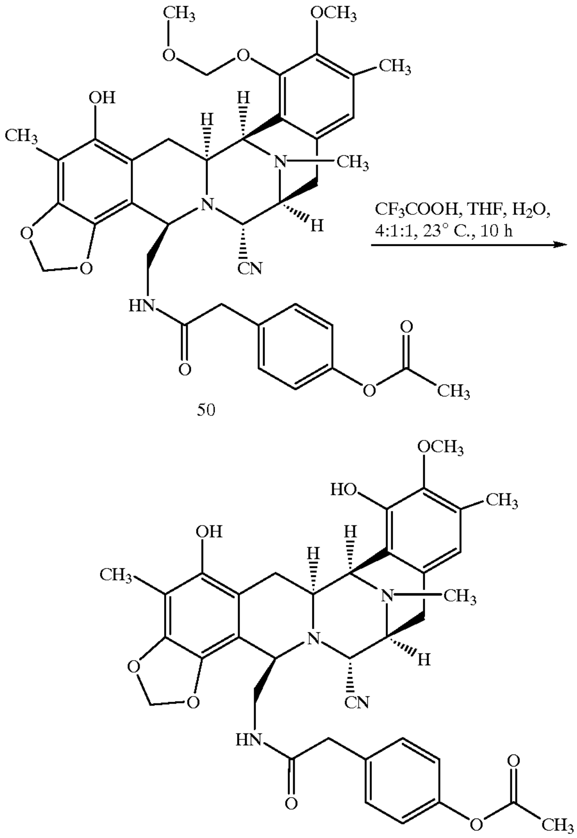

50

51 (42%)

Amine (49) (0.9 mg, 0.0017 mmol) and acid EJM-III-124C (0.5 mg, 0.0026 mmol) were azeotropically tried with toluene (2×1 mL) and then dissolved in methylene chloride (0. 1 mL). 1,3-Dicyclohexylcarbodiimide (0.7 mg, 0.0034 mmol) was added to the solution which was stirred at 23° C. for 30 min. White precipitate was observed and the reaction was quenched into saturated aqueous sodium bicarbonate solution (7 mL). The aqueous layer was extracted with methylene chloride (2×7 mL) and the organic layers were dried over sodium sulfate, decanted and concentrated in vacuo. The residue was purified by flash column chromatography (1.0 mL silica gel, gradient 2:1 ethyl acetate-hexane to ethyl acetate) to afford Compound 50 (0.5 mg, 50%). $R_f$0.16 (2:1 ethyl acetate-hexane); $^1$H NMR (500 MHz, $CDCl_3$) δ6.91 (s, 1H), 6.83 (d, J=8.2 Hz, 2H), 6.77 (s, 1H), 6.67 (d, J=8.4 Hz, 2H), 5.83 (s, 1H), 5.74 (s, 1H), 5.58 (s, 1H), 5.33 (d, J=6.3 Hz, 1H), 5.17 (d, J=6.0 Hz, 1H), 4.90 (m, 1H), 4.23 (s, 1H), 4.14 (s, 1H), 3.98 (s, 1H), 3.70 (s, 3H), 3.69 (s, 3H), 3.57–3.46 (m, 2H), 3.38 (d, J=7.5 Hz, 1H), 3.25 (d, J=11.5 Hz, 1H), 3.15 (d, J=15.8 Hz, 1H), 3.02–2.98 (m, 1H), 2.85 (d, J=15.8 Hz, 1H), 2.69 (d, J=18.0 Hz, 1H), 2.32 (s, 3H), 2.28 (s, 3H), 2.24 (s, 3H), 2.06 (s, 3H), 1.65 (m, 1H); FTIR (neat) 3400 (w br), 2924 (s br), 2853 (s), 1763 (m), 1753 (m), 1745 (m), 1737 (m), 1461 (m), 1452 (w), 1440 (w), 1350 (w), 1234 (w), 1216 (m), 1197 (m), 1160 (w) cm$^{-1}$; HRMS (FAB), [m+H]/z calc'd for $C_{38}H_{43}O_9N_4$: 699.3030, found 699.3005.

The methoxymethyl ether (50) (1.3 mg, 0.0019 mmol) was dissolved in a mixture of trifluoroacetic acid-THF-water (4:1:1 (v/v), 1.0 mL) and the solution was stirred at 23□C for 10 h. The reaction mixture was diluted with toluene (1 mL) and the solution was concentrated in vacuo. Additional volatiles were removed by repetitive in vacuo azeotropic concentration from toluene (3×1 mL). The residue was purified by flash column chromatography (0.3 mL silica gel, gradient 2:1 ethyl acetate-hexane to ethyl acetate) to afford Compound 51 (0.5 mg, 42%). $R_f$0.19 (2:1 ethyl acetate-hexane); $^1$H NMR (500 MHz, $CDCl_3$) δ6.74 (d, J=8.4 Hz, 2H), 6.56 (s, 1H), 6.48 (d, J=8.4 Hz, 2H), 5.89 (s, 1H), 5.79 (s, 1H), 5.75 (s, 1H), 4.92 (s, 1H), 4.81 (s, 1H), 4.12 (s, 1H), 4.01 (d, J=13.3 Hz, 2H), 3.81 (m, 4H), 3.36 (d, J=7.1 Hz, 1H), 3.27 (d, J=13.0 Hz, 1H), 3.21 (d, J=15.5 Hz, 1H), 3.16 (d, J=12.0 Hz, 1H), 3.02 (dd, J=17.9, 8.3 Hz, 1H), 2.89 (d, J=15.6 Hz, 1H), 2.72 (d, J=15.4 Hz, 1H), 2.49 (d, J=18.4 Hz, 1H), 2.39 (s, 3H), 2.34 (s, 3H), 2.30 (s, 3H), 2.06 (s, 3H), 1.11 (dd, J=15.3, 11.3 Hz, 1H); FTIR (neat) 3388 (s br), 2931 (s br), 1754 (m), 1657 (m), 1506 (m), 1460 (m br), 1434 (m br), 1369 (m), 1233 (s), 1194 (s), 1099 (m) cm$^{-1}$; HRMS (FAB), [m+Na]/z calc'd for $C_{36}H_{38}O_8N_4Na$: 677.2587, found 677.2573.

EXAMPLE 55

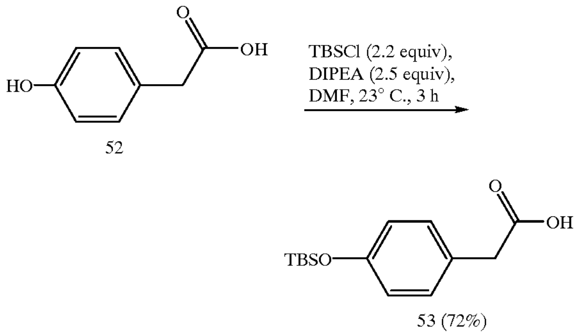

52

53 (72%)

p-Hydroxyphenylacetic acid (52) (100 mg, 0.657 mmol) was dissolved in DMF (3.0 mL). tert-Butyldimethylsily chloride (222 mg, 1.47 mmol) and N,N-diisopropylethylamine (0.285 mL, 1.64 mmol were added to the solution which was stirred at 23° C. for 3 h. Water (1 mL) was added and after 15 min the reaction mixture was poured into 5% aqueous acetic acid (25 mL) and extracted with ethyl acetate (2x25 mL). The organic layers were then washed with water (2x20 mL) and saturated aqueous sodium chloride (20 mL), dried over sodium sulfate, decanted and concentrated in vacuo. The residue was purified by flash column chromatography (120 mL silica gel, gradient 1:4 to 1:1 ethyl acetate-hexane, 0.1% acetic acid) to afford Compound 53 (125 mg, 72%). $R_f$0.52 (2:1 ethyl acetate-hexane); $^1$H NMR (400 MHz, $CDCl_3$) δ7.14 (d, J=8.5 Hz, 2H), 6.80 (d, J=8.5 Hz, 2H), 3.57 (s, 2H), 0.98 (s, 9H), 0.19 (s, 6H); $^{13}$C NMR (100 MHz, $CDCl_3$) δ178.3, 154.9, 130.3, 125.8, 120.1, 40.3, 25.6, 18.2, −4.4; FTIR (neat) 3122 (w br), 2957 (m), 2931 (m), 2897 (m), 2888 (m), 2859 (m), 1712 (s), 1611 (w), 1512 (s), 1472 (w), 1464 (w), 1409 (w), 1263 (s), 1171 (w), 917 (s), 840 (m), 826 (m), 803,(m) $cm^{-1}$; HRMS (EI), [m+] calc'd for $C_{14}H_{22}O_3Si$: 266.1338, found 266.1331.

EXAMPLE 56

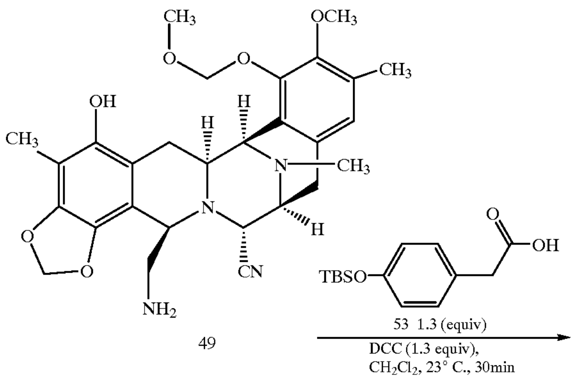

49

-continued

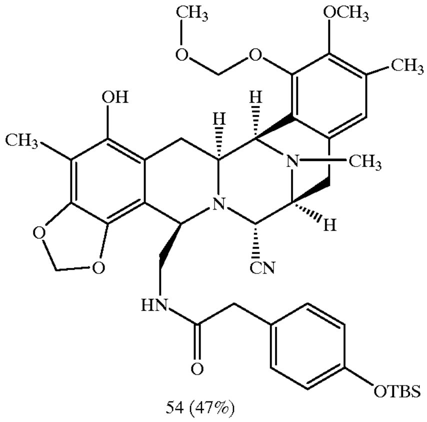

54 (47%)

Amine (49) (2.0 mg, 0.0038 mmol) and acid (53) (1.3 mg, 0.0049 mmol) were azeotropically dried with toluene (2x1 mL) and then dissolved in methylene chloride (0.2 mL). 1,3-Dicyclohexylcarbodiimide (1.0 mg, 0.0049 mmol) was added to the solution which was stirred at 23° C. for 30 min. White precipitate was observed and the reaction was quenched into saturated solution of aqueous sodium bicarbonate (5 mL). The aqueous layer was extracted with methylene chloride (2x5 mL) and the organic layers were dried over sodium sulfate, decanted and concentrated in vacuo. The residue was purified by flash column chromatography (1.7 mL silica gel, gradient 1:4 ethyl acetate-hexane to ethyl acetate) to afford Compound 54 (1.4 mg, 47%). $R_f$0.39 (2:1 ethyl acetate-hexane); $^1$H NMR (400 MHz, $CDCl_3$) δ6.76 (s, 1H), 6.55 (d, J=8.4 Hz, 2H), 6.47 (d, J=8.3 Hz, 2H), 5.82, (s, 1H), 5.74 (s, 1H), 5.53 (s, 1H), 5.35 (d, J=6.1 Hz, 1H), 5.18 (d, J=6.1 Hz, 1H), 4.89 (br s, 1H), 4.20 (s, 1H), 4.15 (d, J=2.3 Hz, 1H), 3.97 (s, 1H), 3.70 (s, 6H), 3.67–3.58 (m, 1H), 3.44–3.36 (m, 2H), 3.23 (d, J=11.4 Hz, 1H), 3.11 (d, J=16.1 Hz, 1H), 3.02–2.96 (m, 2H), 2.83 (d, J=16.1 Hz, 1H), 2.70 (d, J=18.2 Hz, 1H), 2.31 (s, 3H), 2.23 (s, 3H), 2.07 (s, 3H), 1.67–1.57 (m, 1H), 0.96 (s, 9H), 0.14 (s, 3H), 0.13 (s, 3H); FTIR (neat) 3396 (w br), 2930 (m br), 2857 (m), 1656 (m br), 1651 (w), 1509 (s), 1462 (m br), 1257 (s), 1157 (m), 1097 (s), 1060 (m), 915 (m) $cm^{-1}$; HRMS (FAB), [m+Na]/z calc'd for $C_{42}H_{54}O_8N_4SiNa$: 793.3609, found 793.3624.

EXAMPLE 57

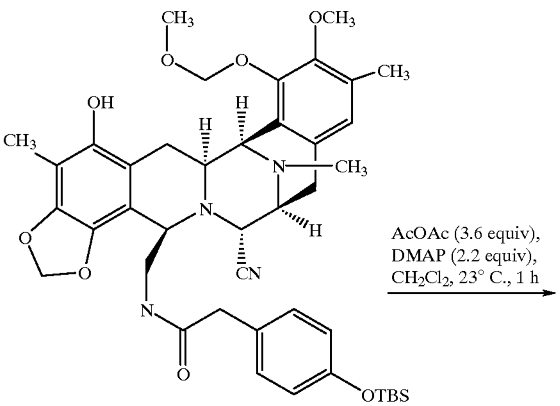

54

-continued

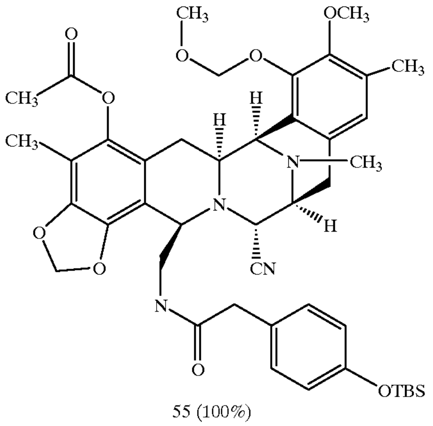

55 (100%)

-continued

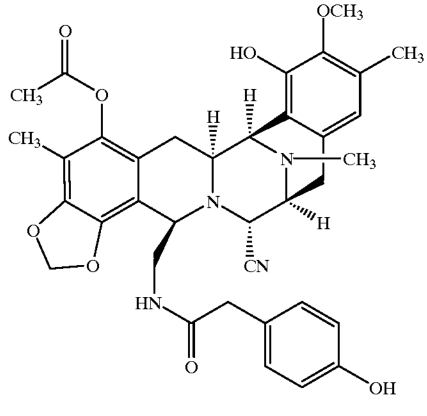

56 (44%)

Phenol (54) (1.1 mg, 0.0015 mmol) was dissolved in methylene chloride (0.2 mL). 4-Dimethylaminopyridine (0.4 mg, 0.0032 mmol) and acetic anhydride (0.5 μL, 0.0053 mmol) were added to the solution which was stirred at 23° C. for 1 h. The reaction mixture was concentrated in vacuo. The residue was purified by flash column chromatography (0.3 mL silica gel, gradient 1:1 ethyl acetate-hexane to ethyl acetate) to afford Compound 55 (1.2 mg, 100%). $R_f$0.48 (2:1 ethyl acetate-hexane); $^1$H NMR (500 MHz, $CDCl_3$) δ6.78 (s, 1H), 6.75–6.65 (m, 4H), 5.89 (d, J=1.3 Hz, 1H), 5.84 (d, J=1.3 Hz, 1H), 5.16 (d, J=5.7 Hz, 1H), 5.06 (d, J=5.7 Hz, 1H), 5.03 (br s, 1H), 4.18 (s, 2H), 3.96 (s, 1H), 3.71 (s, 3H), 3.62 (m, 1H), 3.58 (s, 3H), 3.39–3.32 (m, 2H), 3.25 (d, J=13.0 Hz, 1H), 3.01 (dd, J=18.2, 8.2 Hz, 1H), 2.95 (d, J=15.4 Hz, 1H), 2.83 (d, J=15.7 Hz, 1H), 2.78 (m, 1H), 2.74 (d, J=18.2 Hz, 1H), 2.35 (s, 3H), 2.34 (s, 3H), 2.17 (s, 3H), 1.99 (s, 3H), 1.78 (dd, J=15.3, 11.6 Hz, 1H), 0.94 (s, 9H), 0.12 (s, 3H), 0.11 (s, 3H); FTIR (neat) 3404 (w br), 2932 (s br), 2858 (m), 1761 (m), 1673 (m), 1509 (s), 1442 (m br), 1368 (m), 1259 (s), 1201 (s), 1159 (m), 1089 (m), 916 (m) $cm^{-1}$; HRMS (FAB), [m+Na]/z calc'd for $C_{44}H_{56}O_9N_4SiNa$: 835.3714, found 835.3699.

The methoxymethyl ether (55) (1.2 mg, 0.0015 mmol) was dissolved in a mixture of trifluoroacetic acid-THF-water (4:1:1 (v/v), 1.0 mL) and the solution was stirred at 23° C. for 10 h. The reaction mixture was diluted with toluene (1 mL) and the solution was concentrated in vacuo. Additional volatiles were removed by repetitive in vacuo azeotropic concentration from toluene (3×1 mL). The residue was purified by flash column chromatography (0.3 mL silica gel, ethyl acetate) to afford Compound 56 (0.4 mg, 44%). $R_f$0.13 (2:1 ethyl acetate-hexane); $^1$H NMR (400 MHz, $CDCl_3$) δ6.56–6.48 (m, 5H), 5.92 (d, J=1.3 Hz, 1H), 5.85 (d, J=1.3 Hz, 1H), 5.74 (s, 1H), 5.36 (s, 1H), 4.88 (br s, 1H), 4.14–4.08 (m, 2H), 3.98 (s, 1H), 3.78 (s, 3H), 3.68–3.43 (m, 2H), 3.36 (d, J=7.4 Hz, 1H), 3.22 (d, J=11.9 Hz, 1H), 3.07–2.93 (m, 3H), 2.82–2.73 (m, 1H), 2.66 (d, J=16.3 Hz, 1H), 2.38 (s, 3H), 2.29 (s, 3H), 2.34 (s, 3H), 1.98 (s, 3H), 1.74–1.65 (m, 1H); FTIR (neat) 3403 (s br), 2929 (s br), 2856 (m), 1756 (m), 1656 (m), 1513 (s), 1450 (m), 1369 (m), 1233 (s), 1201 (s), 1086 (m) $cm^{-1}$; HRMS (FAB), [m+Na]/z calc'd for $C_{36}H_{38}O_8N_4Na$: 677.2587, found 677.2587.

EXAMPLE 58

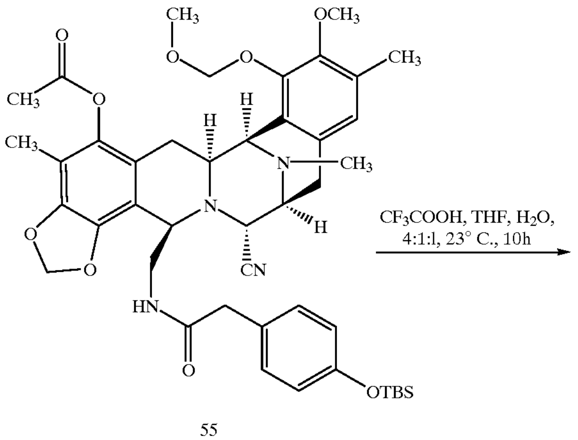

55

EXAMPLE 59

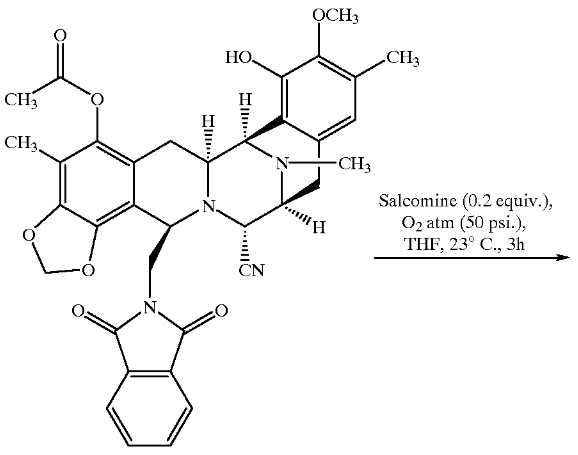

7

-continued

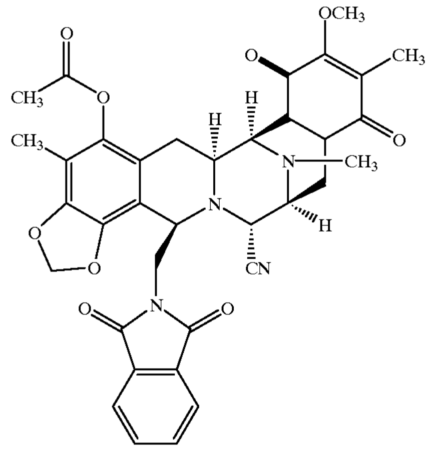

57 (90%)

Compound 7 1.0 mg, 0.00154 mmol) was dissolved in THF (1.0 mL). Salcomine (0.1 mg, 0.00031 mmol) was added as a solid to make an orange solution. The vial was secured inside a bomb reactor and the vessel was purged with oxygen ten times and filled to 50 psi. (~3 bar). The solution was stirred at 23° C. for 3 h. The reaction concentrated in vacuo, passed through a small pad of silica get eluting with ethyl acetate and purified by preparative thin layer chromatography (1:1 ethyl acetate-hexane, 2×) to afford Compound 57 (0.9 mg, 90%). $R_f$0.51 (2:1 ethyl acetate-hexane); $^1$H NMR (400 MHz, $CDCl_3$) δ7.70 (m, 4H), 5.85 (s, 1H), 5.72 (br s, 1H), 4.32 (t, J=5.1 Hz, 1H), 4.02 (d, J=2.2 Hz, 1H), 3.90 (s, 1H), 3.80 (s, 3H), 3.73 (d, J=5.1 Hz, 2H), 3.34 (d, J=7.3 Hz, 1H), 3.15 (d, J=12.1 Hz, 1H), 2.73 (dd, J=20.8, 7.3 Hz, 1H), 2.46 (dd, J=15.2, 2.0 Hz, 1H), 2.32 (s, 1H), 2.27 (s, 3H), 2.26 (s, 3H), 2.03 (s, 3H), 2.01 (s, 3H), 1.50–1.43 (m, 1H); FTIR (neat) 2938 (w), 2898 (w), 2851 (w), 1764 (m), 1716 (s), 1649 (m), 1616 (m), 1432 (m), 1393 (m), 1371 (m), 1308 (m), 1232 (m), 1197 (m), 1146 (m), 1101 (m), 1084 (w), 1029 (w), 946 (w), 906 (w) $cm^{-1}$; HRMS (FAB), [m+Na]/z calc'd for $C_{36}H_{32}O_9N_4Na$: 687.2067, found 687.2061.

TABLE 4

General Procedure for the Coupling of Alcohol (9) with Dicarboximides.

| Entry | Dicarboximide | Mitsunobu Coupling Yield | MOM Removal Yield |
|---|---|---|---|
| Ex. 60 | 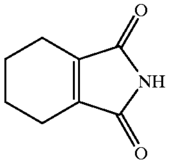 | 57% No. 58 | 73% No. 59 |

TABLE 4-continued

General Procedure for the Coupling of Alcohol (9) with Dicarboximides.

| Entry | Dicarboximide | Mitsunobu Coupling Yield | MOM Removal Yield |
|---|---|---|---|
| Ex. 61 | 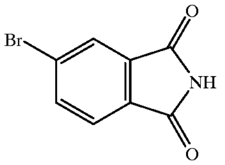 | 60% No. 60 | 100% No. 61 |

EXAMPLE 60

Compound 59. The amount of Compound 9 was increased to 2.3 mg for this reaction. Preparative thin layer chromatography of the first step was done using 2:1 diethyl ether-hexane. $R_f$0.54 (2:1 ethyl acetate-hexane); $^1$H NMR (400 MHz, $CDCl_3$) δ6.44 (s, 1H), 5.86 (s, 1H), 5.83 (br s, 1H), 5.63 (s, 1H), 4.20 (d, J=2.3 Hz, 1H), 4.11 (dd, J=6.3, 3.2 Hz, 1H), 4.03 (d, J=2.3 Hz, 1H), 3.76 (s, 3H), 3.53 (br m, 2H), 3.35 (d, J=8.0 Hz, 1H), 3.16 (d, J=11.8 Hz, 1H), 2.99 (dd, J=18.2, 8.0 Hz, 1H), 2.76–2.72 (m, 2H), 2.30 (s, 3H), 2.28 (s, 3H), 2.26 (s, 3H), 2.21–2.08 (m, 4H), 2.00 (s, 3H), 1.64 (br m, 5H); FTIR (neat) 3445 (m br), 2935 (m br), 2864 (w), 1761 (m), 1708 (s), 1499 (w), 1433 (m), 1410 (m), 1373 (m), 1323 (w), 1299 (w), 1270 (w), 1231 (m), 1200 (m), 1145 (w), 1101 (m), 1075 (m), 1030 (w), 1005 (w), 935 (w) $cm^{-1}$; HRMS (FAB), [m+Na]/z calc'd for $C_{36}H_{38}O_8N_4Na$: 677.2587, found 677.2597.

EXAMPLE 61

Compound 62. The amount of Compound 9 was increased to 2.3 mg for this reaction. Preparative thin layer chromatography of the first step was done using 2:1 diethyl ether-hexane and again using 1:1 ethyl acetate-hexane. $R_f$0.50 (2:1 ethyl acetate-hexane); $^1$H NMR (400 MHz, $CDCl_3$) δ7.80 (s, 1H), 7.72 (dd, J=7.9, 1.7 Hz, 1H), 7.55 (d, J=7.8 Hz, 1H), 6.40 (s, 1H), 5.74 (s, 1H), 5.58 (s, 1H), 5.51 (br s, 1H), 4.24–4.19 (m, 2H), 4.01 (d, J=2.5 Hz, 1H), 3.69 (d, J=4.3 Hz, 2H), 3.62 (s, 3H), 3.36 (d, J=8.2 Hz, 1H), 3.18 (d, J=11.8 Hz, 1H), 3.01 (dd, J=18.0, 8.1 Hz, 1H), 2.75 (d, J=15.5 Hz, 1H), 2.69 (d, J=18.0 Hz, 1H), 2.28 (s, 6H), 2.24 (s, 3H), 2.00 (s, 3H), 1.68–1.62 (m, 1H); FTIR (neat) 3431 (m br), 3059 (w), 2934 (m br), 2858 (w), 1763 (s), 1719 (s), 1610 (w), 1499 (w), 1430 (s), 1386 (s), 1324 (m), 1298 (m), 1269 (m), 1231 (s), 1199 (s), 1145 (m), 1102 (s), 1075 (s), 1030 (m), 1003 (m), 945 (w), 905 (w) $cm^{-1}$; HRMS (FAB), [m+Na]/z calc'd for $C_{36}H_{33}O_8N_4BrNa$: 751.1379, found 751.1367.

EXAMPLE 62

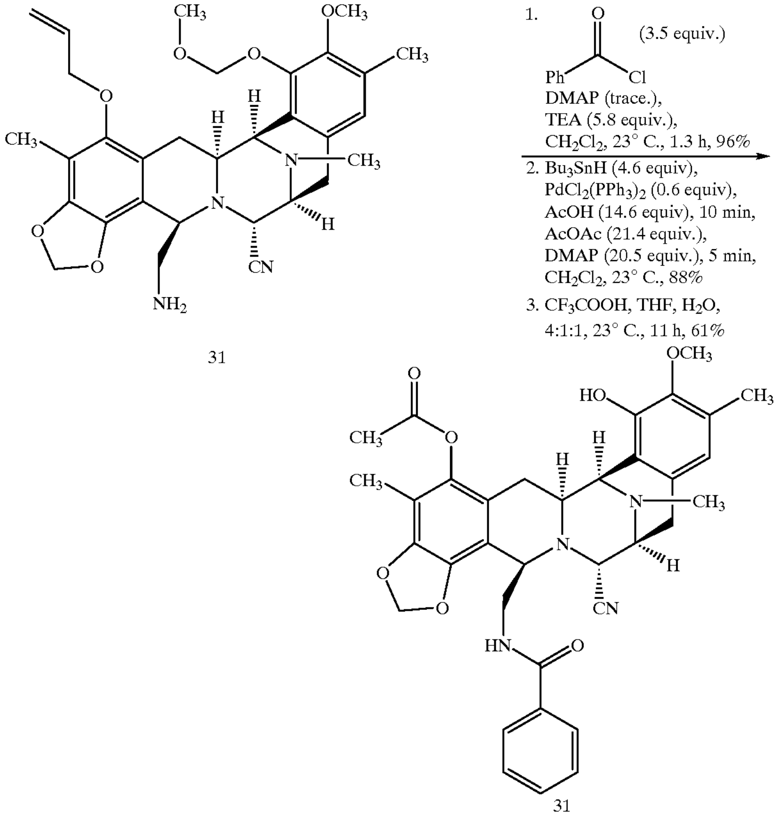

31

31

Amine (31) (0.7 mg, 0.0012 mmol) was dissolved in methylene chloride (0.3 mL). To this mixture was added 4-dimethylaminopyridine (trace), triethylamine (1.0 μL, 0.0072 mmol) and benzoyl chloride (0.5 μL, 0.0044 mmol). After stirring at 23° C. for 1.25 h the reaction was purified by flash column chromatography (1.0 mL silica gel, gradient methylene chloride to 1: 1 ethyl acetate-hexane) to afford Compound 64 (0.8 mg, 96%).

This residue was dissolved in methylene chloride (0.3 mL) and to this solution was added acetic acid (1.0 μL, 0.018 mmol), $PdCl_2(PPh_3)_2$ (0.5 mg, 0.7 μmol) and tributyltin hydride (1.5 μL, 0.0056 mmol). Bubbling was observed and the reaction changes from a yellow to a dark orange color. After stirring at 23° C. for 10 min the reaction was charged with 4-dimethylaminopyridine (3.0 mg, 0.025 mmol) and acetic anhydride (2.5 μL, 0.026 mmol). The reaction was stirred at 23° C. for 5 min and purified by flash column chromatography (1.0 mL silica gel, gradient methylene chloride to 2:1 ethyl acetate-hexane) to afford Compound 65 (0.7 mg, 88%).

The methoxymethyl ether (65) was dissolved in a mixture of trifluoroacetic acid-THF-water (4:1:1 (v/v), 1.0 mL) and the solution was stirred at 23° C. for 11 h. The reaction mixture was diluted with toluene (1 mL) and the solution was concentrated in vacuo. Additional volatiles were removed by repetitive in vacuo azeotropic concentration from toluene (3x1 mL). The residue was purified by preparative thin layer chromatography (2:1 diethyl ether-hexane, two elutions and 1:1 ethyl acetate-hexane) to afford Compound 63 (0.4 mg, 61%). $R_f$ 0.33 (2:1 ethyl acetate-hexane); $^1$H NMR (400 MHz, $CDCl_3$) δ7.32–7.37 (m, 1H), 7.25–7.23 (m, 4H), 6.18 (br s, 1H), 5.99 (s, 1H), 5.93 (s, 1H), 5.69 (br s, 1H), 5.61 (br s, 1H), 4.17 (br s, 2H), 4.08 (s, 1H), 3.65 (br s, 5H), 3.37 (d, J=7.2 Hz, 1H), 3.30 (d, J=12.0 Hz, 1H), 2.93 (dd, J=17.9, 7.4 Hz, 1H), 2.84 (d, J=15.8 Hz, 1H), 2.65 (d, J=17.7 Hz, 1H), 2.34 (s, 3H), 2.28 (s, 3H), 2.02 (s, 3H), 1.93–1.86 (m, 1H), 1.86 (br s, 3H); FTIR (neat) 3411 (m br), 2929 (s br), 2858 (m), 1757 (m), 1716 (m), 1655 (m), 1580 (w), 1524 (m), 1487 (s), 1452 (m), 1371 (m), 1293 (m), 1268 (m), 1231 (m), 1201 (s), 1151 (m), 1085 (s), 1030 (w), 1006 (w), 954 (w), 909 (w) $cm^{-1}$; HRMS (FAB), [m+Na]/z calc'd for $C_{35}H_{36}O_7N_4Na$: 647.2482, found 647.2455.

EXAMPLE 63

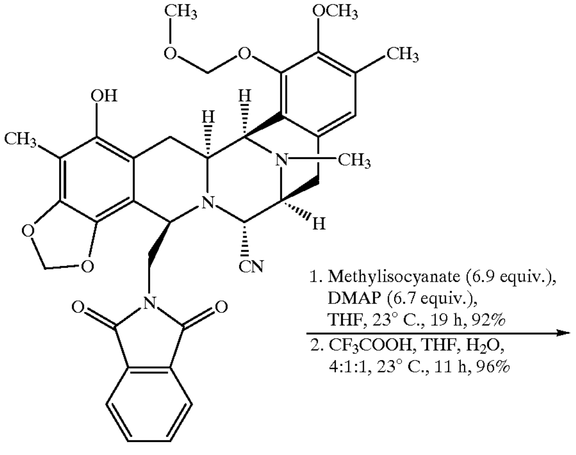

5

-continued

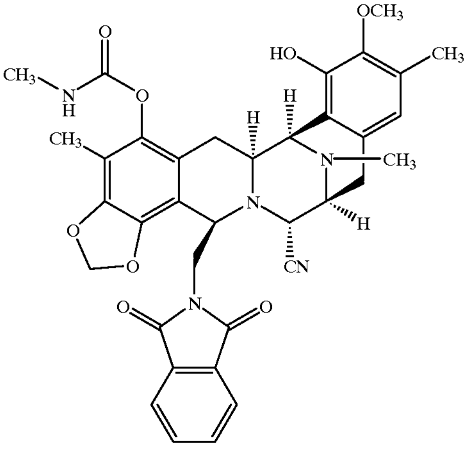

66

Phenol (5) (0.8 mg, 0.0012 mmol) was dissolved in THF (0.2 mL) and to this solution were added 4-dimethylaminopyridine (1.0 mg, 0.0082 mmol) and methylisocyanate (0.5 $\mu$L, 0.0085 mmol). The reaction was stirred at 23° C. for 19 h and then quenched into a saturated solution of aqueous sodium bicarbonate (2 mL). The mixture was extracted with 1:1 ethyl acetate-hexane (2x5 mL) and the organic layers were dried over sodium sulfate, decanted and concentrated in vacuo. The residue was purified by flash column chromatography (1 mL silica gel, gradient methylene chloride to 1:1 to 2:1 ethyl acetate-hexane) to afford Compound 67 (0.8 mg, 92%). This material was dissolved in a mixture of trifluoroacetic acid-THF-water (4:1:1 (v/v), 1.0 mL) and the solution was stirred at 23° C. for 11 h. The reaction mixture was diluted with toluene (1 mL) and the solution was concentrated in vacuo. Additional volatiles were removed by repetitive in vacuo azeotropic concentration from toluene (3x1 mL). The residue was purified by flash column chromatography (1 mL silica gel, gradient methylene chloride to 1:1 to 2:1 ethyl acetate-hexane) to afford Compound 66 (0.7 mg, 96%). $R_f$0.21 (2:1 ethyl acetate-hexane); $^1$H NMR (400 MHz, $CDCl_3$) δ7.73–7.70 (m, 2H), 7.69–7.66 (m, 2H), 6.36 (s, 1H), 5.63 (d, J=5.9 Hz, 1H), 5.18 (s, 1H), 5.03 (m, 1H), 4.23–4.21 (m, 2H), 4.05 (d, J=2.2 Hz, 1H), 3.67 (s, 3H), 3.63–3.55 (m, 2H), 3.34 (d, J=7.6 Hz, 1H), 3.23 (d, J=11.7 Hz, 1H), 3.06–2.95 (m, 2H), 2.88 (d, J=4.7 Hz, 3H), 2.85 (d, J=4.6 Hz, 1H), 2.60 (d, J=18.0 Hz, 1H), 2.29 (s, 3H), 2.20 (s, 3H), 2.02 (s, 3H), 1.78 (dd, J=15.8, 12.0 Hz, 1H); FTIR (neat) 3390 (m br), 2936 (m br), 2828 (w), 1771 (w), 1712 (s), 1647 (m), 1622 (w), 1519 (m), 1458 (m), 1430 (m), 1399 (m), 1322 (w), 1308 (w), 1232 (s), 1192 (w), 1109 (s), 1070 (m), 1029 (w), 1005 (w), 943 (w), 884 (w) $cm^{-1}$; HRMS (FAB), [m+Na]/z calc'd for $C_{36}H_{35}O_8N_5Na$: 688.2383, found 688.2392.

EXAMPLE 64

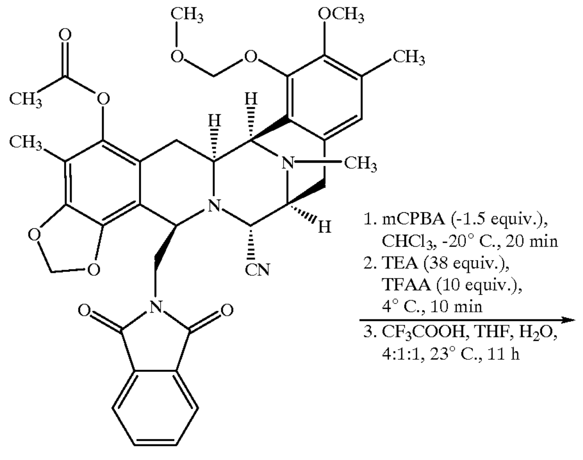

6

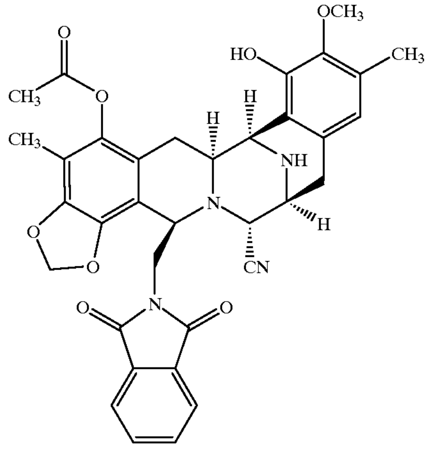

68

Compound 6 (2.7 mg, 0.0039 mmol) was dissolved in chloroform and the reaction was cooled to −20° C. To this solution was added solid m-chloro-peroxybenzoic acid (1.4 mg, −0.0058 mmol). The reaction was stirred at −20° C. for 20 min and the reaction was quenched with triethylamine (20 $\mu$L, 0.146 mmol). The reaction was warmed to 4° C. and trifluoroacetic anhydride (6 $\mu$L, 0.043 mmol) was added. After 10 min the reaction was poured into water (5 mL), extracted with methylene chloride (2x5 mL) and the organic layers were dried over sodium sulfate, decanted and concentrated in vacuo. The residue was purified by preparative thin layer chromatography (2:1 ethyl acetate-hexane, one elution) to afford starting material and two compounds related to desired product. These two compounds were dissolved in a mixture of trifluoroacetic acid-THF-water (4:1:1 (v/v), 1.0 mL) and the solution was stirred at 23° C. for 11 h. The reaction mixture was diluted with toluene (1 mL) and the solution was concentrated in vacuo. Additional volatiles were removed by repetitive in vacuo azeotropic concentration from toluene (3x1 mL). The residue was purified by flash column chromatography (1 mL silica gel, gradient methylene chloride to 1:1 to 2:1 ethyl acetate-hexane to ethyl acetate) to afford Compound 68 (0.6 mg, 25% over two steps). $R_f$ 0.21 (2:1 ethyl acetate-hexane); $^1H$ NMR (400 MHz, $CDCl_3$) δ7.74–7.71 (m, 2H), 7.69–7.65 (m, 2H), 6.41 (s, 1H), 5.66 (s, 1H), 5.63 (s, 1H), 5.29 (br s, 1H), 4.30 (d, J=2.8 Hz, 1H), 4.26 (d, J=1.7 Hz, 1H), 4.20 (t, J=5.8 Hz, 1H), 3.73–3.69 (m, 2H), 3.65 (s, 3H), 3.64–3.62 (m, 2H), 3.15–3.07 (m, 2H), 2.85 (d, J=18.0 Hz, 1H), 2.81 (d, J=16.2 Hz, 1H), 2.31 (s, 3H), 2.22 (s, 3H), 1.99 (s, 3H), 1.74 (t, J=13.6 Hz, 1H); FTIR (neat) 3430 (m br), 3330 (w br), 2929 (m br), 2857 (w), 1764 (m), 1714 (s), 1499 (w), 1458 (m), 1431 (s), 1394 (s), 1376 (m), 1324 (w), 1300 (w), 1270 (w), 1201 (s), 1105 (s), 1081 (m), 1024 (w), 1011 (w), 945 (w), 908 (w) $cm^{-1}$; HRMS (FAB), [m+Na]/z calc'd for $C_{35}H_{32}O_8N_4Na$: 659.2118, found 659.2126.

Biological Results

The analogs described above were screened in vitro for anti-tumor activity.[9] The human cancer cell lines used in these assays include A-549 (Lung), HCT116 (Colon), A375 (Melanoma) and PC-3 (Prostate) and values are reported as $IC_{50}$ (ng/mL). The following tables summarize the activity of all the synthetic derivatives. An $IC_{50}$ reading greater than 100 ng/mL is considered inactive in the screening tests conducted on the compounds of the present invention. Lower values represent higher activity.

[9] Cancer cell antiproliferative assays were performed by Dr. Takashi Owa, a postdoctoral fellow in the Stuart L. Schreiber research group.

TABLE 5

Biologcial Data for B-Ring Substitution at Position $X_1$

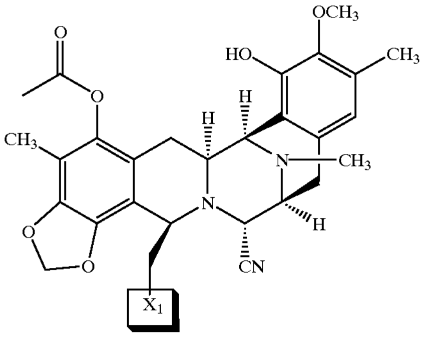

| Entry | Compound # | Analog ($X_1$ Group) | A-459 | HCT-116 | A375 | PC-3 |
|---|---|---|---|---|---|---|
| 1 | 7 | 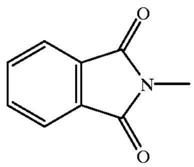 | 0.62 | 0.25 | 0.11 | 0.36 |
| 2 | 10 | 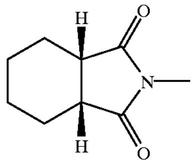 | 1.0 | 0.56 | 0.18 | 0.69 |
| 3 | 11 | 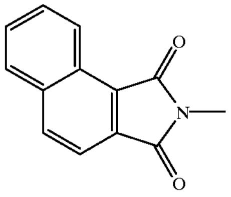 | 2.4 | 1.1 | 0.67 | 2.1 |
| 4 | 12 | 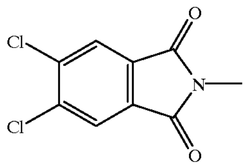 | 2.6 | 1.8 | 0.75 | 1.7 |

TABLE 5-continued
Biologcial Data for B-Ring Substitution at Position $X_1$
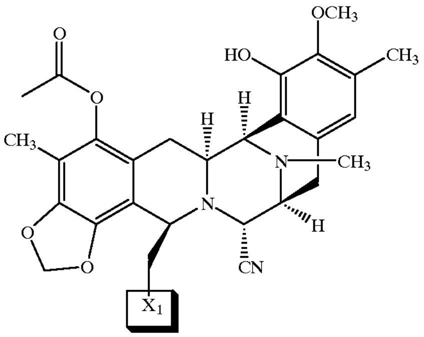
| Entry | Compound # | Analog ($X_1$ Group) | A-459 | HCT-116 | A375 | PC-3 |
|---|---|---|---|---|---|---|
| 5 | 13 | 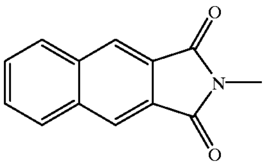 | 3.6 | 1.7 | 0.40 | 1.7 |
| 6 | 22 | 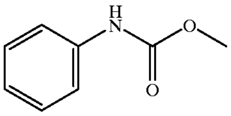 | 4.5 | 2.3 | 1.9 | 2.6 |
| 7 | 20 | 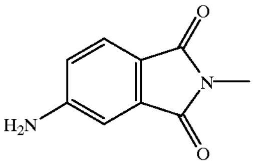 | 14 | 2.1 | 0.79 | 2.0 |
| 8 | 14 | 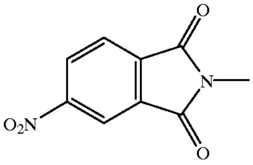 | 31 | 7.3 | 1.1 | 2.9 |
| 9 | 16 | 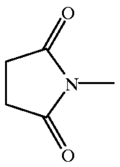 | 58 | 6.8 | 1.6 | 9.2 |
| 10 | 18 | 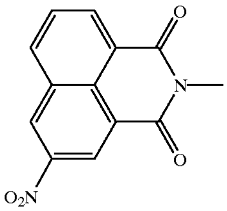 | 61 | 8.3 | 3.9 | 11 |

TABLE 5-continued
Biologcial Data for B-Ring Substitution at Position $X_1$
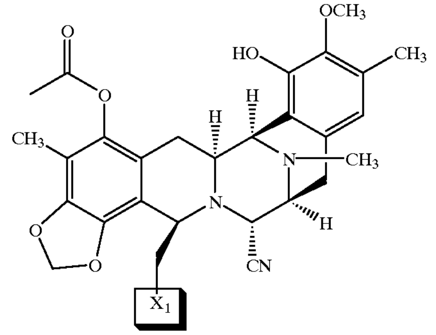
| Entry | Compound # | Analog ($X_1$ Group) | A-459 | HCT-116 | A375 | PC-3 |
|---|---|---|---|---|---|---|
| 11 | 56 | 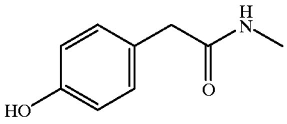 | >100 | 20 | 6.5 | 24 |
| 12 | 21 | 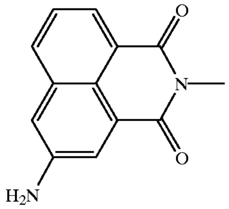 | >100 | 43 | 22 | 64 |
| 13 | 19 | 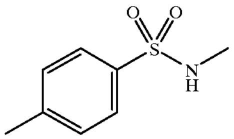 | >100 | 63 | 27 | 71 |
| 14 | 17 | 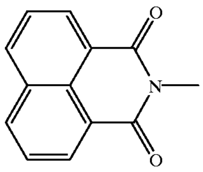 | >100 | 66 | 29 | 89 |
| 15 | 15 | 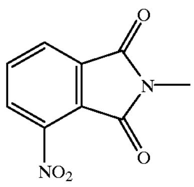 | >100 | 68 | 11 | 52 |
| 16 | 27 | 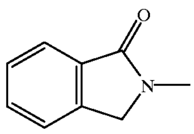 | 7.2 | 2.2 | 0.71 | 1.7 |

TABLE 5-continued
Biologcial Data for B-Ring Substitution at Position $X_1$
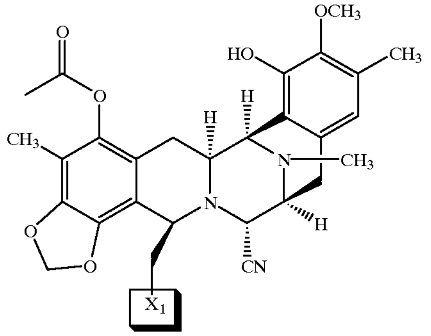
| Entry | Compound # | Analog ($X_1$ Group) | A-459 | HCT-116 | A375 | PC-3 |
|---|---|---|---|---|---|---|
| 17 | 28 | 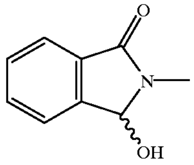 | 22 | 2.4 | 0.79 | 2.7 |
| 18 | 32 | 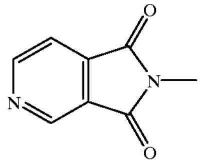 | 11 | 2.1 | 0.36 | 37 |
TABLE 6
Biological Data for A-Ring Substitution at Position $X_2$.
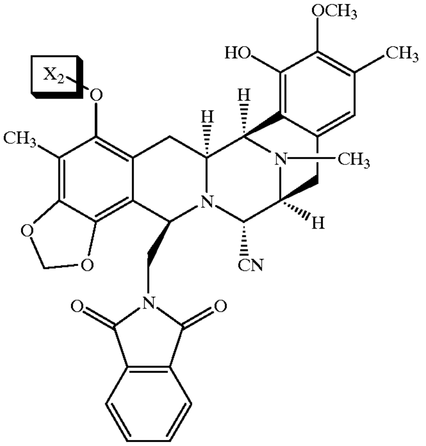
| Entry | Compound # | Analog ($X_2$ Group) | A-549 | HCT 116 | A375 | PC-3 |
|---|---|---|---|---|---|---|
| 1 | 7 | 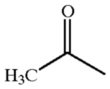 | 0.62 | 0.25 | 0.11 | 0.36 |
| 2 | 35 | 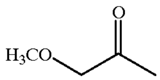 | 1.1 | 0.61 | 0.22 | 0.63 |

TABLE 6-continued
Biological Data for A-Ring Substitution at Position $X_2$.
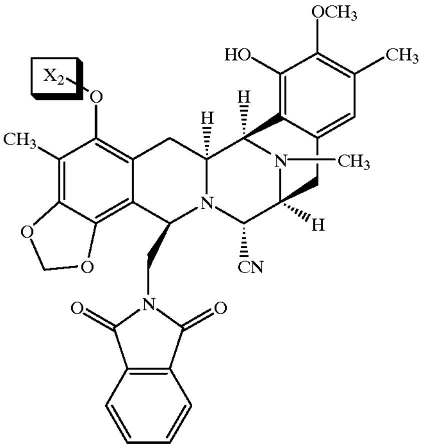
| Entry | Compound # | Analog ($X_2$ Group) | A-549 | HCT 116 | A375 | PC-3 |
|---|---|---|---|---|---|---|
| 3 | 44 | 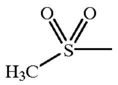 | 1.2 | 0.40 | 0.20 | 0.59 |
| 4 | 36 | 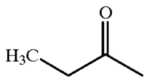 | 1.4 | 0.80 | 0.34 | 0.99 |
| 5 | 40 | 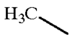 | 1.9 | 0.86 | 0.34 | 1.9 |
| 6 | 39 | 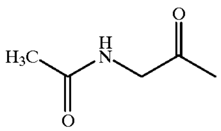 | 4.0 | 0.91 | 0.32 | 1.1 |
| 7 | 43 | 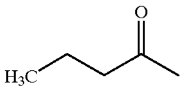 | 4.5 | 2.1 | 0.94 | 2.6 |
| 8 | 45 | 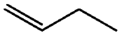 | 5.2 | 2.1 | 0.98 | 3.1 |
| 9 | 48 | 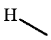 | 30 | 6.0 | 2.5 | 7.7 |
| 10 | 37 | 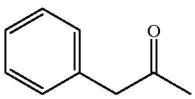 | 49 | 19 | 11 | 26 |
| 11 | 38 | 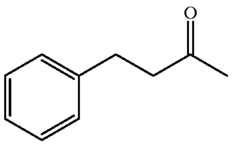 | 56 | 23 | 15 | 28 |

TABLE 6-continued
Biological Data for A-Ring Substitution at Position $X_2$.
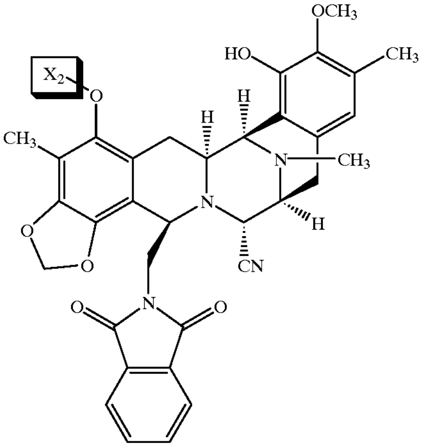
| Entry | Compound # | Analog ($X_2$ Group) | A-549 | HCT 116 | A375 | PC-3 |
|---|---|---|---|---|---|---|
| 12 | 41 | 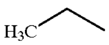 | 2.5 | 1.1 | 0.62 | 1.5 |
| 13 | 42 | 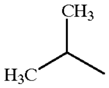 | 2.9 | 1.9 | 0.73 | 2.0 |
TABLE 7
Activity Data for Additional Analogs
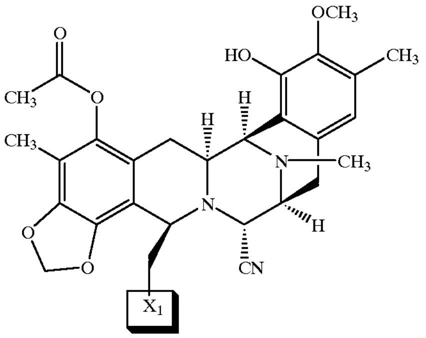
| No. | Analog ($X_1$ Group) | Lung | Colon | Melanoma | Prostate |
|---|---|---|---|---|---|
| 59 | 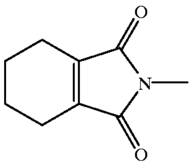 | 0.81 | 0.40 | 0.23 | 0.49 |
| 69 | 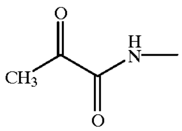 | 9.6 | 2.0 | 0.72 | 2.1 |

TABLE 7-continued
Activity Data for Additional Analogs
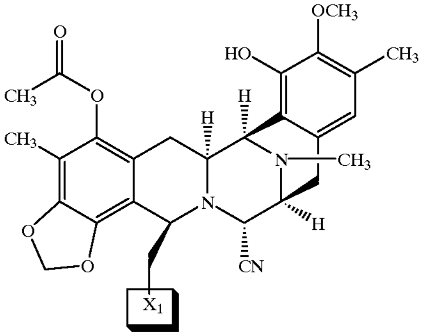
| No. | Analog ($X_1$ Group) | Lung | Colon | Melanoma | Prostate |
|---|---|---|---|---|---|
| 62 | 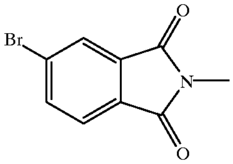 | 1.7 | 0.65 | 0.33 | 0.82 |
| 63 | 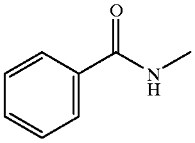 | 2.0 | 0.37 | 0.22 | 0.40 |
| 70 | 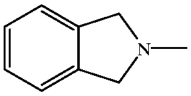 | 66 | 19 | 8.9 | 25 |
| | 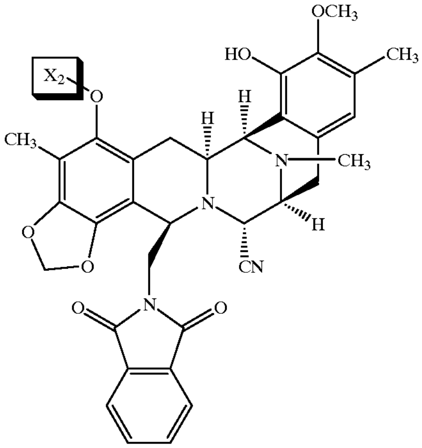 | | | | |
| 66 | 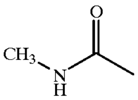 | 8.6 | 1.3 | 0.92 | 2.1 |

TABLE 8
Additional Biological Data:
| Structure | Cancer Cells | $IC_{50}$ (ng/mL) |
|---|---|---|
| 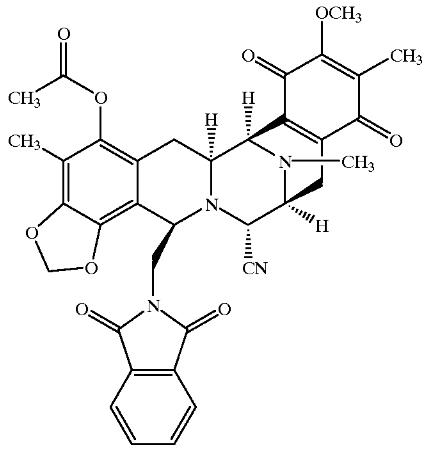 57 | Lung<br>Colon<br>Melan.<br>Prost. | 1.1<br>0.53<br>0.30<br>0.45 |
| 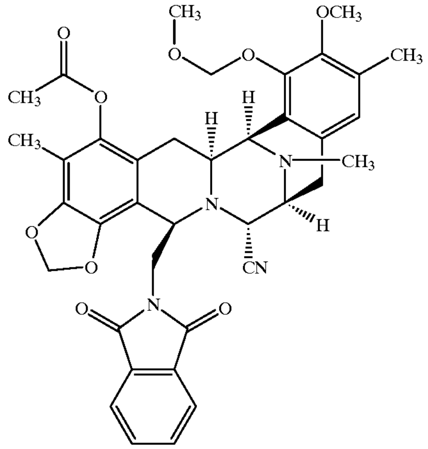 6 | Lung<br>Colon<br>Melan.<br>Prost. | 160<br>51<br>46<br>68 |
| 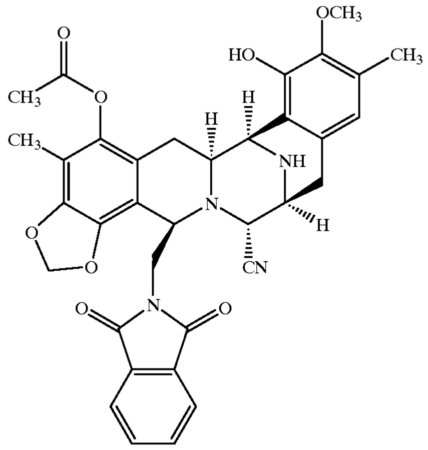 68 | Lung<br>Colon<br>Melan.<br>Prost. | 21<br>3.5<br>1.9<br>3.3 |

TABLE 8-continued
Additional Biological Data:
| Structure | Cancer Cells | $IC_{50}$ (ng/mL) |
| --- | --- | --- |
| 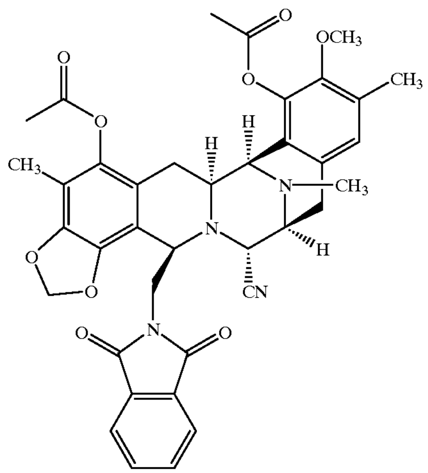 23 | Lung<br>Colon<br>Melan.<br>Prost. | 40<br>20<br>8.3<br>17 |
| 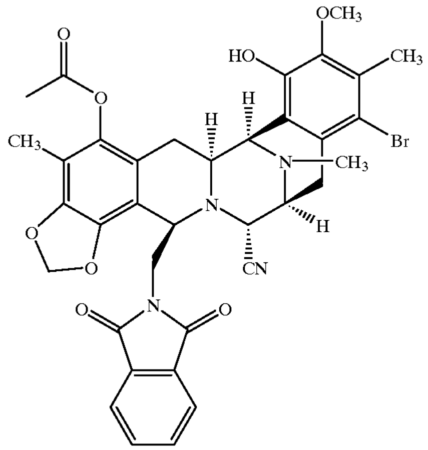 25 | Lung<br>Colon<br>Melan.<br>Prost. | 4.7<br>1.3<br>0.47<br>2.0 |
| 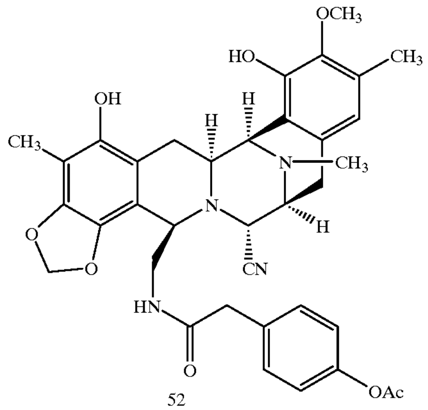 52 | Lung<br>Colon<br>Melan.<br>Prost. | >100<br>>100<br>>100<br>>100 |

TABLE 8-continued
Additional Biological Data:
| Structure | Cancer Cells | $IC_{50}$ (ng/mL) |
|---|---|---|
| 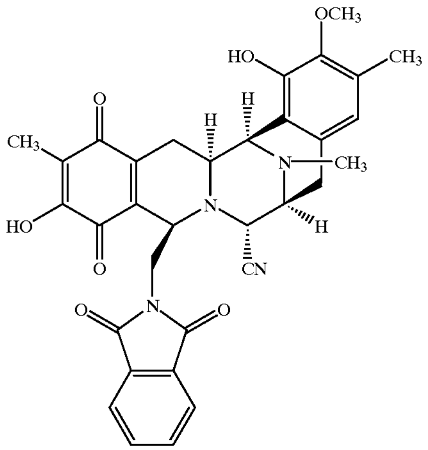 46 | Lung<br>Colon<br>Melan.<br>Prost. | 48<br>13<br>2.1<br>9.0 |
| 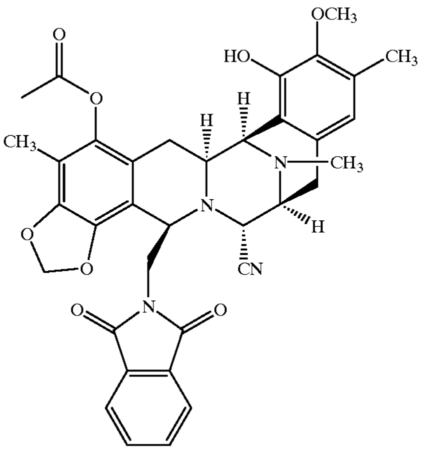 26 | Lung<br>Colon<br>Melan.<br>Prost. | 0.67<br>0.39<br>0.13<br>0.34 |
| 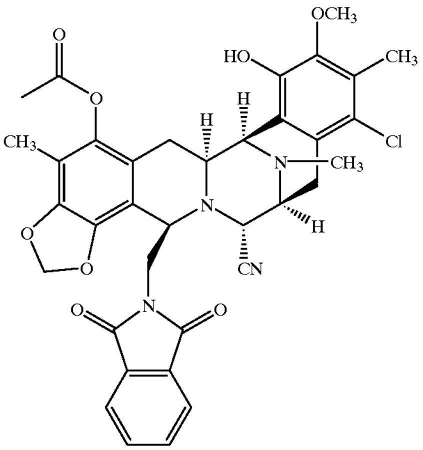 24 | Lung<br>Colon<br>Melan.<br>Prost. | 1.9<br>0.70<br>0.24<br>0.73 |

TABLE 8-continued

Additional Biological Data:

| Structure | Cancer Cells | $IC_{50}$ (ng/mL) |
|---|---|---|
| 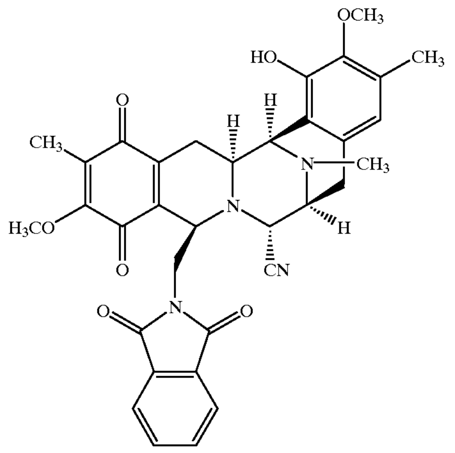 47 | Lung<br>Colon<br>Melan.<br>Prost. | >100<br>24<br>9.0<br>22 |

Based upon the tests performed to date, it is believed that the compounds of the present invention will serve as useful antitumor agents in mammals, particularly in humans.

Antitumor compounds are typically administered in unit dosage form. Each unit dose, as it pertains to the present invention, refers to a physically discrete unit suitable as unitary dosages for animals, each unit containing a predetermined quantity of active material calculated to produce the desired antitumor effect in association with the required diluent; i.e., carrier, or vehicle. The specifications for the novel unit dose of this invention are dictated by and are directly dependent on (a) the unique characteristics of the active material and the particular antitumor effect to be achieved, and (b) the limitations inherent in the art of compounding such active material for such use in mammals, particularly humans, as disclosed in detail herein, these being features of the present invention.

Unit dosage forms are typically prepared from the active compound by dispersement thereof in a physiologically tolerable (or acceptable) diluent or vehicle such as water, saline or phosphate-buffered saline, to form an aqueous composition. If necessary, other pharmaceutically acceptable solvents may be used. Such diluents are well known in the art and are discussed, for example, in *Remington's Pharmaceutical Sciences,* 16th Ed., Mack Publishing Company, Easton, Pa. (1980) at pages 1465–1467.

Dosage forms can also include an adjuvant as part of the diluent. Adjuvants such as complete Freund's adjuvant (CFA), incomplete Freund's adjuvant (IFA) and alum are materials well known in the art, and are available commercially from several sources.

The quantity of active compound to be administered depends, inter alia, on the animal species to be treated, the subject animal's size, the size of the tumor being treated (if known), and the capacity of the subject to utilize the active compound. Precise amounts of the active compound required to be administered depend on the judgment of the practitioner and are peculiar to each individual, particularly where humans are the treated animals. Dosage ranges, however, can be characterized by a therapeutically effective blood concentration and can range from a concentration of the active compound of the present invention from about 0.01 $\mu$M to about 100 $\mu$M, preferably about 0.1 $\mu$M to 10 $\mu$M.

Suitable regimes for initial administration and booster injections are also variable, but are typified by an initial administration followed by repeated doses at one or more hour intervals by a subsequent injection or other administration. Alternatively, continuous intravenous infusion sufficient to maintain therapeutically effective concentrations in the blood are contemplated.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. Compounds having the formula:

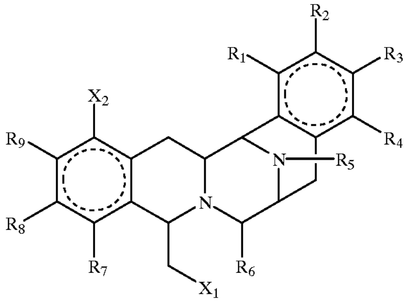

wherein each of the groups $X_1$, $X_2$, $R_1$, $R_2$, $R_3$, $R_4$, $R_5$, $R_6$, $R_7$, $R_8$ and $R_9$ is independently selected from the group consisting of H, OH, OR', SR', SOR', $SO_2R'$, $NO_2$, $NH_2$, NHR', $N(R')_2$, NHC(O)R', CN, halogen, =O, C(=O)H, C(=O)R', $CO_2H$, $CO_2R'$, $C_1$–$C_{12}$ alkyl, $C_2$–$C_{12}$ alkenyl, $C_2$–$C_{12}$ alkynyl, substituted or unsubstituted aryl, substituted or unsubstituted aralkyl, and substituted or unsubstituted heteroaromatic;

wherein each of the R' groups is independently selected from the group consisting of H, OH, $NH_2$, $NO_2$, SH, CN, halogen, =O, C(=O)H, C=O)$CH_3$, $CO_2H$, $CO_2CH_3$, $C_1$–$C_{12}$ alkyl, $C_2$–$C_{12}$ alkenyl, $C_2$–$C_{12}$ alkynyl, aryl, aralkyl, and heteroaromatic;

wherein each dotted circle represents one, two or three optional double bonds; and wherein $R_7$ and $R_8$ may be joined into a carbocyclic or heterocyclic ring system.

2. The compounds of claim 1 wherein $X_1$ and $X_2$ are independently selected from the group consisting of:

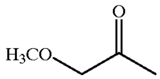
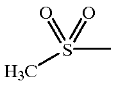
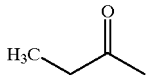
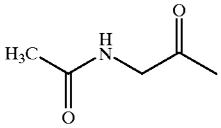
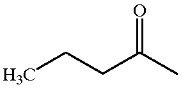
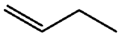
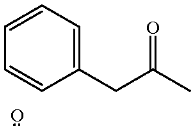
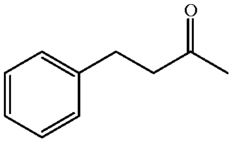
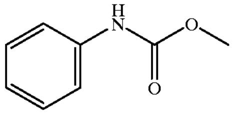
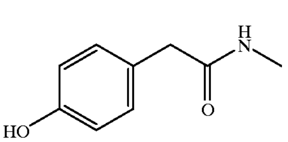
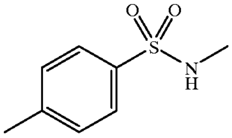
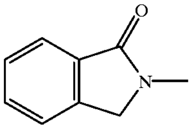
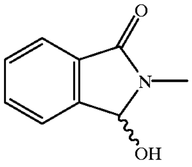

or the formula:

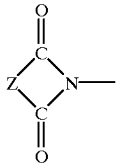

wherein Z is selected from the group consisting of:

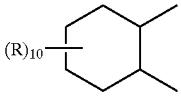
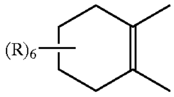
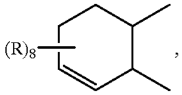
,
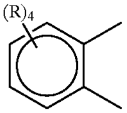

-continued

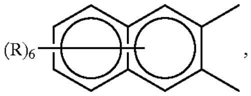
,
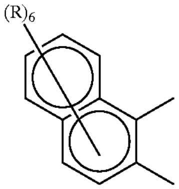
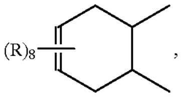
,
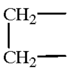
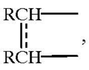
,
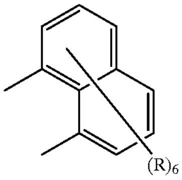
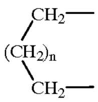
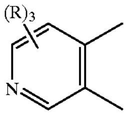
and
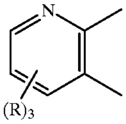

where n=1, 2, 3 . . . 20 wherein each R group is independently selected from the group consisting of H, OH, SH, $NH_2$, $NO_2$, halogen, nitro, $C_1$–$C_6$-alkyl, $C_1$–$C_6$-alkoxy, $C_1$–$C_6$-acyl, substituted or unsubstituted phenyl or substituted or unsubstituted benzyl.

3. Compounds of the formula:

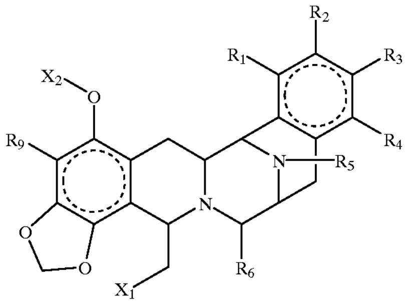

wherein each of the groups $X_1$, $X_2$, $R_1$, $R_2$, $R_3$, $R_4$, $R_5$, $R_6$, and $R_9$ is independently selected from the group consisting of H, OH, OR', SH, SR', SOR', $SO_2R'$, $NO_2$, $NH_2$, NHR', $N(R')_2$, NHC(O)R', CN halogen, =O, $C_1$–$C_6$ alkyl, substituted or unsubstituted aryl, substituted or unsubstituted aralkyl, and substituted or unsubstituted heteroaromatic;

wherein each of the R' groups is independently selected from the group consisting of H, OH, $NO_2$, $NH_2$, SH, CN, halogen, =O, C(=O)H, C(=O)$CH_3$, $CO_2H$, $CO_2CH_3$, $C_1$–$C_6$ alkyl, phenyl, benzyl, and heteroaromatic; and wherein each dotted circle represents one, two or three optional double bonds.

4. The compounds of claim 3, wherein $X_1$ and $X_2$ are each independently selected from the group consisting of:

-continued

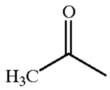 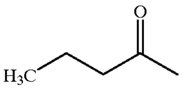 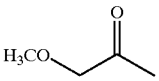

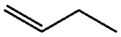 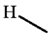 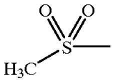

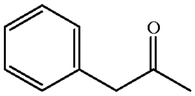 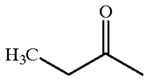

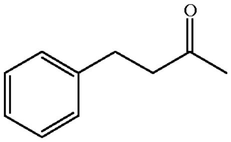 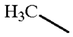 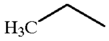

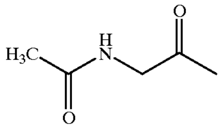 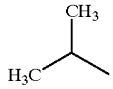

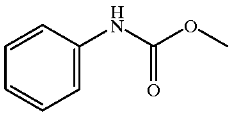 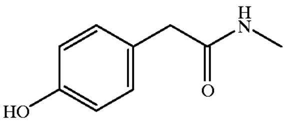

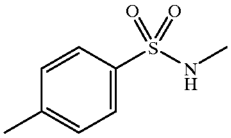 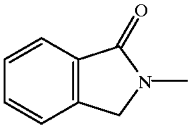

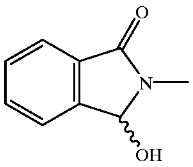

or the formula:

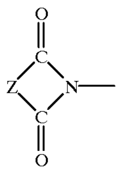

wherein Z is selected from the group consisting of:

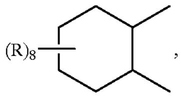 , 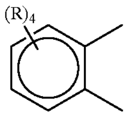

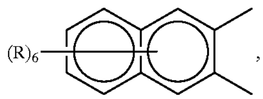 , 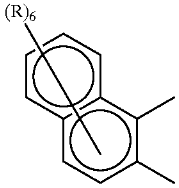

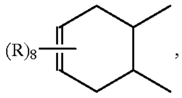 , 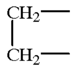 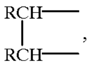 ,

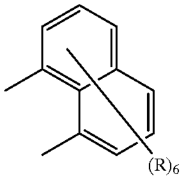 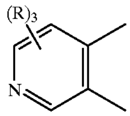 and

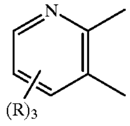

wherein each R group is independently selected from the group consisting of H, OH, SH, $NH_2$, $NO_2$, halogen, $C_1$–$C_6$-alkyl, $C_1$–$C_6$-alkoxy, $C_1$–$C_6$-acyl, aryl or alkylaryl.

5. The compound of the formula:

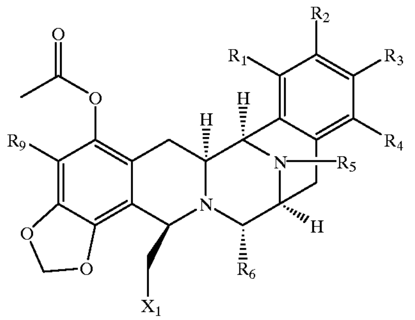

and pharmaceutically acceptable salts and derivatives thereof, wherein:

$R_1$ is H, OH, SH or $NH_2$;

$R_2$ is H, OH, $OCH_3$;

$R_3$ is H, OH, SH, $NH_2$ or $CH_3$;

$R_4$ is H, OH, SH, $NH_2$, $OCH_3$, or halogen;

$R_5$ is H or $C_1$–$C_6$ alkyl;

$R_6$ is CN, OH, SH, $NH_2$, OR, SR, or O(C═O)R;

$R_9$ is $C_1$–$C_6$ alkyl;

wherein $X_1$ is selected from the group consisting of:

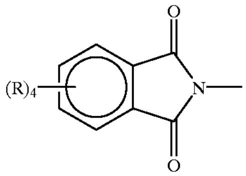 and

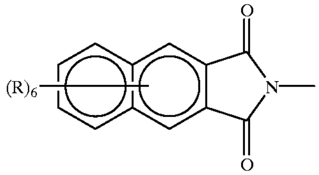

and where each R group, which may be the same or be different, is selected from the group consisting of H, OH, SH, $NH_2$, $NO_2$, halogen, $C_1$–$C_6$-alkyl, $C_1$–$C_6$-alkoxy, $C_1$–$C_6$-acyl, alyl or alkylaryl.

6. The compound of claim 5, wherein $X_1$ is:

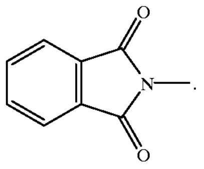

7. The compound of claim 5, wherein $X_1$ is:

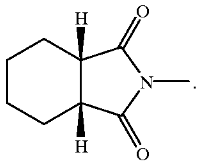

8. The compound of claim 5, wherein $X_1$ is:

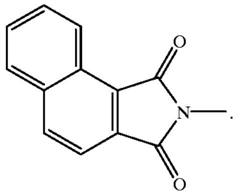

9. The compound of claim 5, wherein $X_1$ is:

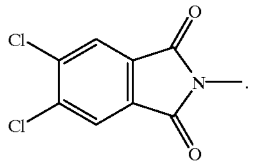

10. The compound of claim 5, wherein $X_1$ is:

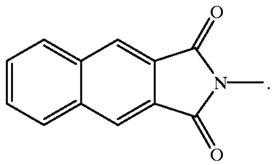

11. The compound of claim 5, wherein $X_1$ is:

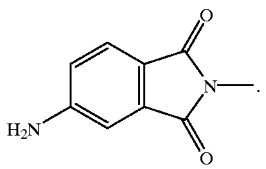

12. The compound of claim 5, wherein $X_1$ is:

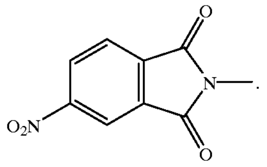

13. The compound of claim 9, wherein $X_1$ is:

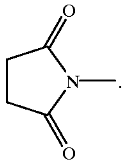

14. The compound of claim 5, wherein $X_1$ is:

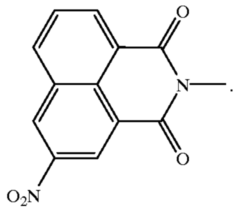

15. The compound of claim 5, wherein $X_1$ is:

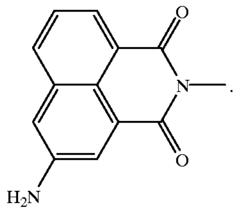

16. The compound of claim 5, wherein $X_1$ is:

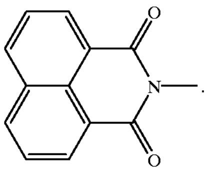

17. The compound of claim 5, wherein $X_1$ is:

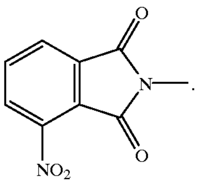

18. The compound of claim 5, wherein $X_1$ is:

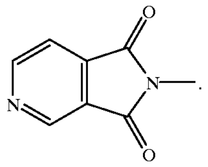

19. Pharmaceutical compositions comprising an effective antitumor amount of a compound of the formula:

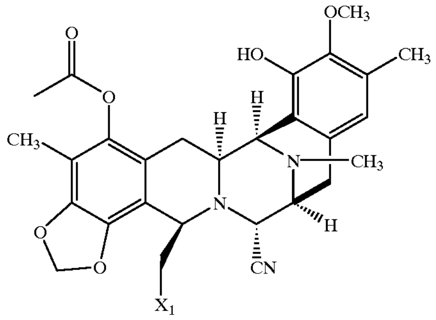

and pharmaceutically acceptable salts and derivatives thereof, wherein:

$R_1$ is H, OH, SH or $NH_2$;

$R_2$ is H, OH, $OCH_3$;

$R_3$ is H, OH, SH, $NH_2$ or $CH_3$;

$R_4$ is H, OH, SH, $NH_2$, $OCH_3$, or halogen;

$R_5$ is H or $C_1$–$C_6$ alkyl;

$R_6$ is CN, OH, SH, $NH_2$, OR, SR, or O(C=O)R;

$R_9$ is $C_1$–$C_6$ alkyl;

wherein $X_1$ is selected from the group consisting of:

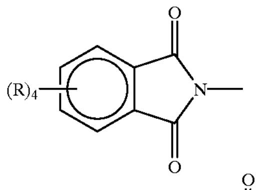

and

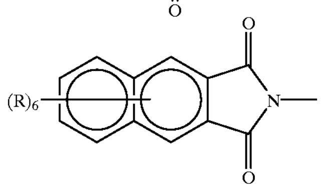

and wherein each R group, which many be the same or be different, is selected from the group consisting of H, OH, SH, $NH_2$, $NO_2$, halogen, $C_1$–$C_6$-alkyl, $C_1$–$C_6$-alkoxy, $C_1$–$C_6$-acyl, aryl or alkylaryl.

20. The pharmaceutical composition of claim 19, wherein $X_1$ is:

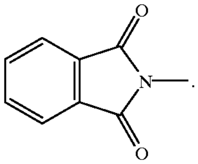

21. The pharmaceutical composition of claim 19, wherein $X_1$ is:

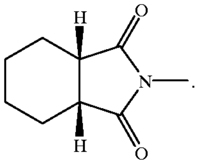

22. The pharmaceutical composition of claim 19, wherein $X_1$ is:

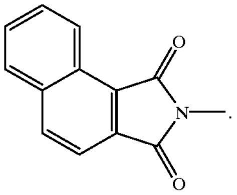

23. The pharmaceutical composition of claim 19, wherein $X_1$ is:

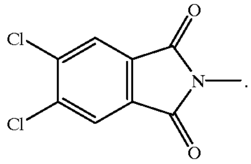

24. The pharmaceutical composition of claim 19, wherein $X_1$ is:

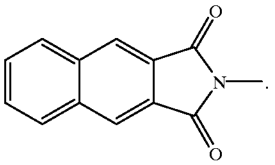

25. The pharmaceutical composition of claim 19, wherein $X_1$ is:

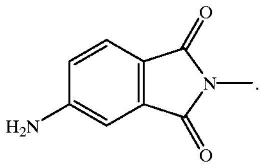

26. The pharmaceutical composition of claim 19, wherein $X_1$ is:

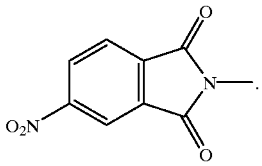

27. The pharmaceutical composition of claim 19, wherein $X_1$ is:

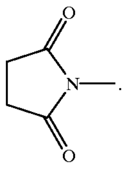

28. The pharmaceutical composition of claim 19, wherein $X_1$ is:

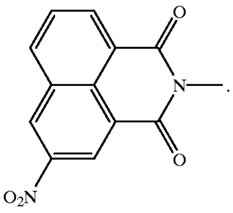

29. The pharmaceutical composition of claim 19, wherein $X_1$ is:

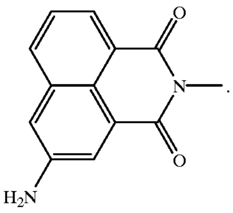

30. The pharmaceutical composition of claim 19, wherein $X_1$ is:

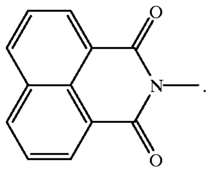

31. The pharmaceutical composition of claim 19, wherein $X_1$ is:

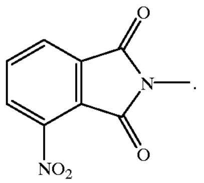

32. The pharmaceutical composition of claim 19, wherein $X_1$ is:

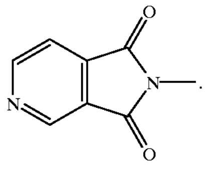

33. A method of treating tumors in mammals comprising administering to a mammal in need of such treatment, an effective antitumor amount of a compound of the formula:

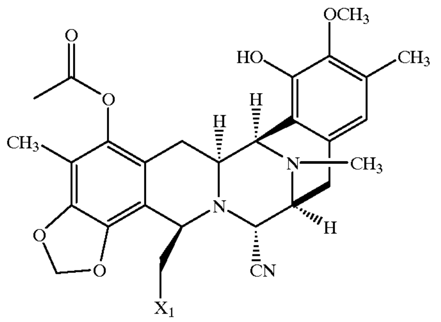

and pharmaceutically acceptable salts and derivatives thereof, wherein:

$R_1$ is H, OH, SH or $NH_2$;
$R_2$ is H, OH, $OCH_3$;
$R_3$ is H, OH, SH, $NH_2$ or $CH_3$;
$R_4$ is H, OH, SH, $NH_2$, $OCH_3$, or halogen;
$R_5$ is H or $C_1$–$C_6$ alkyl;
$R_6$ is CN, OH, SH, $NH_2$, OR, SR, or O(C=O)R;
$R_9$ is $C_1$–$C_6$ alkyl,
wherein $X_1$ is selected from the groupo consisting of:

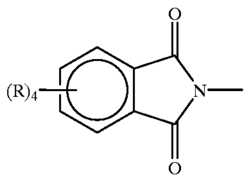

and

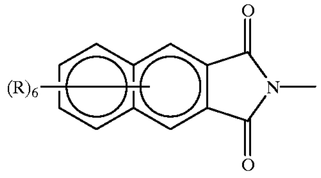

and wherein each R group, which may be the same or be different, is selected from the group consisting of H, OH, SH, $NH_2$, $NO_2$, halogen, $C_1$–$C_6$-alkyl, $C_1$–$C_6$-alkoxy, $C_1$–$C_6$-acyl, aryl or alkylaryl.

34. The method of treatment of claim 33, wherein $X_1$ is:

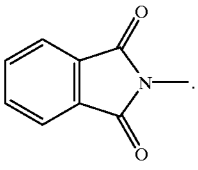

35. The method of treatment of claim 33, wherein $X_1$ is:

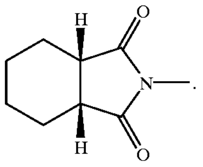

36. The method of treatment of claim 33, wherein $X_1$ is:

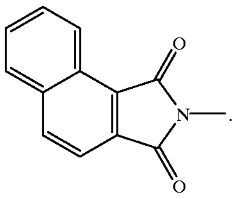

37. The method of treatment of claim 33, wherein $X_1$ is:

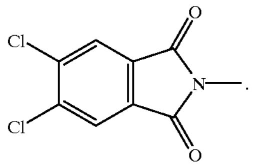

38. The method of treatment of claim 33, wherein $X_1$ is:

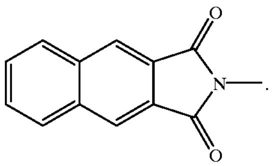

39. The method of treatment of claim 33, wherein $X_1$ is:

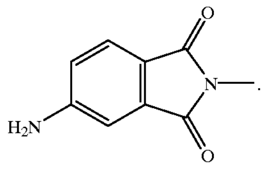

40. The method of treatment of claim 33, wherein $X_1$ is:

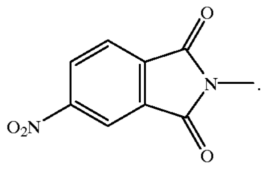

41. The method of treatment of claim 33, wherein $X_1$ is:

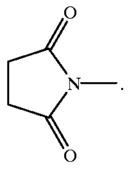

42. The method of treatment of claim 33, wherein $X_1$ is:

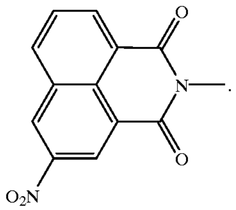

43. The method of treatment of claim 33, wherein $X_1$ is:

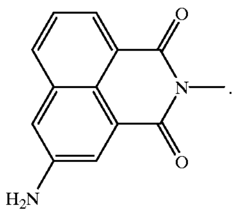

44. The method of treatment of claim 33, wherein $X_1$ is:

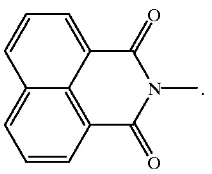

45. The method of treatment of claim 33, wherein $X_1$ is:

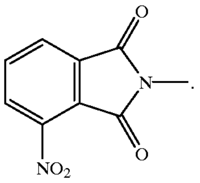

46. The method of treatment of claim 33, wherein $X_1$ is:

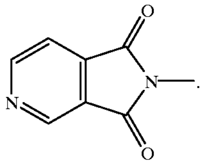

* * * * *